(12) United States Patent
Braun, III et al.

(10) Patent No.: US 9,723,797 B2
(45) Date of Patent: Aug. 8, 2017

(54) SELECTION OF MATURE FRUIT COLOR IN PEPPER PLANTS

(71) Applicant: Seminis Vegetable Seeds, Inc., St. Louis, MO (US)

(72) Inventors: Carl Joseph Braun, III, Woodland, CA (US); Eva King-Fan Chan, Rosebery (AU); Graeme S. Garvey, Woodland, CA (US); Carl Martin Jones, Sacramento, CA (US); Brian J. Just, Fort Myers, FL (US); Joel M. Kniskern, Sacramento, CA (US); Jonathan R. Mein, Concord, NC (US); Thomas C. Osborn, Kirkwood, MO (US); Petrus M. J. A. van Poppel, Wageningen (NL)

(73) Assignee: Seminis Vegetable Seeds, Inc., Woodland, CA (US)

( * ) Notice: Subject to any disclaimer, the term of this patent is extended or adjusted under 35 U.S.C. 154(b) by 172 days.

(21) Appl. No.: 14/304,722

(22) Filed: Jun. 13, 2014

(65) Prior Publication Data

US 2014/0380516 A1    Dec. 25, 2014

Related U.S. Application Data

(60) Provisional application No. 61/838,094, filed on Jun. 21, 2013, provisional application No. 61/863,765, filed on Aug. 8, 2013.

(51) Int. Cl.
| | |
|---|---|
| *A01H 5/08* | (2006.01) |
| *A01H 1/02* | (2006.01) |
| *B65B 25/04* | (2006.01) |
| *C12Q 1/68* | (2006.01) |
| *A01H 1/04* | (2006.01) |

(52) U.S. Cl.
CPC ............... *A01H 5/08* (2013.01); *A01H 1/02* (2013.01); *A01H 1/04* (2013.01); *B65B 25/04* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 8,026,424 | B2 * | 9/2011 | Van Der Heiden | A01H 5/08 |
| | | | | 435/421 |
| 8,044,273 | B2 * | 10/2011 | Van Der Heiden | A01H 5/10 |
| | | | | 435/421 |
| 8,067,681 | B2 * | 11/2011 | Van Der Heiden | A01H 5/10 |
| | | | | 435/421 |
| 2009/0313713 | A1 | 12/2009 | Lindeman | |
| 2010/0333224 | A1 * | 12/2010 | Leij | A01H 5/08 |
| | | | | 800/260 |
| 2010/0333225 | A1 * | 12/2010 | Leij | A01H 5/08 |
| | | | | 800/260 |
| 2010/0333226 | A1 * | 12/2010 | Leij | A01H 5/08 |
| | | | | 800/260 |

FOREIGN PATENT DOCUMENTS

| | | |
|---|---|---|
| WO | 2004089067 A1 † | 10/2004 |
| WO | WO 2011/028120 | 3/2011 |

OTHER PUBLICATIONS

Borovsky et al. Theoretical and Applied Genetics 117: 235-240 (2008).*
Brand et al., "pc8.1, a major QTL for pigment content in pepper fruit, is associated with variation in plastid compartment size," *Planta* 235(3):579-588, 2011.
"Baloian Farms added to specialty packs with BellaFina baby bell peppers," article 103896; available at <http://www.freshplaza.com/article/103896/Baloian-Farms-adds-to-specialty-packs-with-BellaFina-baby-bell-peppers>, Dec. 6, 2012.
Ramchiary et al., "Application of genetics and genomics towards Capsicum translational research," *Plant Biotechnology Reports* 8(2):101-123, 2013.
International Search Report and Written Opinion of the International Searching Authority for PCT/US2014/042392, dated Nov. 4, 2014.
Borovsky et al., "Induced mutation in β-Carotene Hydroxylase results in accumulation of β-carotene and conversion of red to orange color in pepper fruit," *Theoret Appl Genet* 126:557-565, 2013.
Britton, "Structure and properties of carotenoids in relation to function," *FASEB J* 9:1551-1558, 1995.
GenBank Accession No. DQ907615.1, "Capsicum annuum cultivar Nockwang capsanthin/capsorubin synthase, promoter region and partial sequence," dated Sep. 1, 2007.
GenBank Accession No. X77289, "C.annuum capsanthin/capsorubin synthase gene," dated Aug. 23, 1994.
GenBank Accession No. X91491, "C.annuum mRNA for xanthophyll epoxidase," dated Sep. 9, 2004.

(Continued)

*Primary Examiner* — David T Fox
(74) *Attorney, Agent, or Firm* — Dentons US LLP; Matthew Madsen Esq.

(57) ABSTRACT

The invention provides methods and compositions for breeding pepper (*Capsicum* sp. such as *Capsicum annuum*) lines, including isogenic and nearly isogenic lines, displaying one or more mature fruit color(s) of interest. Predictive genetic markers and associated sequences and primers, associated with phenotypic diversity at the Ccs locus encoding Capsanthin-Capsorubin Synthase, and the Ze locus encoding Zeaxanthin Epoxidase are also provided, as well as methods for breeding pepper lines. Further provided are pepper plants, and plant parts including seeds, seed mixtures, fruit, and packaged fruit, which display mature fruit color(s) of interest.

11 Claims, 34 Drawing Sheets

(56) References Cited

OTHER PUBLICATIONS

Genbank Accession No. X68017.1, "C.annuum psy1 mRNA for phytoene synthase," dated Feb. 5, 1994.
Guzman et al., "Variability of carotenoid biosynthesis in orange colored *Capsicum* spp.," *Plant Science* 179:49-59, 2010.
Ha et al., "A comparison of the carotenoid accumulation in Capsicum varieties that show different ripening colours: deletion of the capsanthin-capsorubin synthase gene is not a prerequisite for the formation of a yellow pepper," *J Experim Botany* 58:3135-3144, 2007.
Hill et al., "Linkage disequilibrium of finite populations," *Theoret Appl Genet* 38:226-231, 1968.
Kim et al., "A splicing mutation in the gene encoding phytoene synthase causes orange coloration in habanero pepper fruits," *Mol Cells* 30:569-574, 2010.
Lang et al., "Orange fruit color in *Capsicum* due to deletion of Capsanthin-capsorubin synthesis gene," *Breeding Science* 54:33-39, 2004.
Lefebvre et al., "The capsanthin capsorubin synthase gene: a candidate gene for the y locus controlling the red fruit colour in pepper," *Plant Mol Biol* 36:785-789, 1998.
Popovsky et al., "Molecular genetics of the y locus in pepper: its relation to capsanthin-capsorubin synthase and to fruit color," *Theoret Appl Genet* 101:86-89, 2000.
Purcell et al., "PLINK: A tool set for whole-genome association and population-based linkage analyses," *Am J Hum Genet* 81:559-575, 2007.
Thorup et al., "Candidate gene analysis of organ pigmentation loci in the Solanaceae," *PNAS USA* 97:11192-11197, 2000.
European Extended Search Report regarding European Application No. 14814153.4, dated Dec. 16, 2016.
Farré et al., "Travel advice on the road to carotenoids in plants," *Plant Science* 179:28-48, 2010.
Romer et al., "Genetic Engineering of a Zeaxanthin-rich Potato by Antisense Inactivation and Co-suppression of Carotenoid Epoxidation," *Metabolic Engineering* 4:263-272, 2002.
Wahyuni et al., "Metabolite biodiversity in pepper (*Capsicum*) fruits of thirty-two diverse accessions: Variation in health-related compounds and implications for breeding," *Phytochemistry* 72:1358-1370, 2011.
Document 7 Brand A Borovsky Y Meir S Rogachev I Aharoni A Paran I 2011 Pc8 1 A major QTL for pigment content in pepper fruit is associated with variation in plastid compartment size. Planta 235:3 579-588.†
Document 5 BellaFina Peppers Winner http www kmov com story 28496922 bellafina peppers winner, 2012.†
Document 1 Spain Consumption not growing as quickly as production http www freshplaza com article 101020 Spain Consumption not growing as quickly as production, 2012.†
Document 2 Pepper 2010 RZ Seeds and Services http www rijkzwaan nl wps wcm connect d09378dd baa9 4ae6 b015 bd224e150530 422688RZWmagPepper pdf MOD AJPERES.†
Document 3 Seeds and Service North America 2012 Rijk Zwaan http www rijkzwaanusa com wps wcm connect 72bd8cfe 7b7b 464d 9130 46cac54269b6 431097RZW SenS NorthAmerica2012 pdf MOD AJPERES.†
Document 4 Baloian Farms adds to specialty packs with Bella Fina baby bell peppers http www freshplaza com article 103896 Baloian Farms adds to specialty packs with BellaFina baby bell peppers, 2012.†
Document 6 Kim 2014 Genome squence of the hot pepper provides insights into the evolution of pungency in *Capsicum* spcies Nature Genetics 46:3 270-278.†
Document 8 Mixed Habanero Hot Pepper Gurneys Seed & Nursey http www gurneys com product mixed habaero hot pppper.†
Document 12 Ha SH Kim JB Park JS Lee SW Cho KJ, 2007 A comparison of the carotenoid accumulation in Capsicum varieties that show different ripening colours—deletion of the capsanthin-capsorubin synthase gene is not a prerequisite for the formation of a yellow pepper Journal of Exp Bio 58:12 3135-3144.†
Document 10 Bouvier F d Harlingue A Hugueney P Marin E., Marion—Poll A Camara B 1996 Xanthophyll biosynthesis cloning , expression functional reconstitution and regulation of B—cyclohexenyl carotenoid epoxidase from pepper Capsicum annuum The Journal of Biological Chemistry 271 28861-28867.†
Document 9 Sweet Bell Pepper Hybrid Mix Gurneys Seed & Nursey http www gurneys com product sweet bell pepper hybrid mix 2014.†
Document 11 Thorup TA Tanyolac B Livingstone KD Popovsky S Paran I Jahn M 2000 Candidate gene analysis of organ pigmentation loci in the Solanaceae PNAS 97:21 11192-11197.†
Document 13 Li Z Wang S Gui XL Chang X Gong Z 2013 A further analysis of the Relationship between yellow ripe-fruit color and the Capsanthin-Capsorubin synthase gene in pepper Capsicum sp indicated a new mutant variant in C annuum and a tandem repeat structure in promoter region PLOS ONE 8:4 e6 1996 1-9.†

\* cited by examiner
† cited by third party

SELECTION OF MATURE FRUIT COLOR IN PEPPER PLANTS

REFERENCE TO RELATED APPLICATIONS

This application claims the benefit of U.S. provisional application No. 61/863,765, filed Aug. 8, 2013, and U.S. provisional application No. 61/838,094, filed Jun. 21, 2013, which are herein incorporated by reference in their entireties.

BACKGROUND OF THE INVENTION

1. Incorporation Of Sequence Listing

The sequence listing that is contained in the file named "SEMB011US_ST25.txt", which is 171 kilobytes as measured in the Microsoft Windows operating system and was created on Jun. 13, 2014, is filed electronically herewith and incorporated herein by reference.

2. Field of the Invention

The present invention relates to the field of plant breeding and, more specifically, to the development of pepper plants displaying a desired mature fruit color.

3. Description of Related Art

The goal of vegetable breeding is to produce varieties displaying one or more desirable traits, such as a desired mature fruit color. Pepper plants (*Capsicum* sp.) may display, for instance, a mature fruit color of red, red-orange, orange, or yellow as a result of the function of pigment biosynthetic pathway(s) which produce pigments such as carotenes and xanthophylls.

SUMMARY OF THE INVENTION

In one aspect, the invention provides a package of pepper fruits comprising at least two different colors of pepper fruits selected from the group consisting of red, yellow, orange, and red-orange, wherein the peppers are grown from near isogenic pepper varieties. In one embodiment, the package comprises from about 1 to about 5 pepper fruits per color. In further embodiments, the pepper varieties are hybrid varieties. The package may contain, for example, at least three or at least four different colors of pepper fruits. The package may also comprise a green pepper fruit. In certain embodiments, the peppers are grown from at least two hybrid varieties that share a parent line. The hybrid varieties may also all share a parent line. In still further embodiments, the pepper varieties are *Capsicum annuum, C. baccatum, C. chinense, C. frutescens*, or *C. pubescens* varieties. In another embodiment, the pepper varieties are sweet peppers.

In another aspect, the invention provides a method of producing pepper fruits comprising: growing at least two near isogenic pepper lines that collectively comprise functional and non-functional Ccs and Ze alleles, and harvesting pepper fruit therefrom, wherein the pepper fruit are of at least two different colors selected from the group consisting of red, yellow, orange, red-orange, and green. The method can further comprise, in one embodiment, packaging the pepper fruit in a single package, wherein the pepper fruit are of at least two different colors selected from the group consisting of red, yellow, orange, red-orange, and green.

In still another aspect, the invention provides a container comprising seeds of at least two near isogenic pepper varieties, wherein the pepper varieties produce fruit of different fruit colors, and wherein the fruit colors are selected from the group consisting of: red, yellow, orange, and red-orange. In one embodiment, the container is defined as comprising seeds of at least three near isogenic pepper varieties that produce fruit of different fruit colors. In another embodiment, the container comprises seeds of at least four near isogenic pepper varieties that produce fruit of different fruit colors.

In still yet another aspect, the invention provides a method of producing pepper seed comprising: (a) producing a set of near isogenic inbred pepper lines that collectively comprise functional and non-functional Ccs and Ze alleles; (b) crossing said pepper lines to produce seed of near isogenic hybrid plants that comprise combinations of said alleles that result in red, yellow and orange fruit. In one embodiment of the method, producing a set of near isogenic lines comprises producing a plant that has been inbred but segregates for a Ccs or Ze allele. Producing a set of near isogenic lines may comprise, for example, producing a plant that has been inbred but segregates for Ccs and Ze alleles. In the method, the plant that has been inbred may be selfed for three or more generations. In certain embodiments of the method, producing a set of near isogenic inbred pepper lines comprises marker assisted selection for a Ccs or Ze allele. In other embodiments, producing a set of near isogenic inbred pepper lines comprises marker assisted selection for Ccs and Ze alleles. Marker assisted selection may comprise, in specific embodiments, detecting a deletion in a Ccs gene or the absence thereof. Marker assisted selection may also or alternatively comprise detecting a single nucleotide polymorphism in a Ze gene or the absence thereof. The near isogenic inbred pepper lines may, in one example, be homozygous for said Ccs and Ze alleles. In still further embodiments, the pepper lines are selected from the pepper species consisting of *Capsicum annuum, C. baccatum, C. chinense, C. frutescens*, and *C. pubescens*. In other embodiments, the pepper lines are sweet peppers.

In still yet another aspect, the invention provides a method of selecting a pepper plant for fruit color genotype comprising: (a) detecting the presence or absence of a polymorphism in the Zeaxanthin epoxidase (Ze) gene conferring said fruit color; and (b) selecting the plant based on the presence or absence of said polymorphism. In the method, detecting the presence or absence of a polymorphism in the Zeaxanthin epoxidase (Ze) gene may comprise detecting a genetic marker in linkage disequilibrium with said polymorphism. In another embodiment, detecting the presence or absence of a polymorphism in the Zeaxanthin epoxidase (Ze) gene comprises detecting the presence or absence of a single nucleotide polymorphism that is causative for said fruit color. In other embodiments, the method comprises detection of at least one genetic marker selected from the group consisting of: NE0235373, NE0240266, NE0239621, NE0240354, and NE0241248. In another embodiment, the method further comprises (c) crossing the selected plant from step (b) with a second pepper plant. In still other embodiments, the plant is a *Capsicum annuum* plant, and may be a sweet pepper plant.

BRIEF DESCRIPTION OF DRAWINGS

FIG. 5: Alignment of the sequences of the Ze gene derived from pepper line CM334 (line labeled "contig36343", SEQ ID NO:99), representative yellow (SEQ ID NO:96) and orange (SEQ ID NO:97) pepper lines, and the predicted coding sequence (SEQ ID NO:98), with marker locations shown.

FIG. 8: Alignment of Ccs sequences from 14 pepper lines (SEQ ID NOs:40-53).

DETAILED DESCRIPTION OF THE INVENTION

The invention provides methods and compositions relating to pepper (*Capsicum* spp., such as *C. annuum*) plants, and pepper plant parts, including seeds and fruit, and derivatives of such pepper plants/lines to allow for identification of pepper plants and production of nearly isogenic varieties which produce mature fruit of a desired color or colors, such as red, red-orange, orange, and/or yellow fruit.

Thus, in one aspect, the novel identification of a genetic trait allowing for orange mature fruit color in peppers (*Capsicum* spp.) as residing at the "Ze" locus encoding Zeaxanthin Epoxidase ("ZE" or "ZEP") on pepper chromosome 2, is disclosed herein. In another aspect, a deletion in the Capsanthin-Capsorubin Synthase (CCS) gene (termed "Ccs") is identified as a causal mutation leading to non-red mature pepper fruit color, allowing for use of genetic markers linked to a known allele of the Ccs gene via marker assisted selection ("MAS") or marker assisted backcrossing ("MABC"), when breeding for diverse mature fruit color in pepper plants. Pepper plants comprising a genetic marker linked to a known allele of the CCS gene may thus be utilized to breed pepper plants which display a desired mature fruit color, including red, orange, red-orange, and yellow. Further, use of both Ze and Ccs-encoded traits, and associated genetic markers, allows for production of collections of pepper lines and plants which produce fruit displaying desired mature fruit color, including lines which produce mature fruit displaying one or more desired mature fruit colors such as red, red-orange, orange, and yellow, and any combination thereof.

Figure 1:
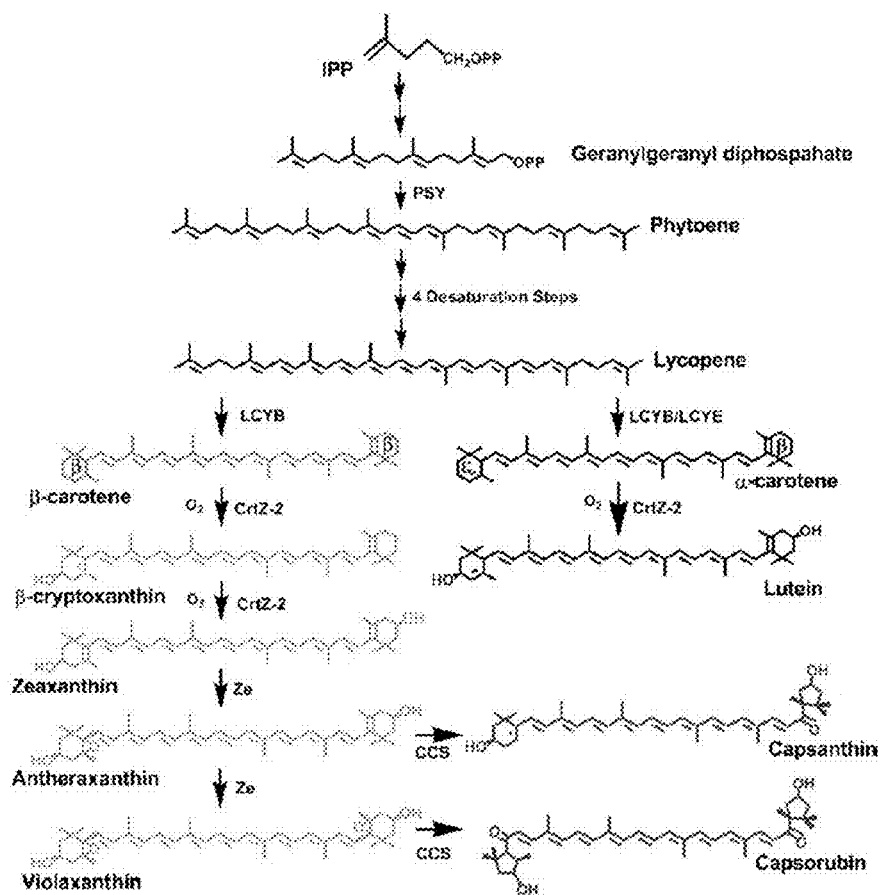
FIG. 1: Schematic presentation of the carotene and xanthophyll biosynthetic pathway in *Capsicum* sp. (from Guzman et al., *Plant Science* 179:49-59, 2010).

Plants with a functional carotenoid biosynthesis pathway upstream of compounds antheraxanthin and violaxanthin and a functional CCS protein are able to produce red pigments (carotenoids) in mature fruits, while plants that lack a functional CCS protein will not produce red fruits (Guzman et al. *Plant Sci.* 179:49-59, 2010; FIG. 1). Typically, these plants without a functional CCS protein have yellow or orange fruits. Carotenoids are largely responsible for the phenotypic colors of red, yellow, and orange pepper fruits. Due to the extensive conjugated double bond network and delocalized π-electrons, carotenoids absorb light in the visible range (400-500 nm) resulting in intense coloration of yellow, orange, and red (Britton, *FASEB J.* 9:1551-1558, 1995). The predominate carotenoids found in pepper fruits can be grouped according to their visual color class, which is based upon the number of conjugated double bonds. The major red carotenoids are capsanthin and capsorubin and absorb UV in the 470-475 nm range. The major orange carotenoids are zeaxanthin, β-carotene, and β-cryptoxanthin and absorb UV in the 450-455 nm range. The major yellow carotenoids are violaxanthin, antheraxanthin, and lutein and absorb UV in the 440-445 nm range. Thus, changes in the carotenoid profile have the potential to alter phenotypic fruit color.

Several enzymatic steps are required for the biosynthesis of carotenoids. Perturbations in the biosynthetic pathway can alter the carotenoid profile, ultimately resulting in phenotypic changes in fruit color. Capsanthin-Capsorubin Synthase and Zeaxanthin Epoxidase represent critical junctions in the pepper carotenoid biosynthetic pathway (FIG. 1). CCS is responsible for the formation of the red carotenoids capsanthin and capsorubin. ZEP catalyzes the epoxidation of the terminal 3-hydroxy-β-ionone ring structure of zeaxanthin, resulting in the formation of the di-epoxide violaxanthin via the mono-epoxide antheraxanthin. Both antheraxanthin and violaxanthin, in turn, serve as substrates for the CCS enzyme. Thus, the presence or absence of a fully functional CCS and/or ZEP enzyme impacts the biosynthesis of the red and yellow carotenoids, resulting in a change in carotenoid profile in mature fruit, and corresponding changes in fruit color.

Previously, the genetic basis of orange color in habanero peppers (*Capsicum chinense*) was reported to be due to a mutation in the gene encoding phytoene synthase ("Psy;" Thorup et al., *PNAS* 97:11192-11197, 2000). However, the orange line used in creating a polymorphic population for that mapping study was a habanero type pepper (*Capsicum chinense*), and the phytoene synthase gene was not known to contribute functional polymorphism affecting orange fruit color in elite *Capsicum annuum* peppers. Other research has implicated another carotenoid biosynthetic gene, encoding β-Carotene Hydroxylase, as involved in specifying fruit color (e.g. Borovsky et al. *TAG* 126:557-565, 2013). Thus, the identification of functional polymorphism (i.e. causal single nucleotide polymorphisms or "SNPs") in the gene encoding Zeaxanthin epoxidase correlating with a change in mature fruit color in *C. annuum* is surprising and unexpected. Pepper plants which produce, for instance, fruit with orange mature fruit color may thus be identified and bred using the presently disclosed genetic markers and trait source(s). Identification of causal polymorphisms in the Ccs gene provides further compositions and methods for pepper breeding, and may be used separately or in conjunction with disclosed Ze genetic markers and traits, to produce pepper plants displaying a mature fruit color of interest.

Commercial peppers are primarily of the species *Capsicum annuum* (e.g. bell peppers), *Capsicum frutescens* (Tabasco pepper), *Capsicum chinense* (Habanero pepper), and *Capsicum baccatum*. Pepper is an herbaceous species, generally grown as an annual crop, with fruits that vary in color, pungency, shape, and size. For instance, the fruit may be sweet or hot (pungent) and blocky or pointed, half-long, or of the Dulce Italiano or Corno di Toro types, among others. In view of the disclosed methods and compositions, pepper plants which produce fruit of different pungency levels and of various shapes, colors, and sizes are contemplated. Also contemplated are seeds, seed mixtures, cells, vegetative propagules, and fruit of the isogenic, nearly isogenic, or hybrid pepper lines which may thus be developed.

Utilizing genetic markers as disclosed herein, and/or markers genetically linked to these identified loci, and source lines, the methods described herein allow for production of nearly isogenic lines that differ in the mature fruit colors red, yellow, red-orange, and orange, and loci tightly linked to the color loci, but otherwise have essentially the same agronomic properties. These nearly isogenic lines can be used to produce nearly isogenic hybrids, which are of interest because each of the differently colored nearly isogenic hybrids have substantially the same horticultural properties, allowing growers to manage each variety in the same way. In contrast, current red, yellow and orange commercial varieties are typically distinct and may each have different pruning, nutritional, or pest control needs, adding complexity and expense to operations producing more than one color type. Additionally, the present invention allows for simplified breeding of pepper lines for producing multi-colored pepper packs, which have become increasingly popular. Additionally, breeding and hybrid lines may be produced and identified, for instance by transferring elite traits from typically more agronomically advanced red-fruited lines in order to improve orange and yellow-fruited germplasm. In addition the invention allows for the first time the production of substantially identical pepper fruits that differ in color. The invention thus also provides collections, including prepackaged collections, of near isogenic pepper fruit differing in color.

In one non-limiting example of a breeding method provided herein, the described color markers enable the consolidation of multiple breeding programs based on color into one multi-color breeding program. This can be achieved by crossing a red line that has both the intact Ccs and Ze alleles (CCSCCS ZEZE) with an orange line (ccsccs zeze) and maintaining both loci in a heterozygous state during breeding. In any given generation, a subset of plants heterozygous for both of these color loci can be subjected to MAS, and breeders may perform additional phenotypic selection on these plants as well. When the line is sufficiently genetically and phenotypically fixed after n generations, the line can be selfed and the progeny of the desired color genotype and phenotype can be selected using the markers for Ccs and Ze. This results in homozygous nearly isogenic lines that only differ in the mature fruit colors red, yellow, and orange, and loci tightly linked to the color loci. The invention thus provides, in one embodiment, a pepper plant comprising a desired mature fruit color trait, as well as a nearly isogenic pepper line comprising plants displaying a range of mature fruit colors. Diversity in the described color markers exists, for instance, in the commercial hybrids Orange Glory (ccsccs zeze), Derby (ccsccs ZEZE), Shanghai (ccsccs ZEZE), Aifos (CCSCCS ZEZE) and Darsena (CCSCCS ZEZE).

As used herein, "red," "red-orange," "orange," "yellow" and other contemplated fruit colors may be defined, for instance, by their visual color phenotype and absorption spectra of the underlying carotenoids. Yellow fruits appear yellow by visual assessment and the underlying carotenoids display a lambda max at approximately 442 nm; Orange fruits appear orange by visual assessment and the underlying carotenoids display a lambda max at approximately 454 nm; Red-Orange fruits appear red by visual assessment and the underlying carotenoids display a lambda max at approximately 454 nm; Red fruits appear red by visual assessment and the underlying carotenoids display a lambda max at approximately 474 nm. The visual contrast between Red-Orange and Red may usually be distinguishable upon side-by-side comparison but a grouping of only Red-Orange fruits would be visually assessed as being red in color.

As used herein, a "female parent" refers to a pepper plant that is the recipient of pollen from a male donor line, which pollen successfully pollinates an egg. A female parent can be any pepper plant that is the recipient of pollen.

As used herein, "male parent plant" refers to a parent plant that provides pollen to (i.e. is a pollinator for) a female line. They may be useful for breeding of progeny pepper plants, such as progeny plants which display a mature fruit color of interest.

As used herein, a "part of the pepper plant" is further defined as pollen, an ovule, a leaf, an embryo, a root, a root tip, an anther, a flower, a fruit, a stem, a cutting, a shoot, a seed, a protoplast, a cell, and a callus. A tissue culture of cells from a pepper plant may also be of use in propagating pepper plants of the present invention. As used herein, "tissue culture" refers to a composition comprising isolated cells of the same type(s) or of a different type, or of a collection of such cells, that may be organized into parts of a plant.

As used herein, a "hybrid pepper plant" includes a plant resulting directly or indirectly from crosses between populations, breeds or cultivars within the genus *Capsicum*. "Hybrid pepper plant" as used herein also refers to plants resulting directly or indirectly from crosses between different species, varieties or genotypes.

As used herein, a "marker" is a detectable polymorphism. Typically a marker is an indicator for the presence of at least one phenotype or genotype. Markers include, but are not limited to, single nucleotide polymorphisms (SNPs), small to large insertions and deletions, chromosomal rearrangements, cleavable amplified polymorphic sequences (CAPS), amplified fragment length polymorphisms (AFLPs), restriction fragment length polymorphisms (RFLPs), simple sequence repeats (SSRs), insertion(s)/deletion(s) ("INDEL"(s)), inter-simple sequence repeats (ISSR), and random amplified polymorphic DNA (RAPD) sequences. A marker may be inherited in codominant fashion (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism, phenotype, or both associated with a trait of interest. Stringent conditions for hybridization of a nucleic acid probe or primer to a marker sequence or a sequence flanking a marker sequence refers, for instance, to nucleic acid hybridization conditions of 1×SSC, and 65° C. As used herein, "marker assay" means a method for detecting a polymorphism at a particular locus using a particular method, e.g. measurement of at least one phenotype (such as a visually detectable trait, including disease resistance), restriction fragment length polymorphism (RFLP), single base extension, electrophoresis, sequence alignment, allelic specific oligonucleotide hybridization (ASO), random amplified polymorphic DNA (RAPD), microarray-based technologies, PCR-based technologies including TaqMan™, and nucleic acid sequencing technologies, etc.

As used herein, "near-isogenic" refers to a set of lines that are genetically highly similar (e.g. at least about 95% identical over the entire genome), but that differ with respect to chromosomal region(s) introduced from a "donor" parent line, such as a locus conferring fruit color as described herein. Near-isogenic varieties will generally share agronomic properties such that a farmer may apply substantially identical cultivation methods to grow a set of near isogenic varieties, and yield fruits that are essentially the same in appearance other than with respect to, for instance, fruit color.

Many useful traits that can be introduced by breeding strategies may also be introduced by genetic transformation techniques. Genetic transformation may therefore be used to insert a selected transgene, cisgene or intragene into a plant of the invention or may, alternatively, be used for the preparation of transgenes, cisgenes or intragenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts. Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques.

One aspect of the current invention thus concerns methods for producing seed for pepper hybrids that grow to yield fruit displaying a desired mature fruit color, such as red, red-orange, orange, or yellow, and shades thereof. Plants of a female pepper parent displaying the desired color trait, may be used in certain embodiments for the development of new (e.g. hybrid) pepper varieties, for instance via marker assisted selection. Alternatively or in addition, a pepper line may be developed by introgres sing one or more agronomic traits of interest into plant displaying a mature fruit color if interest.

The development of new varieties using one or more starting varieties is well known in the art. One or more presently disclosed genetic markers may be utilized in a marker assisted selection breeding method to create novel pepper lines or cultivars. Alternatively other mature fruit color-associated genetic markers may be identified by a skilled worker, and may be utilized in accordance with the invention. Thus novel varieties may be created by crossing lines displaying polymorphism at one or more fruit color-associated locus, followed by evaluation of fruit color characteristics of progeny plants, as well as genotyping, optionally evaluating other traits of agronomic interest. Thus, new varieties may be created by crossing with a second plant of a parental line chosen to exhibit one or more selected desirable characteristics or which exhibit the desired characteristic(s) when in hybrid combination. Once crosses have been made, selection may take place to identify new varieties.

The plants of the present invention are particularly well suited for the development of new lines based on the nature of the genetic background of the plants, particularly in view of available agronomically advanced traits of red-fruited parental lines, which allows for use in a method of producing seeds capable of growing into a pepper plant displaying a desired mature fruit color, as well as other agronomically useful traits such as, in specific embodiments, parthenocarpy, high seed yield, high seed germination, seedling vigor, high fruit yield, disease tolerance or resistance, and adaptability for soil and climate conditions. Consumer-driven traits, such as a fruit shape, color, texture, and taste are other examples of traits that may be incorporated into new lines of pepper plants developed in view of this invention.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

EXAMPLES

Example 1

Capsanthin-Capsorubin Synthase (CCS) Marker Development

Pepper plants comprising a functional carotenoid biosynthesis pathway upstream of compounds antheraxanthin and violaxanthin and a functional CCS protein are able to produce red pigments (carotenoids) in mature fruits, while plants that lack a functional CCS protein will not produce red fruits (Guzman et al. *Plant Sci.* 179:49-59, 2010; FIG. 1). Typically, plants lacking a functional CCS have yellow or orange fruits. The CCS gene was mapped to the y locus on chromosome 6 of pepper and the trait of red vs. yellow fruit color was found to map to the bottom of chromosome 6 using an F2:F3 mapping population from a cross between a yellow blocky-shaped line (designated SBY-29-469) and a red Italian fryer line (designated SZZ-8T10901), as shown in Table 1.

TABLE 1

Map position of the y locus for red vs. yellow mature fruit color ("RY color").

| Marker | Chromosome | SBY-29-469/SZZ-8T10901 F2:F3 | Map position (cM) |
|---|---|---|---|
| NE0239299 | 6 | 0 | 24.2 |
| NE0238978 | 6 | 8.5 | 30.2 |
| NE0238845 | 6 | 14.5 | 35.0 |
| NE0240908 | 6 | 33.7 | 62.6 |
| NE0235266 | 6 | 35.1 | 62.6 |
| NE0241110 | 6 | 44.5 | 70.6 |
| NE0237057 | 6 | 55.4 | 80.1 |

TABLE 1-continued

Map position of the y locus for red vs. yellow
mature fruit color ("RY color").

| Marker | Chromosome | SBY-29-469/SZZ-8T10901 F2:F3 | Map position (cM) |
|---|---|---|---|
| NE0240567 | 6 | 64.4 | 89.3 |
| NE0238405 | 6 | 91.9 | 107.4 |
| RY_color* | 6 | 123.4 | 120.6 |
| NE0237488 | 6 | 126.4 | 121.8 |
| NE0237446 | 6 | 136.4 | 132.4 |

*Red (R) vs. yellow (Y) color scored as a binary trait in F3 families to permit inference of all three genotypic classes in the F2 generation.

Additionally, genome wide association mapping provided additional evidence that the position of a causal mutation for red vs. non-red mature fruit color on chromosome 6 is general across sweet pepper germplasm. Data obtained from 2,836 mapped SNPs from a total of 209 red, 122 yellow, and 17 orange lines of the sweet blocky, sweet mini, and sweet long fruit types was used in a case-control association mapping analysis implemented in a whole genome association analysis toolset (PLINK; Purcell et al., *Am. J. Hum. Genet.* 81:559-575, 2007). The SNP with the most significant association to the red-vs. non-red trait (NE0237110) occurred at position 120.7 cM on chromosome 6.

Figure 2:
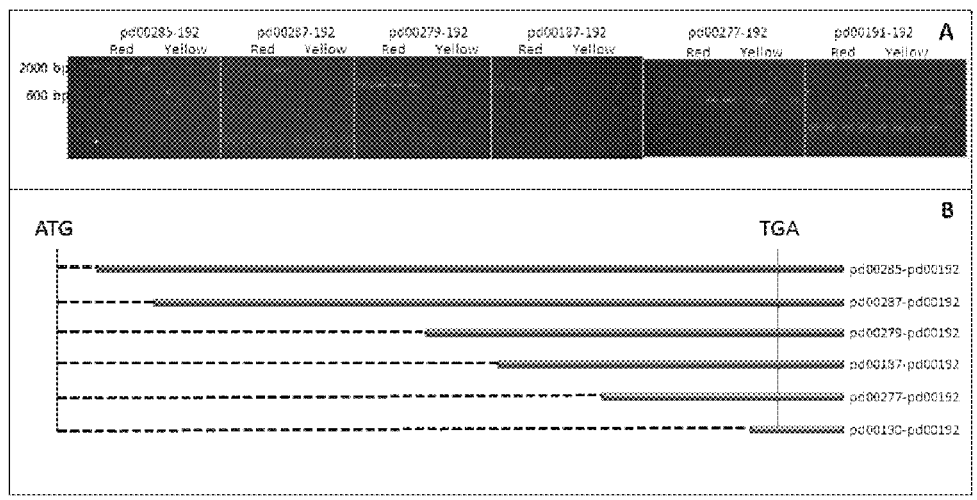
FIG. 2: PCR analyses reveal a deletion in the Ccs gene of non-red lines, as only primer combinations pd00277-pd00192 and pd00190-pd00192 yielded amplification products in both red and non-red (yellow) assayed lines. A) PCR amplicons obtained using different primer combinations in the Ccs gene. Primer combinations are listed on top of the panels. For each primer combination, four red and four yellow lines were used. B) Schematic representation of amplicons which were obtained; ATG and TGA respectively represent the start and stop codons of the Ccs gene. Next to each amplicon the expected amplicon size is indicated. Bars obtained with primers pd000285, pd000287, pd000279, and pd000187 represent amplicons obtained in red lines only; bars obtained with primers pd000277 and pd000190 represent amplicons obtained in all tested lines.

The Ccs gene sequence was previously deposited in Genbank (e.g. under accessions DQ907615.1 and X77289 (SEQ ID NO:1)). PCR analysis revealed that part of the CCS gene was deleted in certain studied pepper lines which produce non-red mature fruit. Primers were designed on parts of the CCS sequence and were used for PCR on red and non-red (yellow) lines (Table 2; SEQ ID NOs:2-9). Different forward primers were used, but in all PCR reactions primer pd00192 was used as reverse primer (Table 2; FIG. 2). Amplicons were always obtained from red lines, but in non-red lines amplicons were only obtained with primers that target the 3' region of the Ccs gene (FIG. 2). This inability to obtain amplicons is consistent with a deletion in the Ccs gene in non-red lines.

Figure 3:
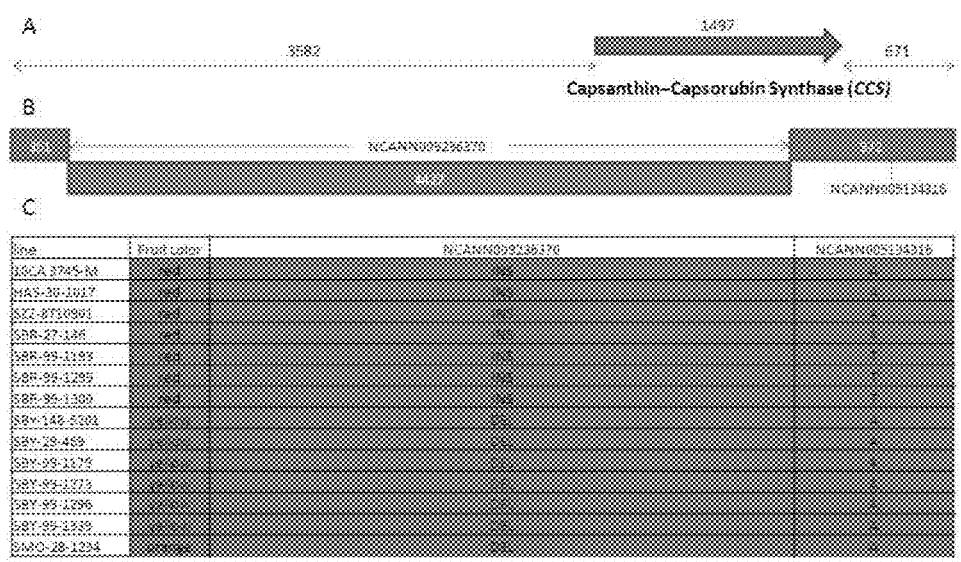
FIG. 3: A) Schematic representation of the Ccs gene and flanking sequences in a red pepper background. B) Size and position of the deletion found in both yellow and orange lines. C) Observed color of 14 tested pepper lines and the genotypes obtained with TaqMan™ markers NCANN009113770 (based on the deletion) and NCANN005134316 (based on an A/T SNP in the 3'UTR).

Genome walking experiments were performed to confirm the presence of a deletion in the Ccs gene of non-red lines. This analysis and additional sequencing showed that the Ccs gene contains an intact ORF in all red lines tested, while a 4472 bp deletion is present in all tested non-red lines (FIG. 3). The deletion covers most of the CCS ORF (1196 bp) and as a result only 351 bp of the sequence is conserved between red and non-red lines. Moreover, 3231 bp in the 5' UTR are absent in non-red lines compared to red lines. In the 3' UTR, a segment of 671 bp was conserved between red and non-red lines, albeit with several polymorphisms between these alleles. In total, 5750 bp of sequence was obtained from red pepper lines: 3582 bp of sequence was obtained from the 5' UTR, 671 bp from the 3' UTR, and the CCS ORF itself is 1497 bp in length. The observation that only red fruited lines have an intact Ccs gene leads to the conclusion that Capsanthin-Capsorubin Synthase is needed to convert the non-red carotenoids into the red carotenoids A TaqMan™ assay designated Q-NCANN009113770 was designed to assay the presence or absence of sequence at the 4472 bp deletion site in the Ccs gene. Primer and probe design for the NCANN009113770 assay are shown in Table 3 (SEQ ID NOs:10-14). Similarly performing assays can be designed by varying the position of the forward and reverse primers or by designing the primers against the complementary strand of DNA. The inferred fruit color phenotypes obtained with this marker on a line panel are shown in FIG. 3C. Another TaqMan™ assay designed for red vs. non-red marker assisted selection utilized marker NCANN005134316 (based on the A/T polymorphism in SEQ ID NO:19), and was designed to target an A/T SNP in the 3' UTR of Ccs. Primer and probe design for the NCANN009113770 assay are shown in Table 3 (SEQ ID NOs:15-18. This assay was predictive in approximately 95% of tested pepper germplasm. However, as shown in FIG. 3C, several lines with red fruits carry the A allele of NCANN005134316, associated with non-red fruits.

TABLE 2

Primers used to confirm deletion in Ccs gene of non-red lines
(SEQ ID NOs: 2-9; see also FIG. 2).

| Primer | Sequence (5'-3') | Orientation | Expected fragment size (bp) | Amplicon obtained in Red | Amplicon obtained in Yellow |
|---|---|---|---|---|---|
| pd00285 | CAACTCCACTTTTCCAAATC | F | 1884 | Yes | No |
| pd00287 | GGTTGATACTGATCTGGACG | F | 1743 | Yes | No |
| pd00279 | GTGAGTCGGCCTATGTTATCG | F | 1066 | Yes | No |
| pd00187 | TGGTGGGACTTCAGGGATAG | F | 903 | Yes | No |
| pd00277 | TGTTGATCCCAAGTACTGGC | F | 639 | Yes | Yes |
| pd00190 | AGACTTGGTATCAGATTGTGGC | R | 418 | Yes | Yes |
| pd00191 | AGCCACAATCCGATACCAAG | F | 246 | Yes | Yes |
| pd00192 | GAGGGACAAGAGTGGAGCAG | R | N/A | N/A | N/A |

TABLE 3

Primers and probes used for TaqMan™ assays NCANN009113770 and NCANN005134316 (SEQ ID NOs: 10-18).

| Name | Description | Sequence | Allele |
|---|---|---|---|
| NCANN009113770_F1 | forward primer 1 | TCGAAAGCCTTGGCTCAACA | |
| NCANN009113770_F2 | forward primer 2 | TTTTGTATCTCCCTTTCCCAGAA | |
| NCANN009113770_R | reverse primer | TCTCTAACACGTCTTCTATCCGAAGG | |
| NCANN009113770_V | VIC probe | AGAATGATAAGAGGGTCT | INS |
| NCANN009113770_M | FAM probe | CTTTTAGAGTTTGGAATG | DEL |
| NCANN005134316_F | forward primer | CCAAACACTTTGAATTGGCTGGATA | |
| NCANN005134316_R | reverse primer | ACTATATTAACTTTCCTAATAATTCTTGCTTTCCCA | |
| NCANN005134316_V | VIC probe | TGCTGITAATGATTAATAACAT | A* |
| NCANN005134316_M | FAM probe | CTGTTAATGATTAAAAACAT | T* |

*probes are designed on the reverse complement sequence

Table 4 shows an overview of the studied mutations found in the Ccs gene and flanking sequences (SEQ ID NOs:20-38). In total 13 additional SNPs and small indel mutations were identified in the 3' UTR of the Ccs gene (Table 4). Three of these are indel mutations (of 3, 4 and 14 bp respectively). The other 10 mutations are SNPs. Two of these SNPs were only found in line HAS-30-1017, which is consistent with the fact that the Asian germplasm is genetically divergent from the sweet pepper germplasm. One line-specific SNP was found in line SBY-99-1273.

TABLE 4

Overview of mutations found in the CCS gene and flanking sequences.
The INS/DEL identified by marker NCANN009113970 is given in SEQ ID NO: 39

| | | | | Marker Root Name | | | | |
|---|---|---|---|---|---|---|---|---|
| | Fruit color | NCANN00 5134316 [A/T] | NCANN00 9113770 [INS/DEL] | NCANN00 9113570 [T/c] | NCANN00 9113170 [C/a] | NCANN00 9113970 [TATGGTTGT CGATG/*] | NCANN00 9113370 [T/c] | NCANN00 9113971 [T/a] |
| SBR-99-1193 | Red | A | INS | T | C | * | C | T |
| SBR-99-1299 | Red | A | INS | T | C | * | C | T |
| SBR-99-1300 | Red | A | INS | T | C | * | C | T |
| HAS-30-1017 | Red | A | INS | T | C | TATGGTTG TCGATG | T | A |
| 10CA 3745-M | Red | T | INS | C | A | TATGGTTG TCGATG | T | T |
| SZZ-8T10901 | Red | T | INS | C | A | TATGGTTG TCGATG | T | T |
| SBR-27-146 | Red | T | INS | C | A | TATGGTTG TCGATG | T | T |
| SBY-148-5201 | Yellow | T | DEL | C | A | TATGGTTG TCGATG | T | T |
| SBY-29-469 | Yellow | T | DEL | C | A | TATGGTTG TCGATG | T | T |
| SBY-99-1179 | Yellow | T | DEL | C | A | TATGGTTG TCGATG | T | T |
| SBY-99-1273 | Yellow | T | DEL | C | A | TATGGTTG TCGATG | T | T |
| SBY-99-1296 | Yellow | T | DEL | C | A | TATGGTTG TCGATG | T | T |
| SBY-99-1339 | Yellow | T | DEL | C | A | TATGGTTG TCGATG | T | T |
| SMO-28-1234 | Orange | T | DEL | C | A | TATGGTTG TCGATG | T | T |

TABLE 4-continued

Overview of mutations found in the CCS gene and flanking sequences.
The INS/DEL identified by marker NCANN009113970 is given in SEQ ID NO: 39

| | Marker Root Name | | | | | | | |
|---|---|---|---|---|---|---|---|---|
| | NCANN 009113371 [G/t] | NCANN 009114170 [AACA/*] | NCANN 009114370 [A/c] | NCANN 009113571 [A/g] | NCANN 009113171 [G/t] | NCANN 009113372 [C/t] | NCANN 009113771 [G/t] | NCANN 009114171 [aac/*] |
| SBR-99-1193 | T | AACA | A | A | T | T | T | AAC |
| SBR-99-3299 | T | AACA | A | A | T | T | T | AAC |
| SBR-99-1300 | T | AACA | A | A | T | T | T | AAC |
| HAS-30-1017 | G | AACA | A | G | T | T | T | AAC |
| 10CA 3745-M | G | * | A | A | G | C | G | * |
| SZZ-8T10901 | G | * | A | A | G | C | G | * |
| SBR-27-146 | G | * | A | A | G | C | G | * |
| SBY-148-5201 | G | * | A | A | G | C | G | * |
| SBY-29-469 | G | * | A | A | G | C | G | * |
| SBY-99-1179 | G | * | A | A | G | C | G | * |
| SBY-99-1273 | G | * | C | A | G | C | G | * |
| SBY-99-1296 | G | * | A | A | G | C | G | * |
| SBY-99-1339 | G | * | A | A | G | C | G | * |
| SMO-28-1234 | G | * | A | A | G | C | G | * |

For accuracy tests, marker NCANN009113770 was validated on a panel of 615 leaf samples. The panel was derived from variety trials and predominantly contained lines that were developed for the Dutch greenhouse market. In all tested plants of visually-assessed fruit color, only two gave an unexpected genotype (Table 5), which are likely caused by a technical error, probably caused by a mistaken color description. Nonetheless, in this trial the marker is at least >99.6% accurate.

TABLE 5

Accuracy test results for marker NCANN009113770.

| | Genotype | | | |
|---|---|---|---|---|
| Observed | INSINS | INSDEL | DELDEL | — |
| | Inferred phenotype | | | |
| Phenotype | Red | Red | Not-red | — |
| Red | 294 | 22 | 1* | 12 |
| Yellow | 0 | 0 | 181 | 4 |
| Orange | 1* | 0 | 98 | 2 |

*conflict between inferred and observed phenotypes

In conclusion, marker NCANN009113770 is based on a large deletion mutation in the CCS gene; all available data suggests that this mutation prevents the formation of red pigment in non-red pepper fruits. The marker is thus highly predictive for mature fruit color.

Figure 8:
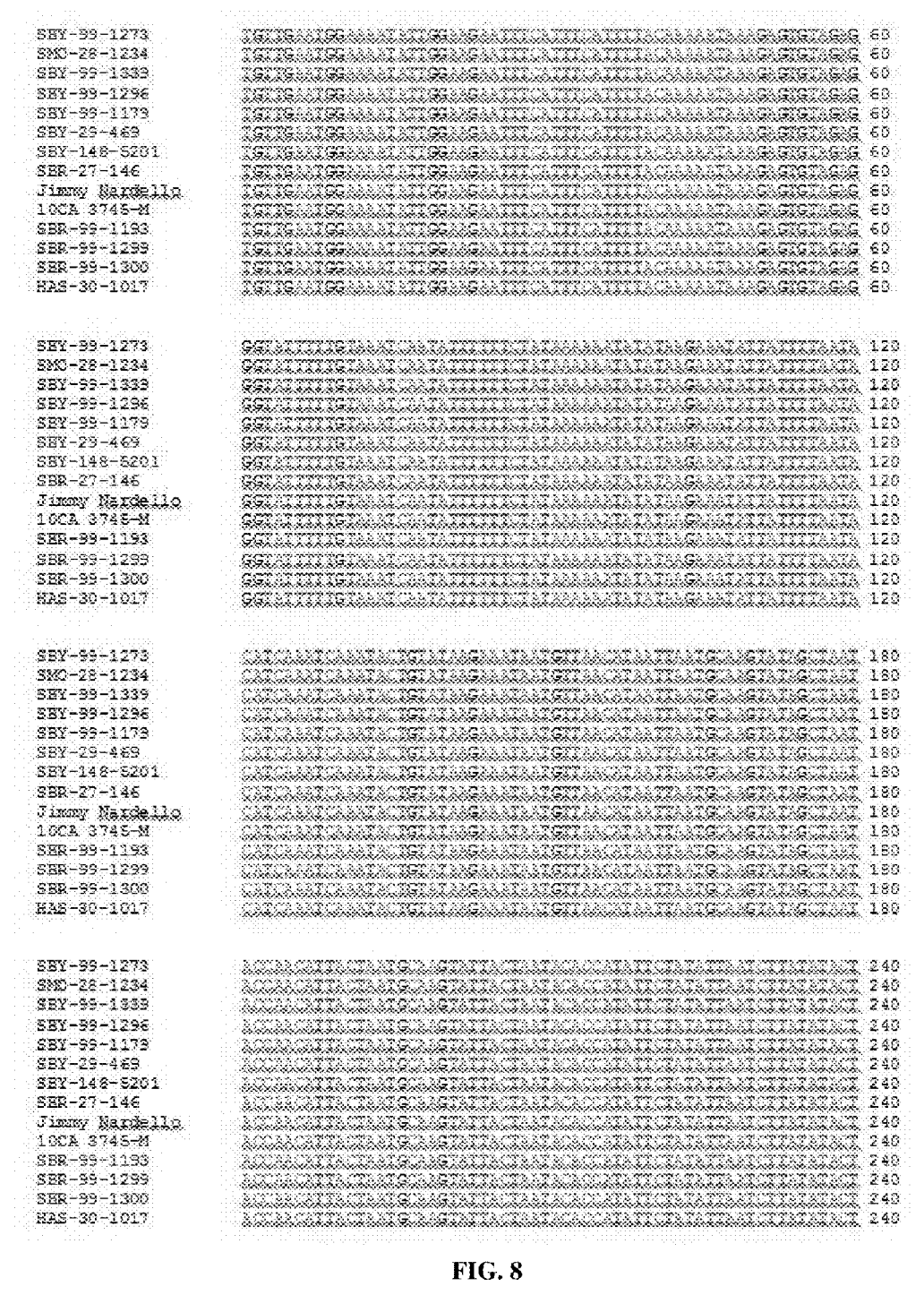
Figure 8:
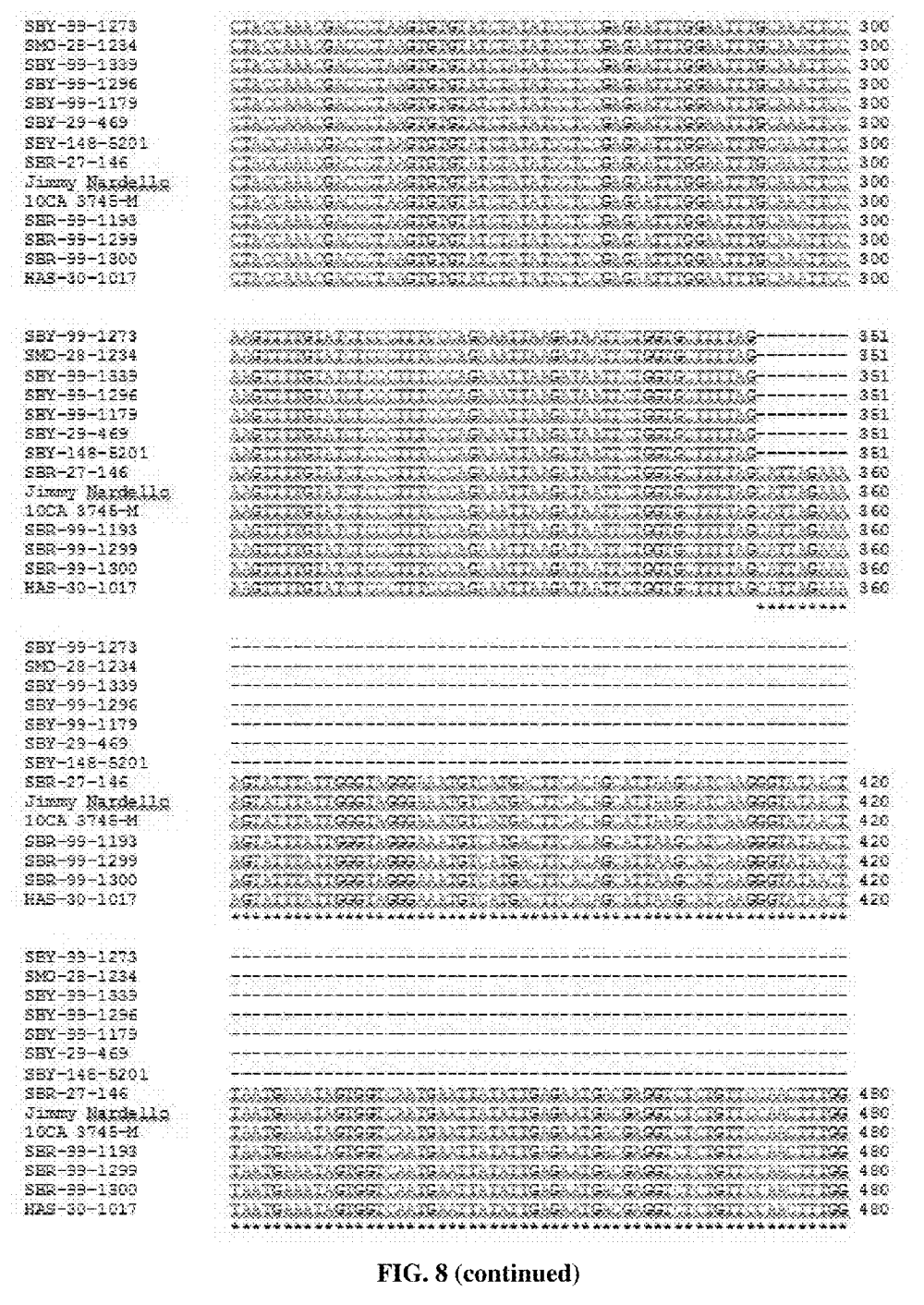
Figure 8:
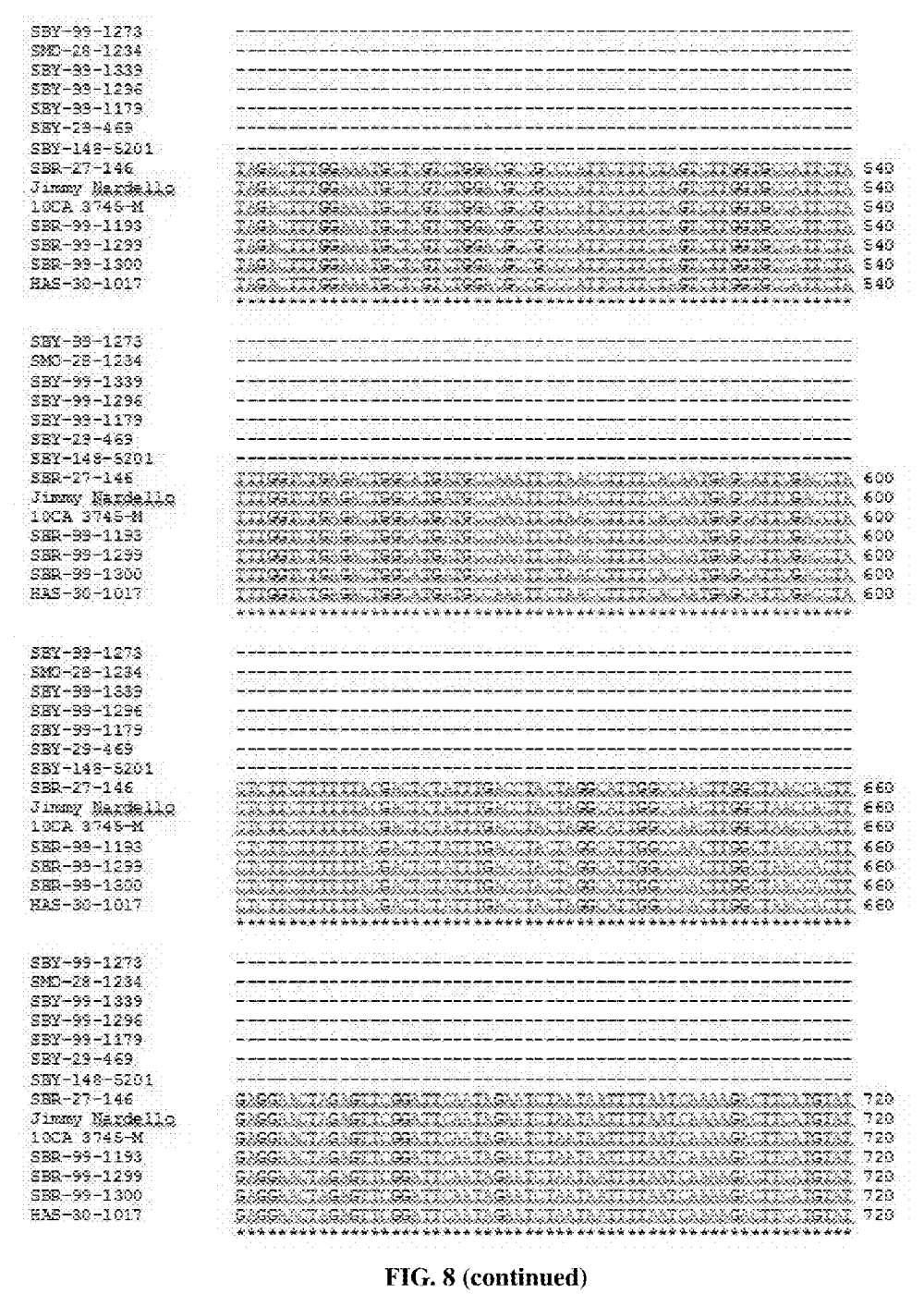
Figure 8:
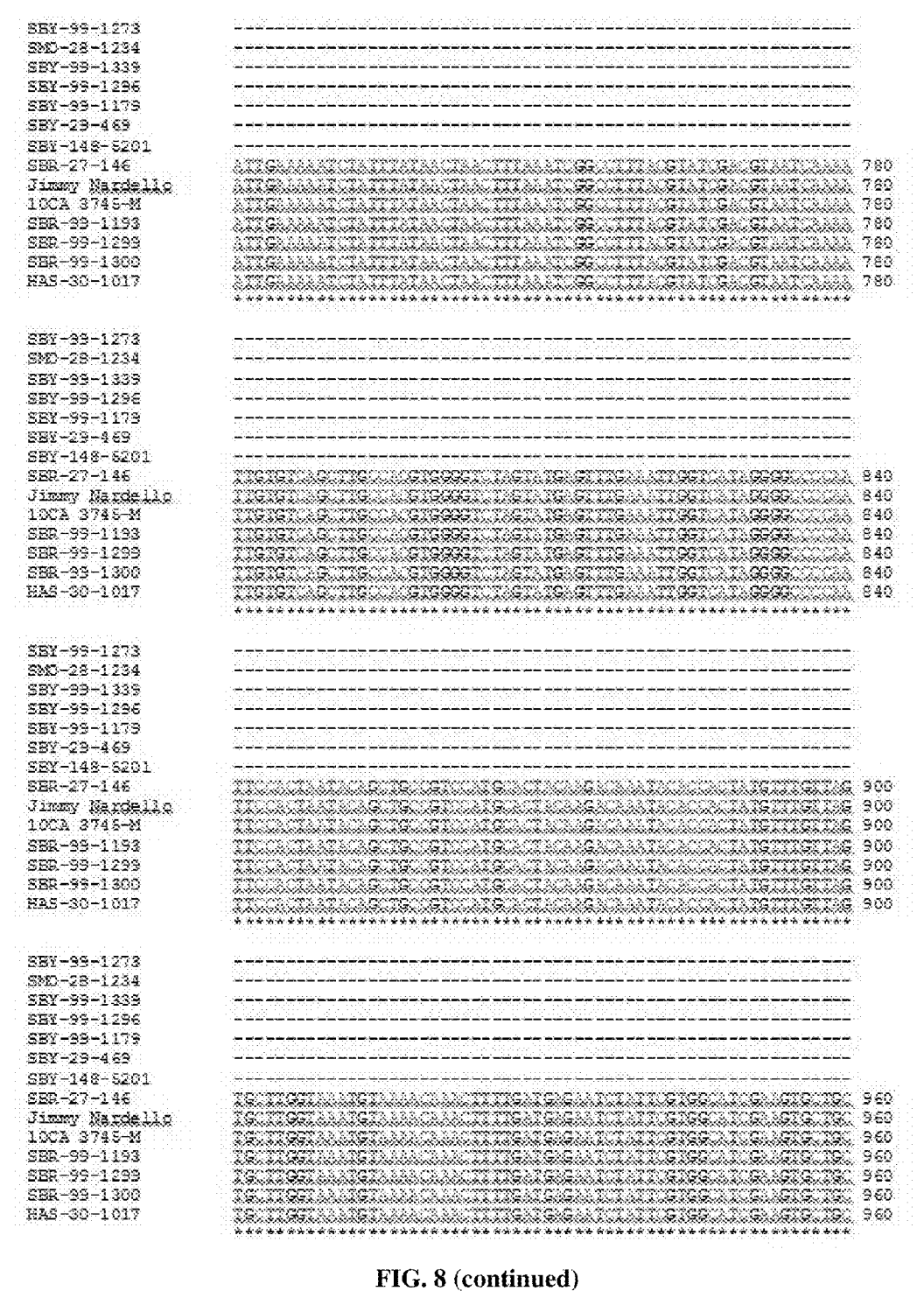
Figure 8:
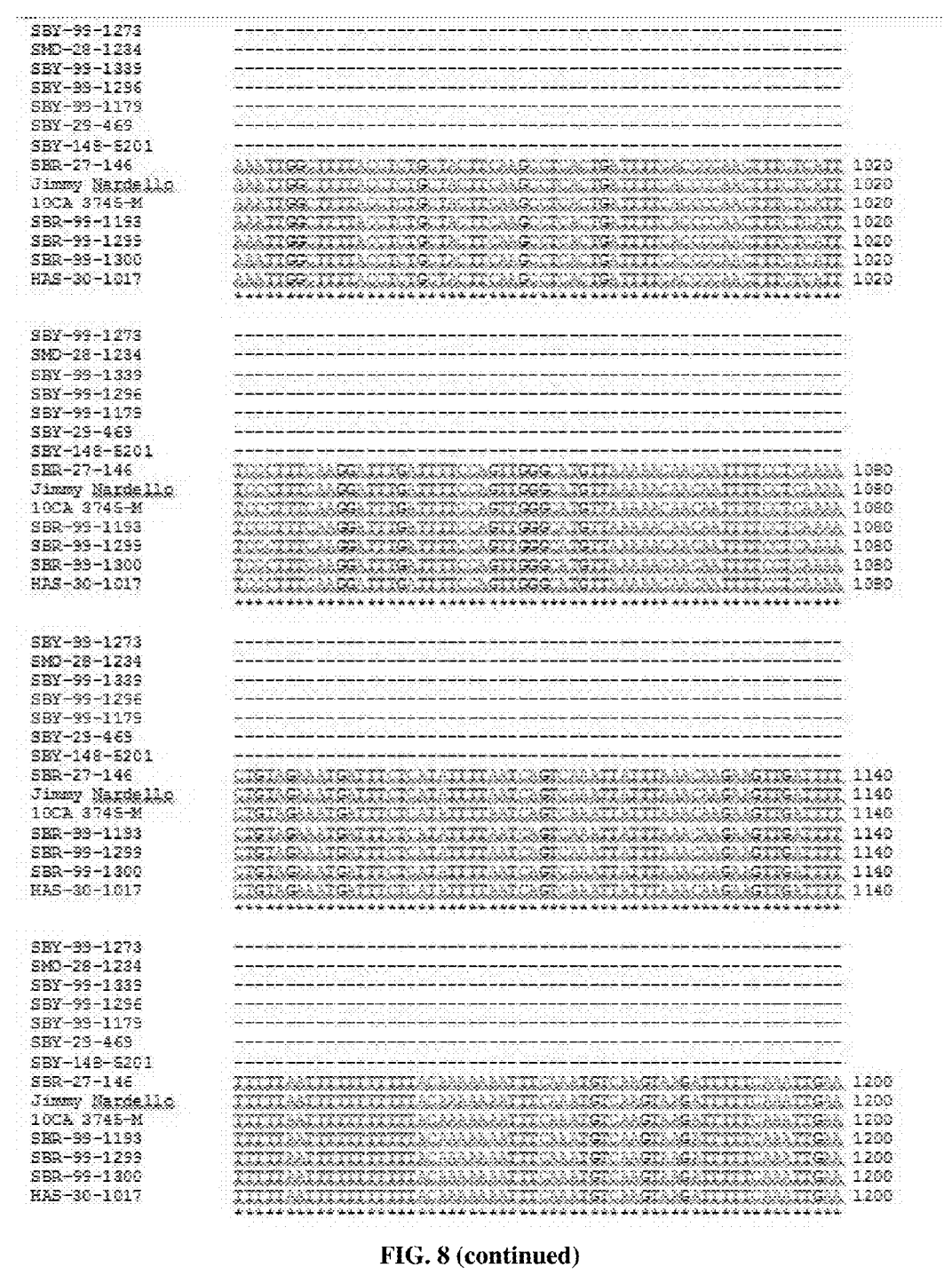
Figure 8:
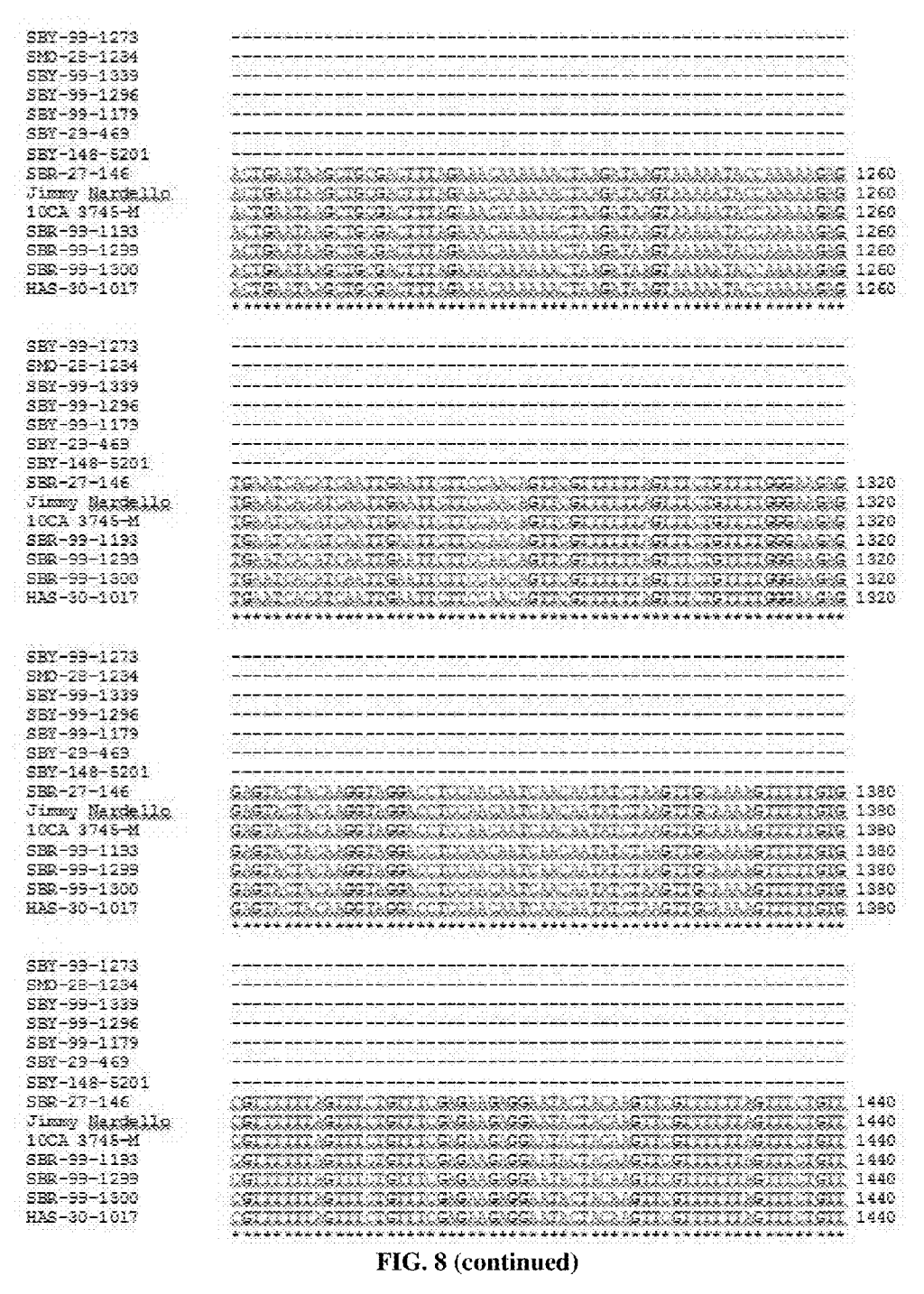
Figure 8:
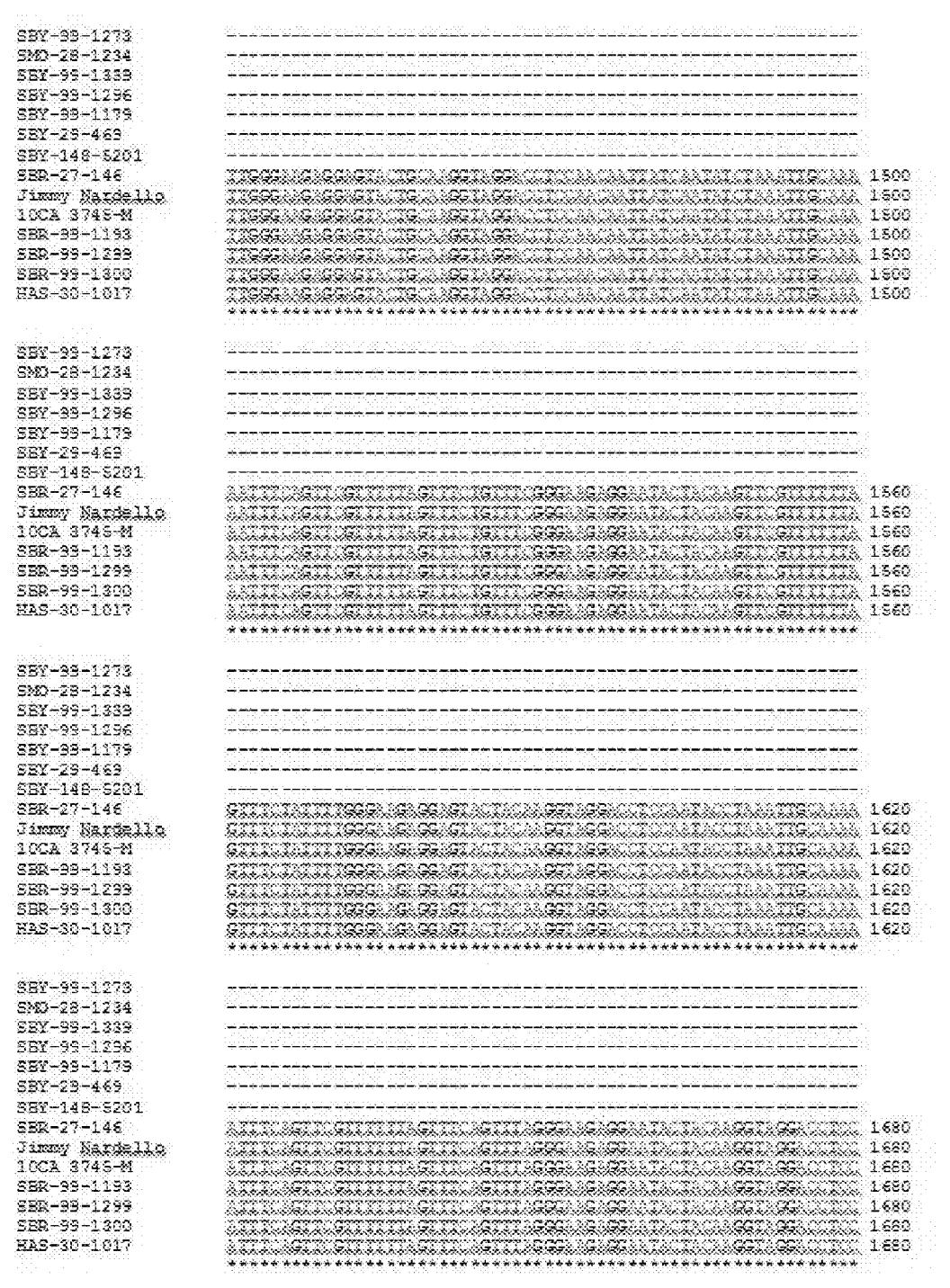
Figure 8:
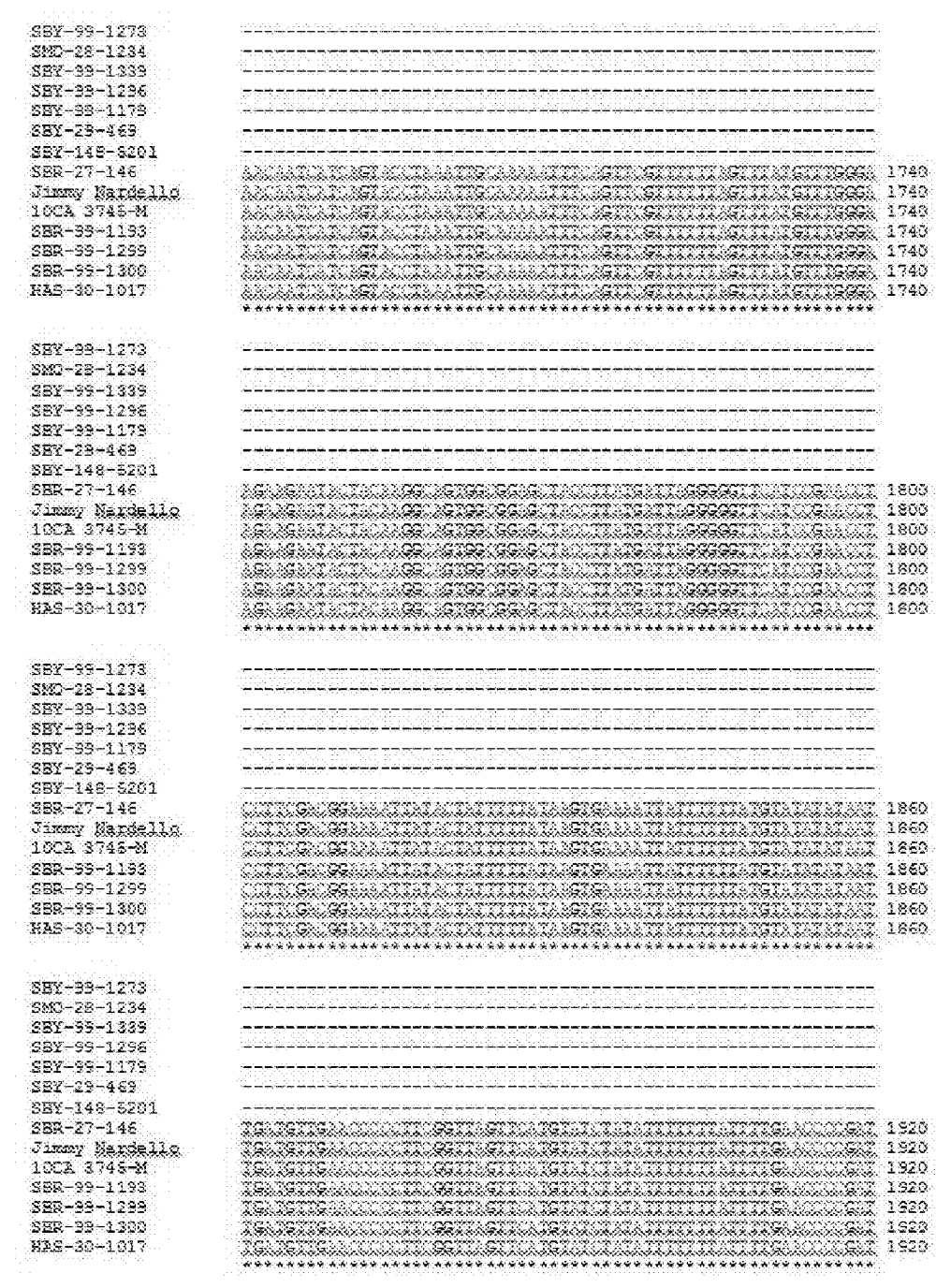
Figure 8:
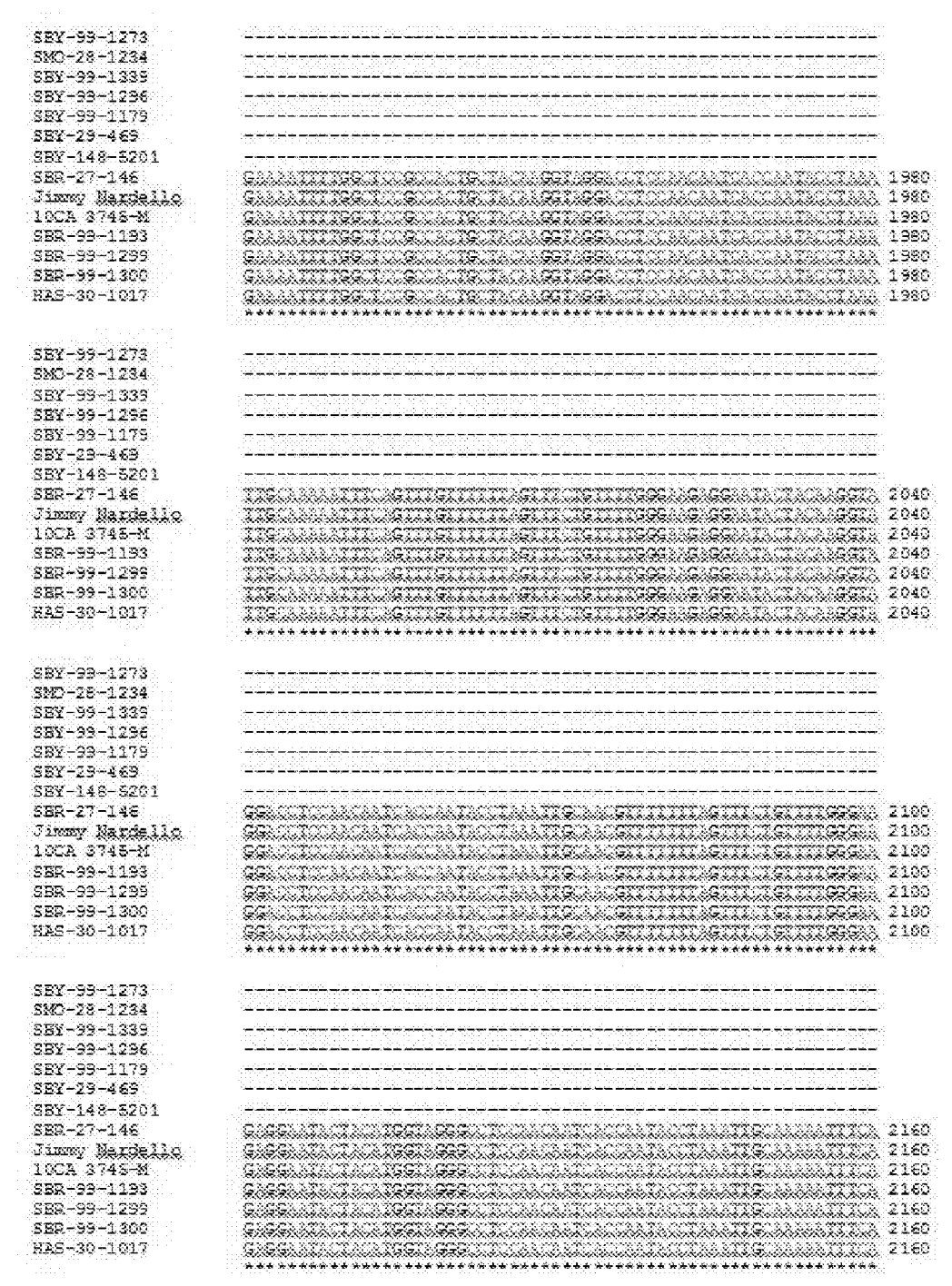
Figure 8:
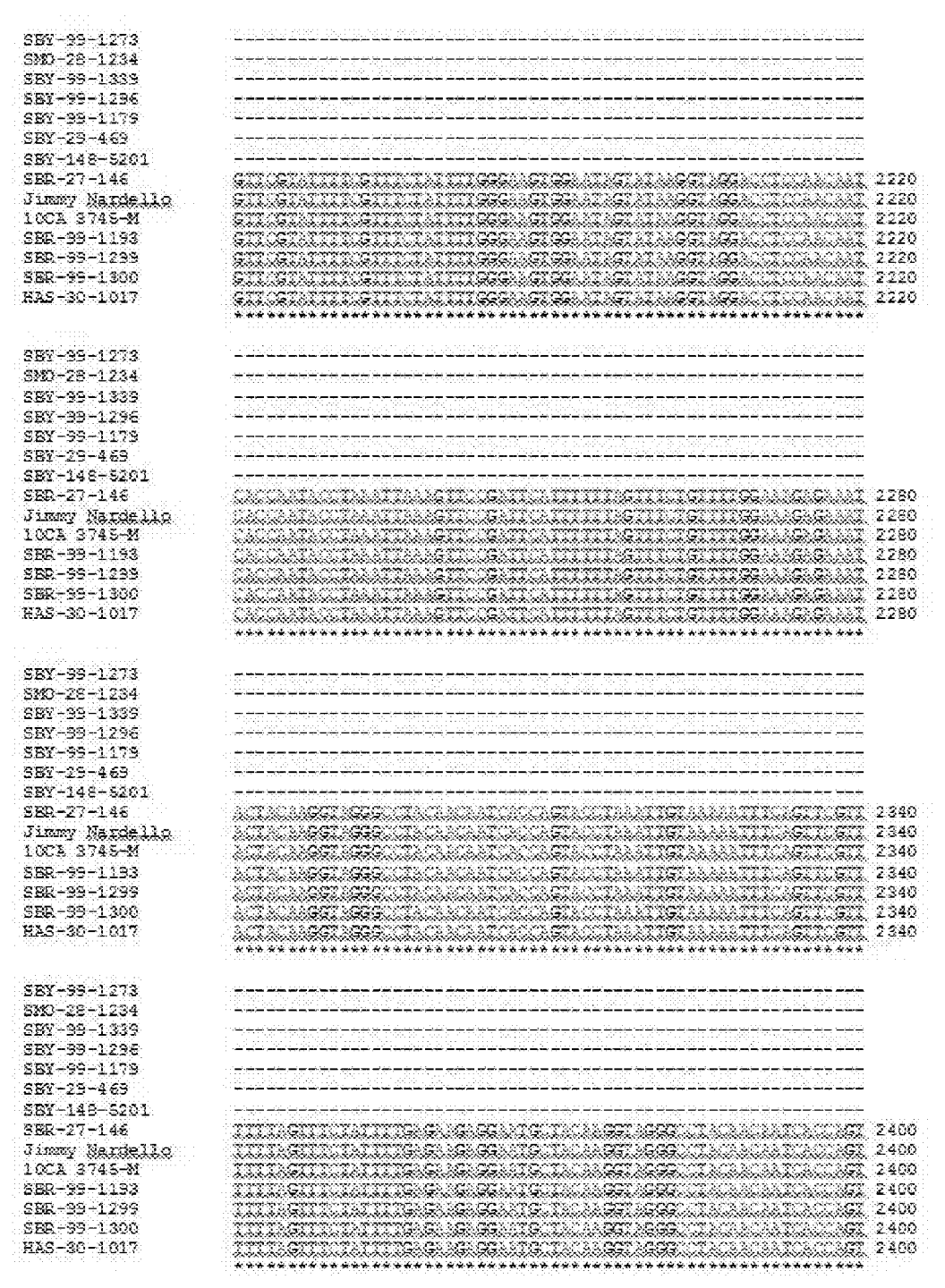
Figure 8:
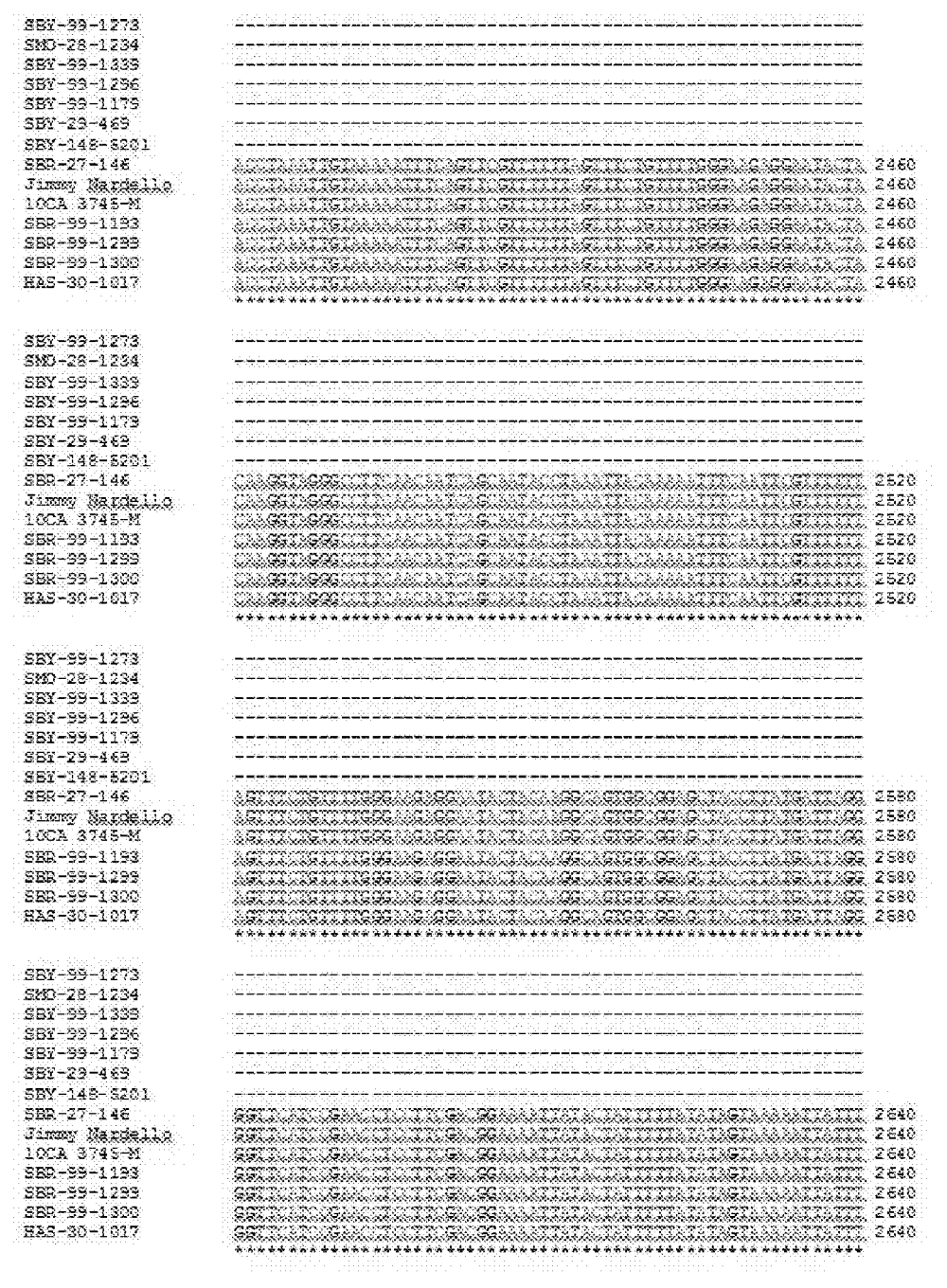
Figure 8:
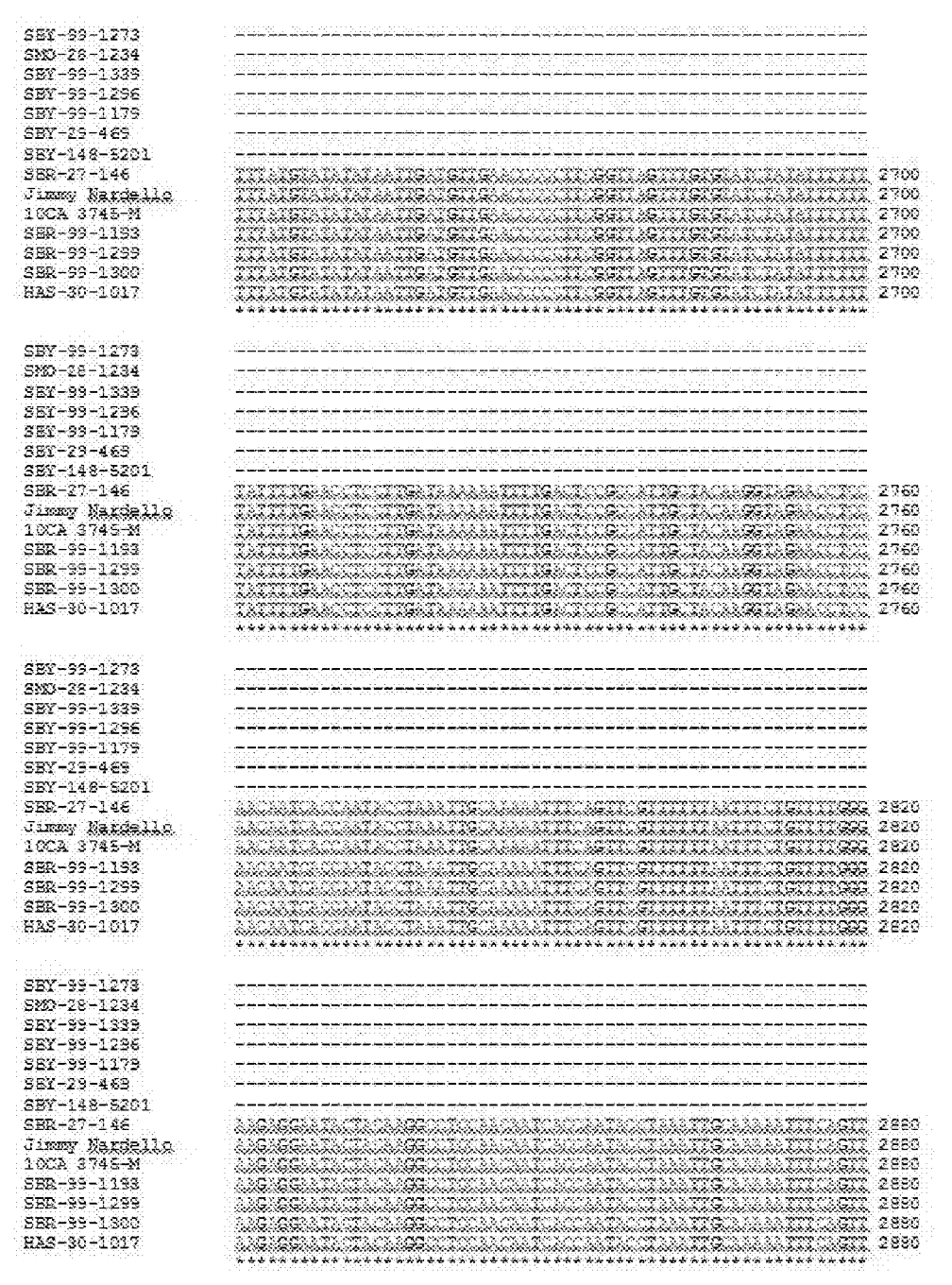
Figure 8:
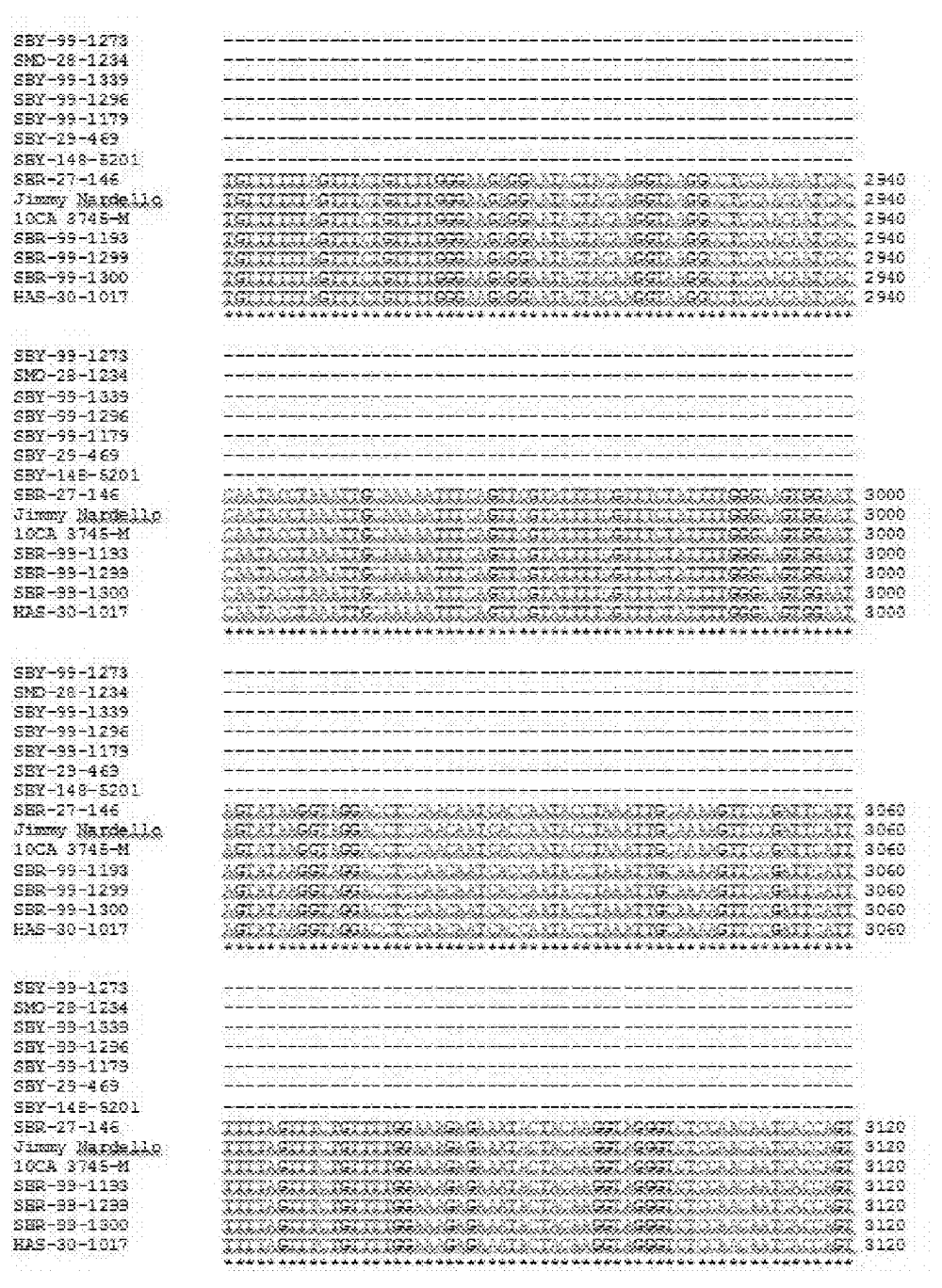
Figure 8:
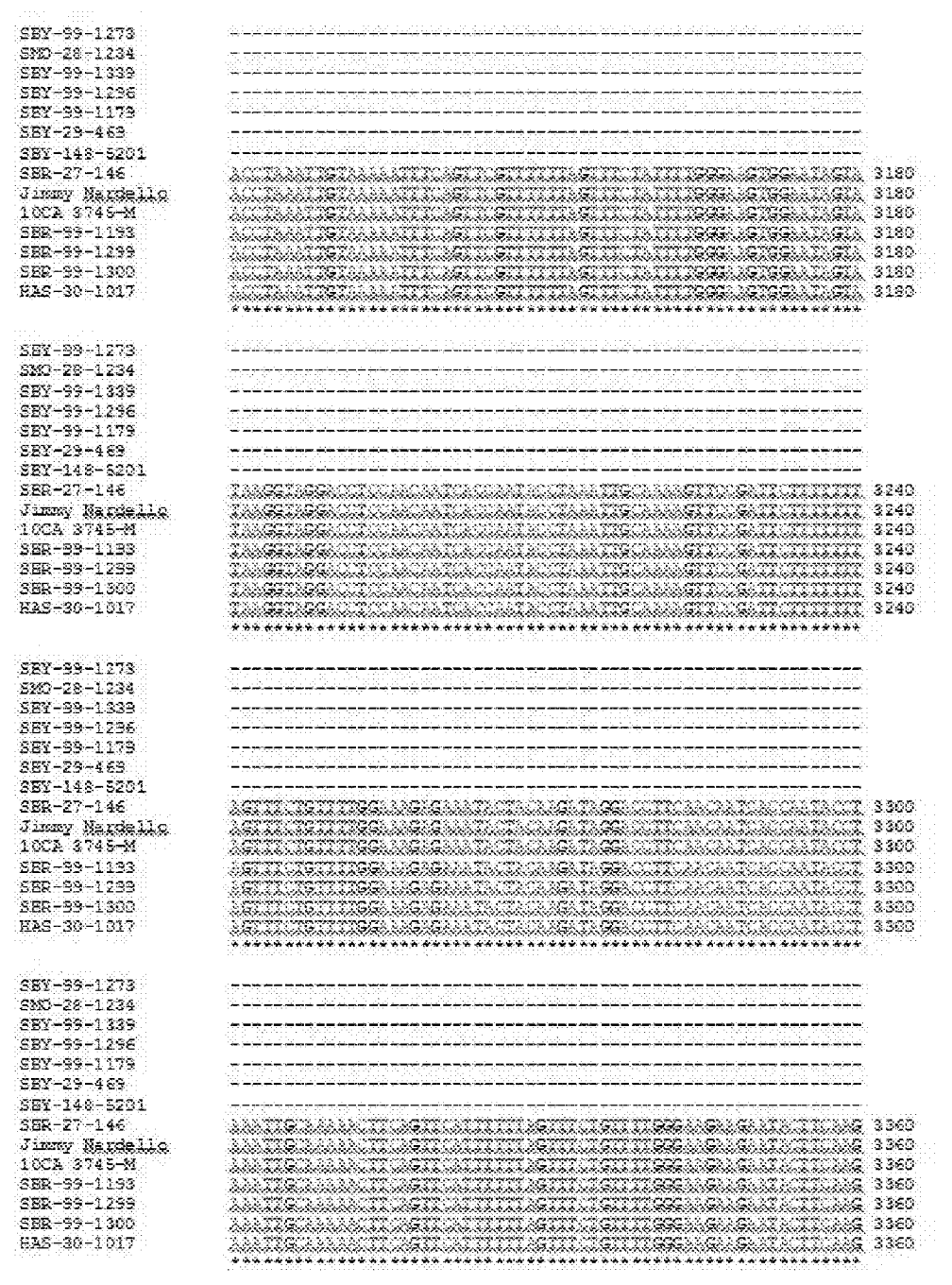
Figure 8:
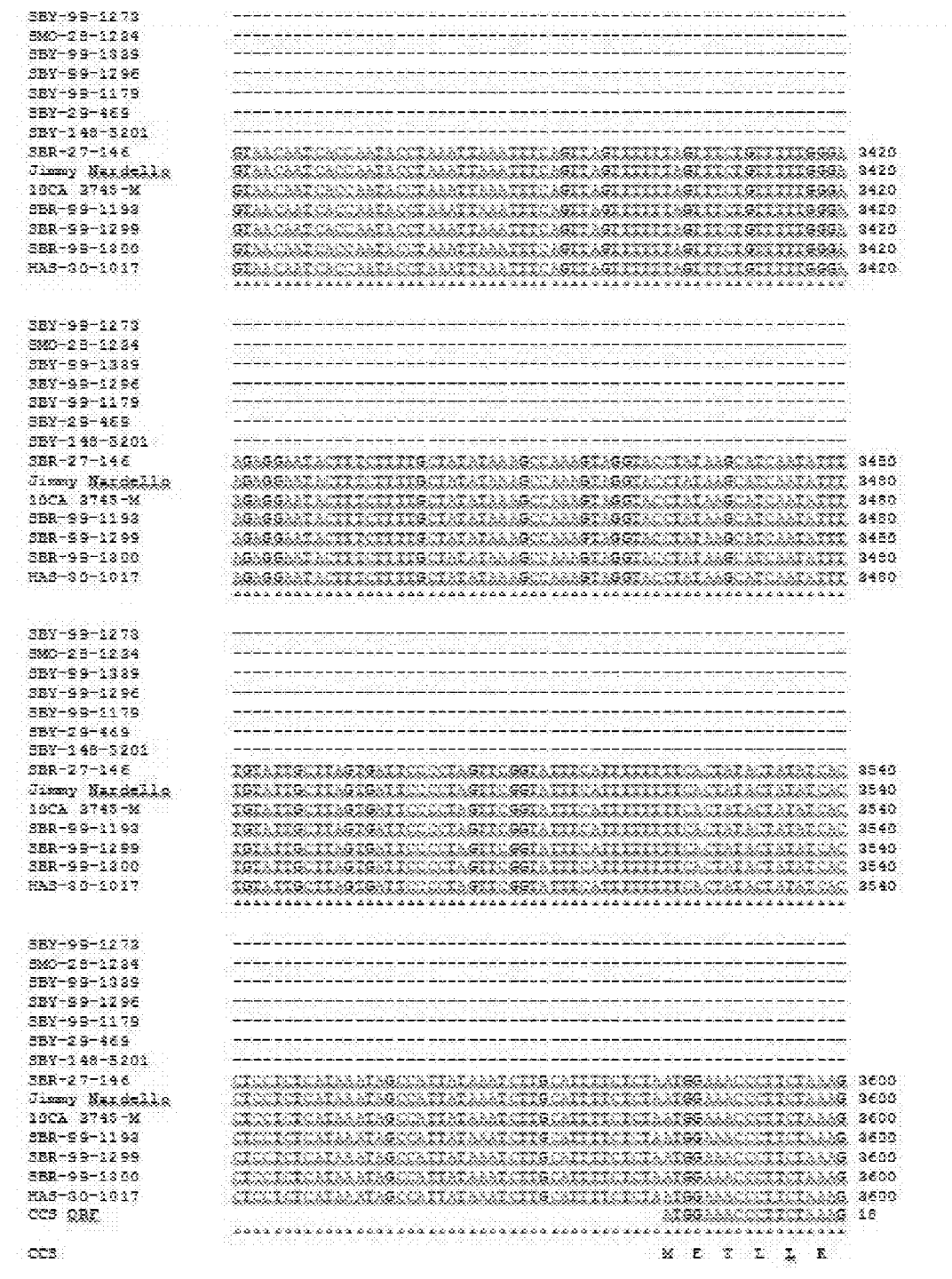
Figure 8:
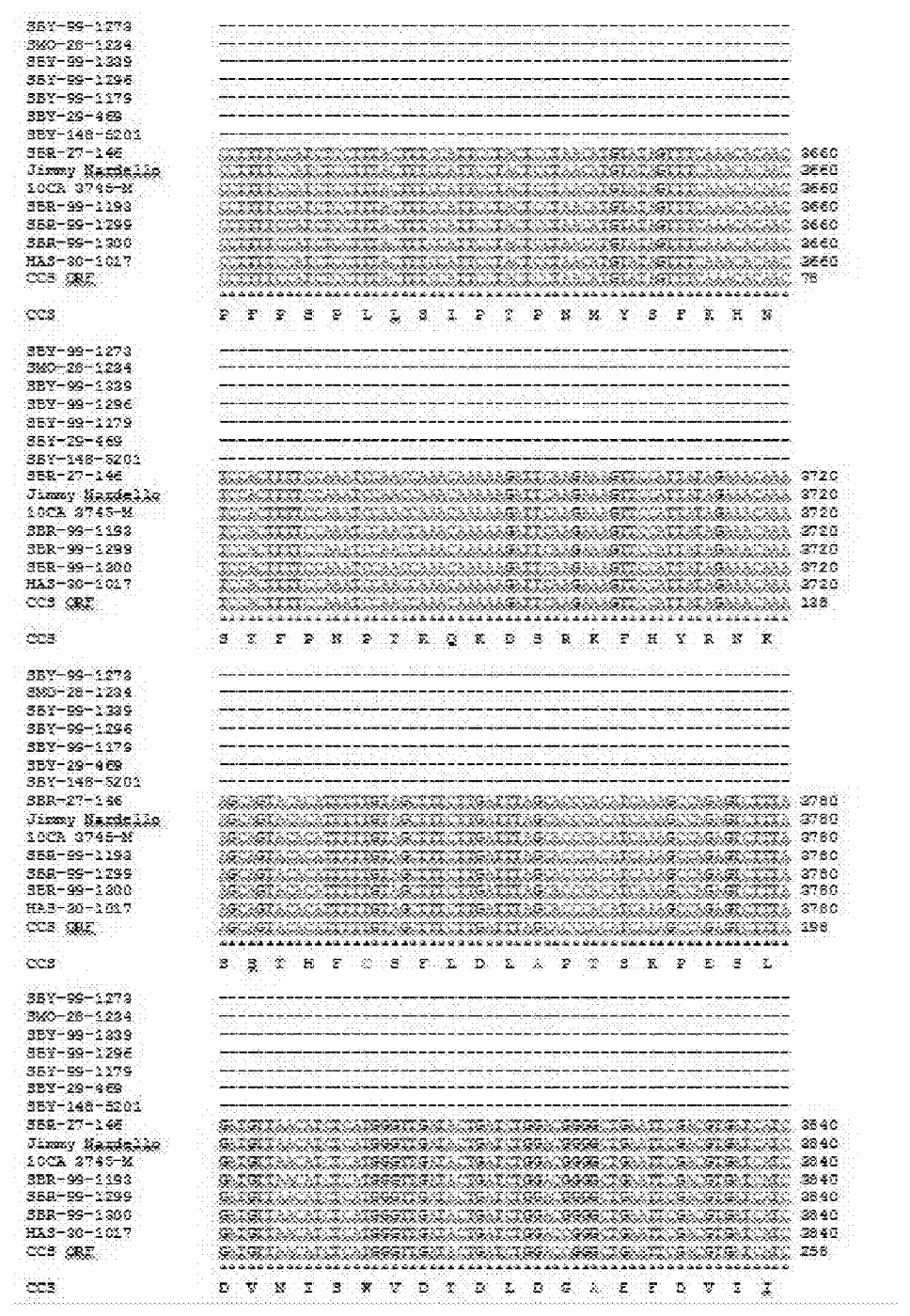
Figure 8:
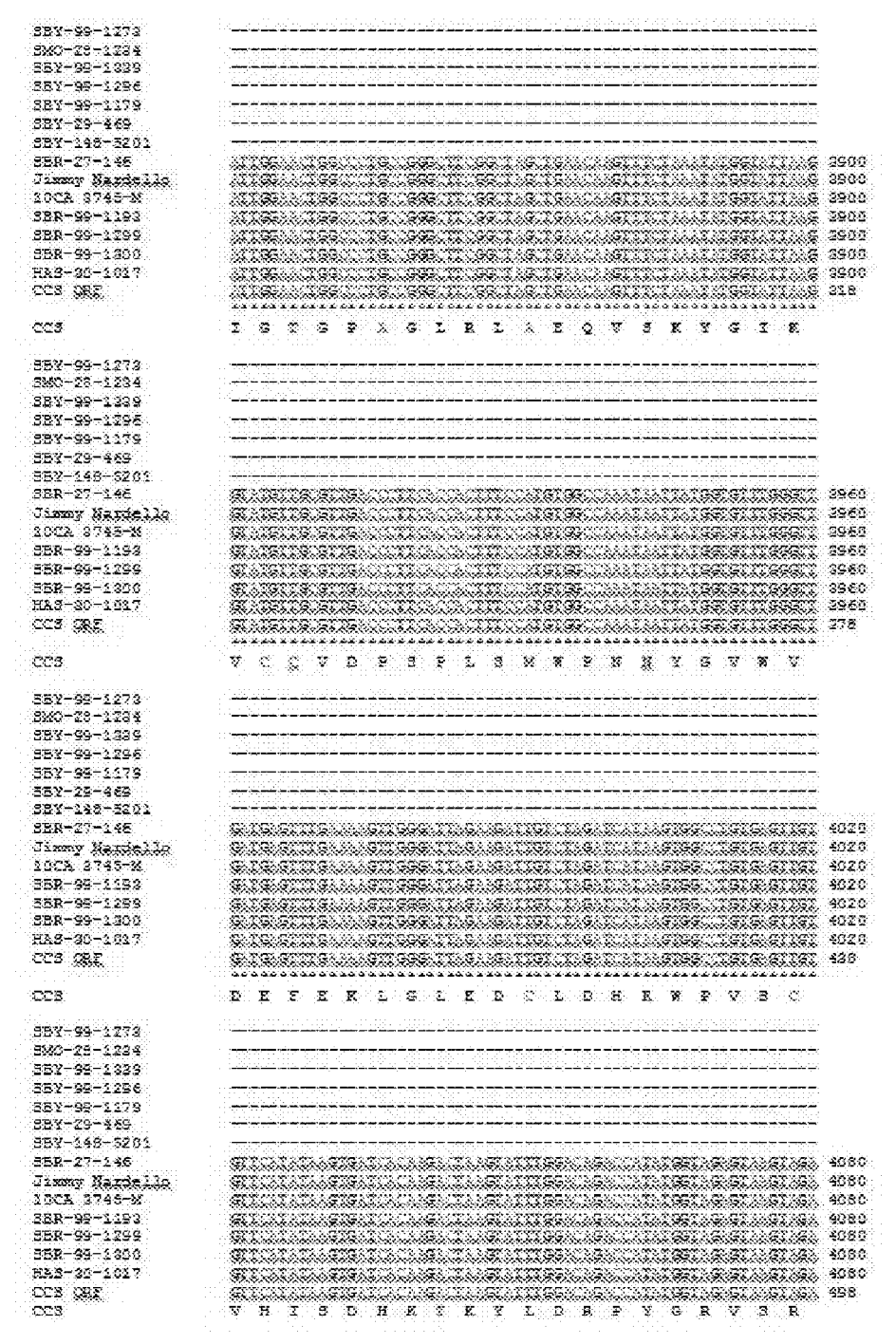
Figure 8:
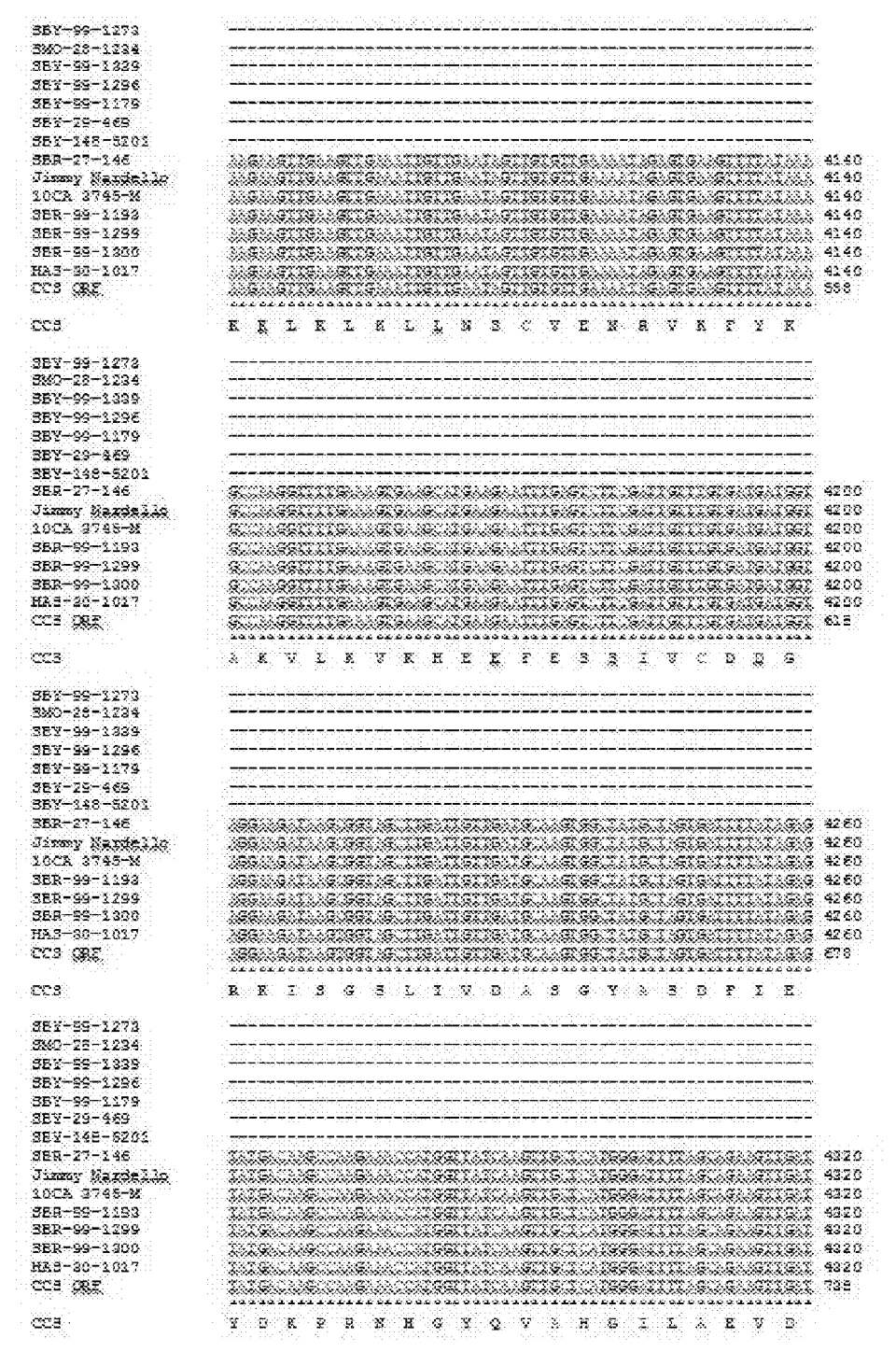
Figure 8:
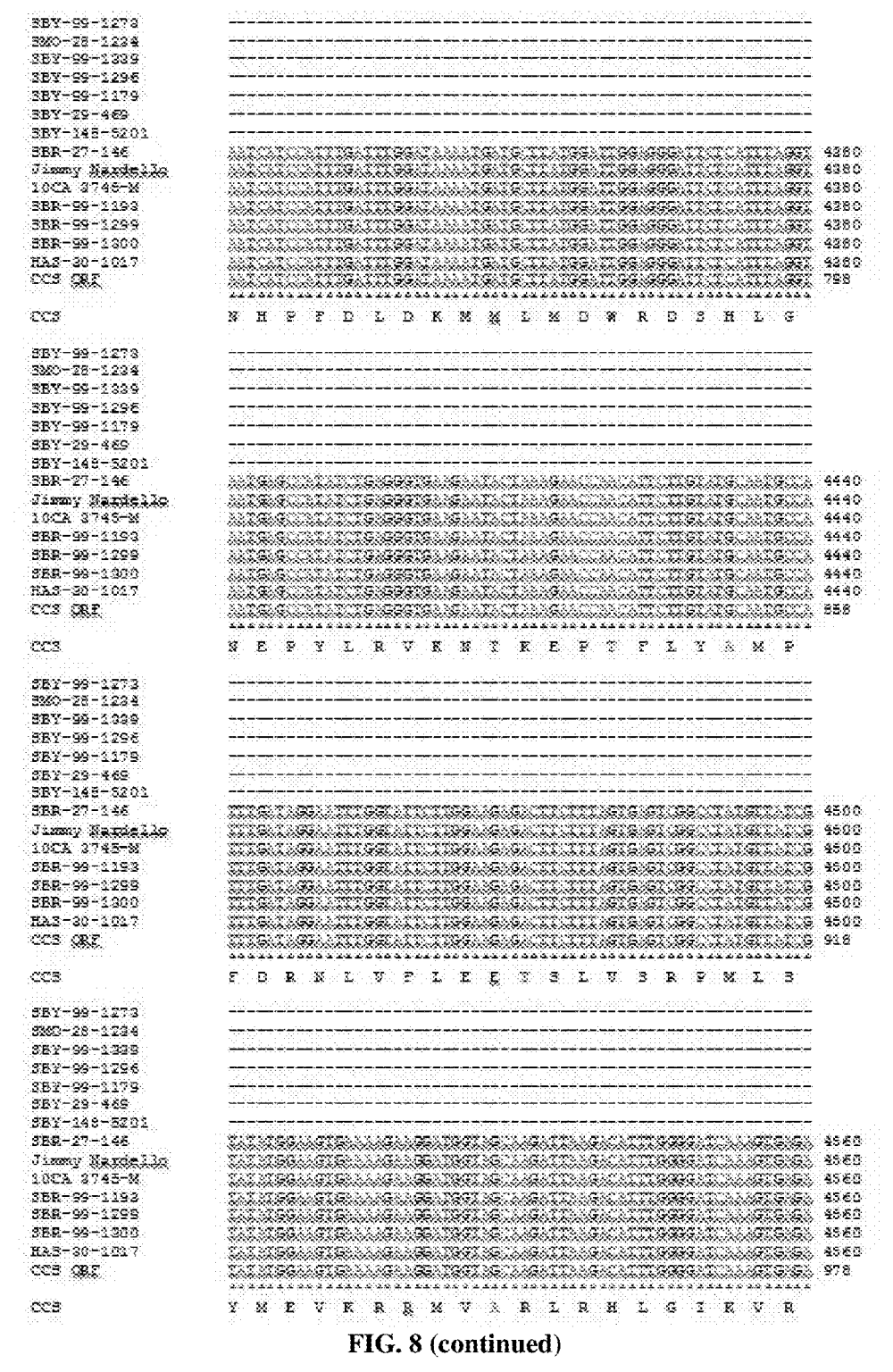
Figure 8:
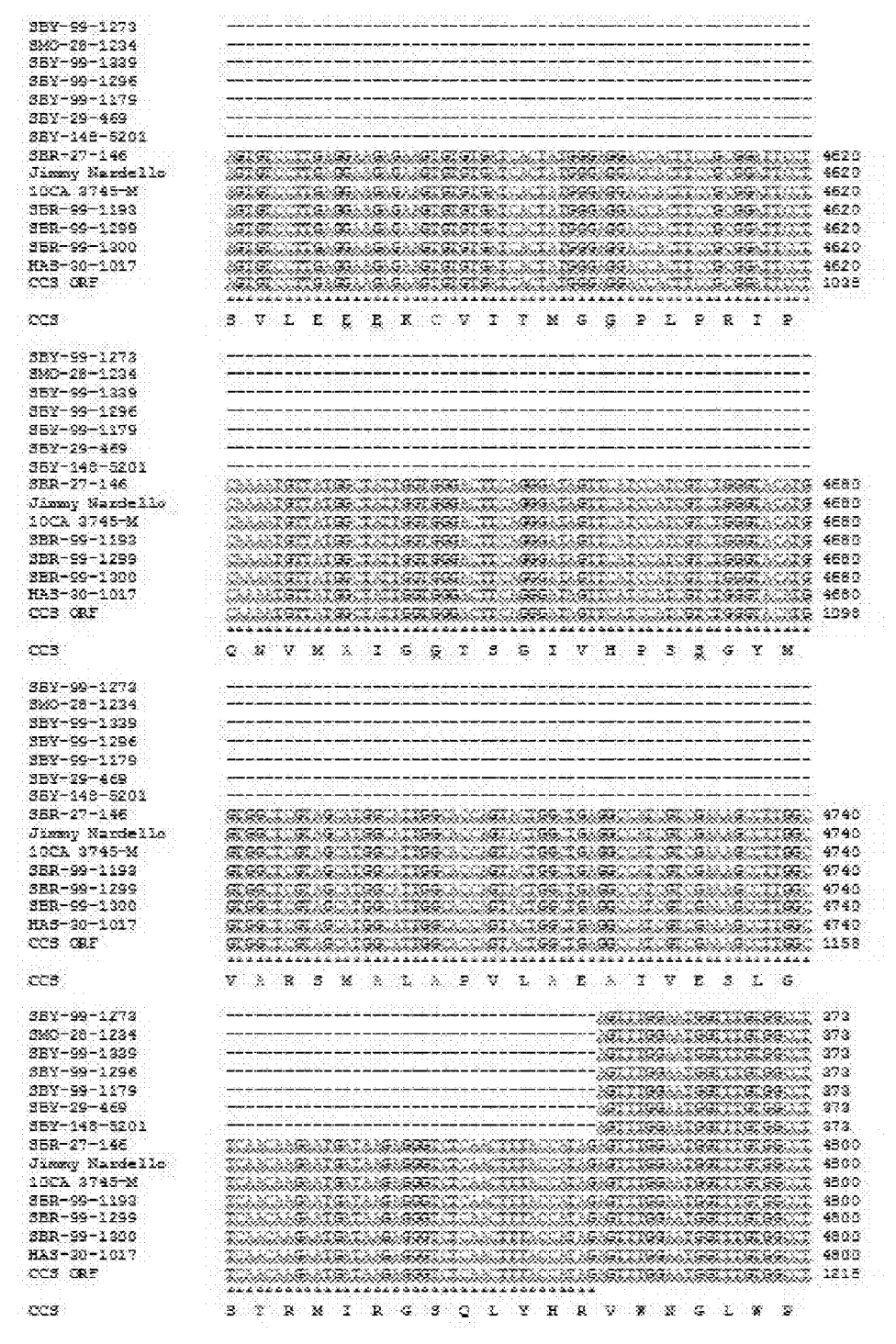
Figure 8:
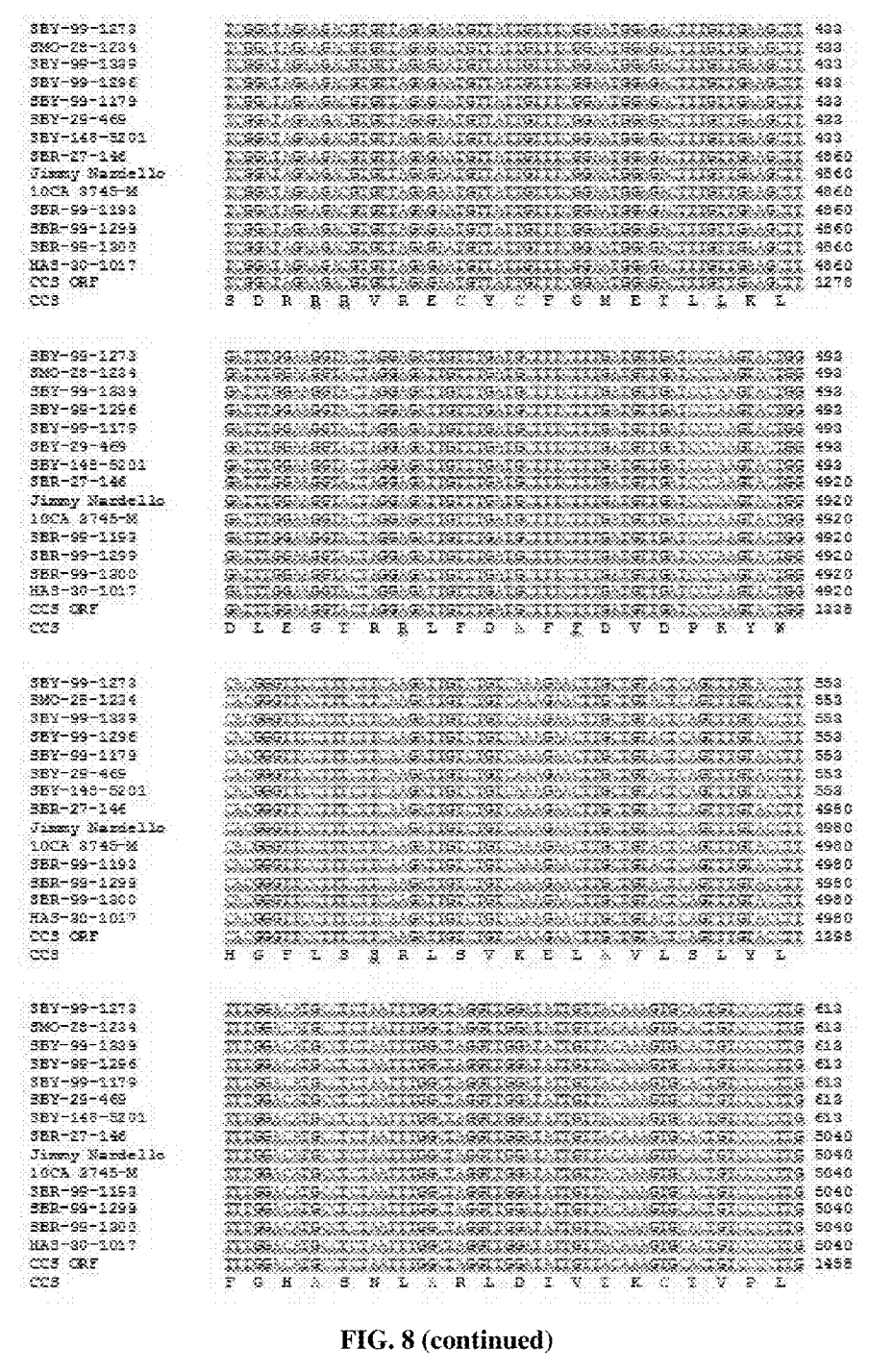
Figure 8:
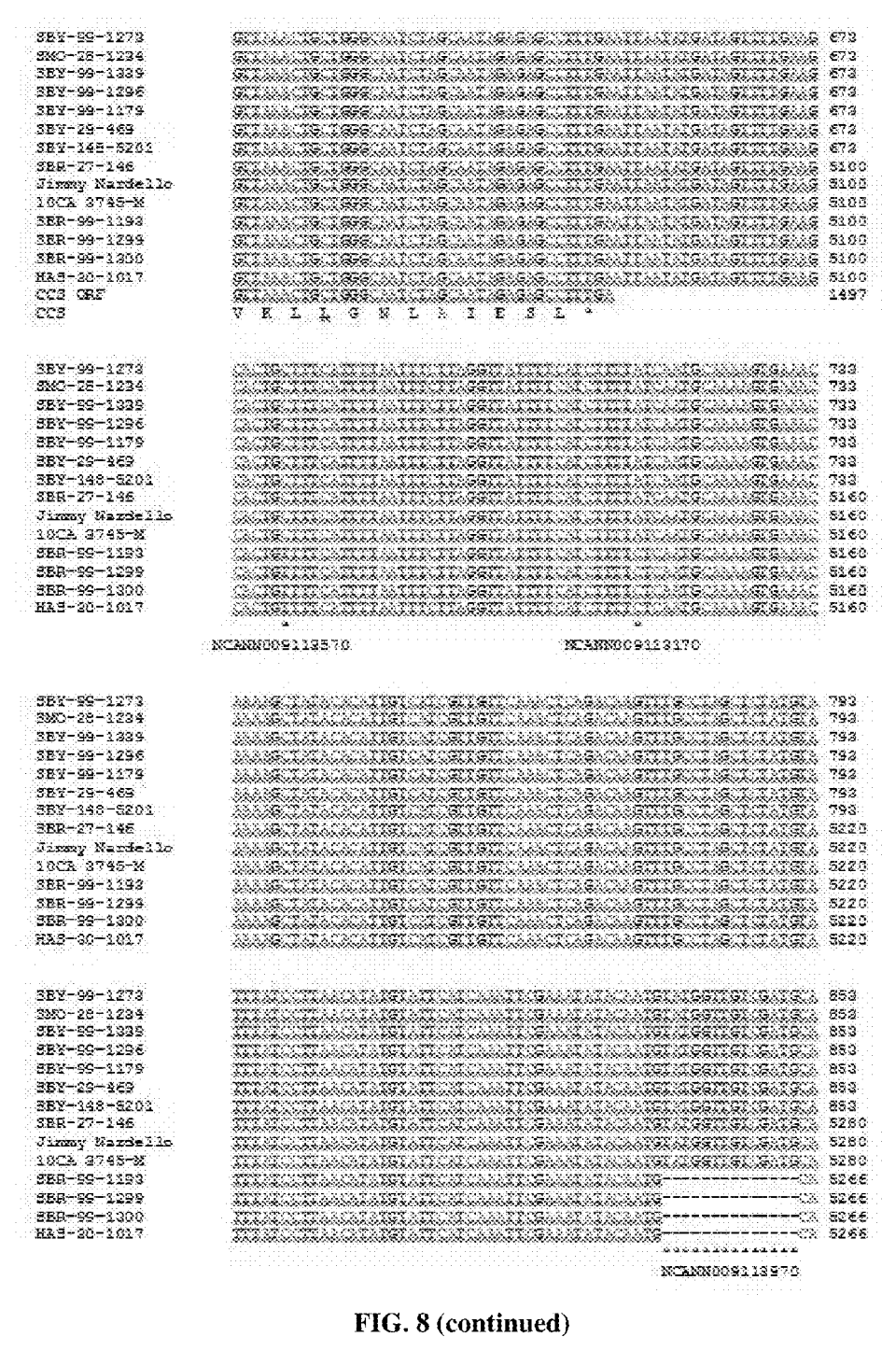
Figure 8:
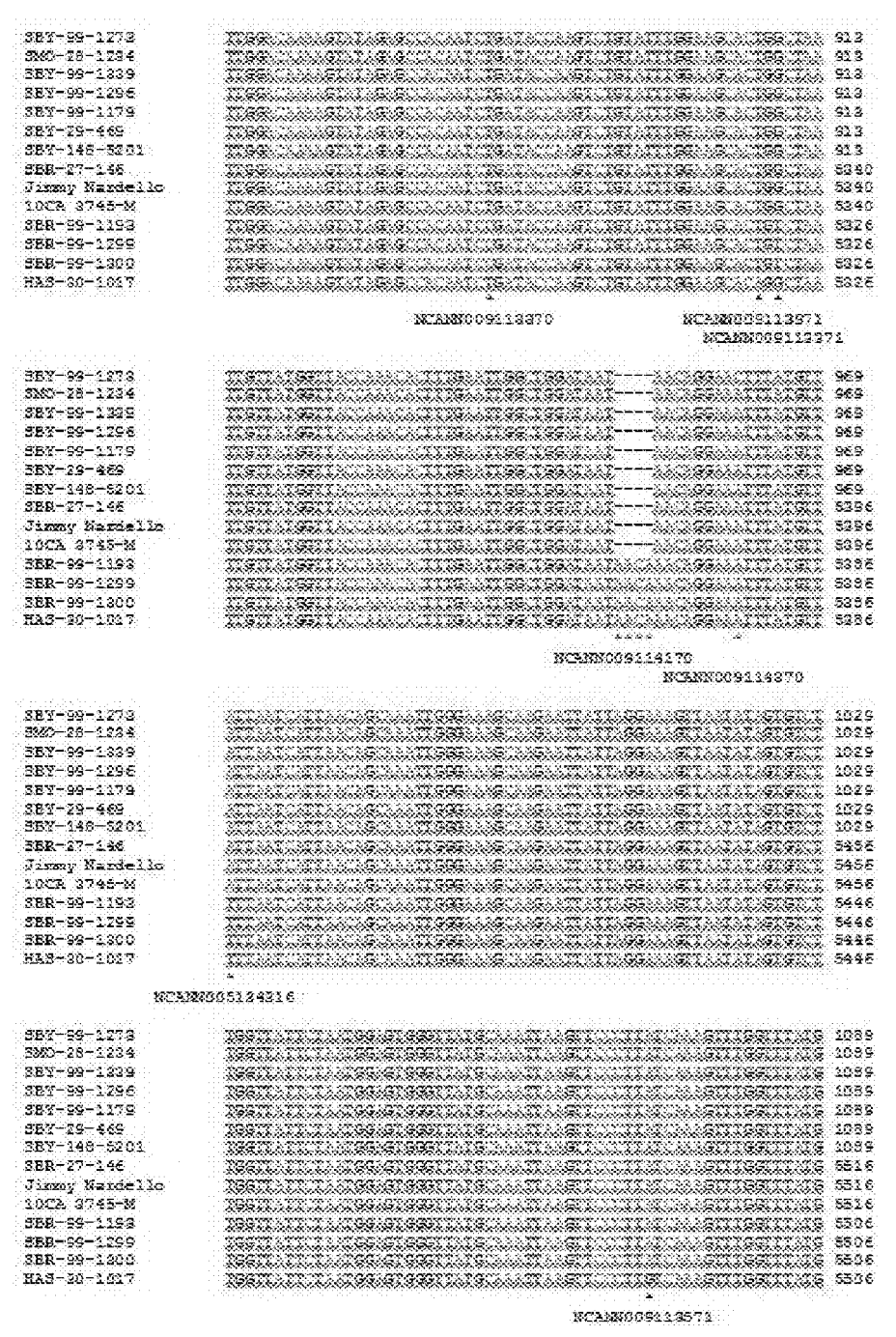
Figure 8:
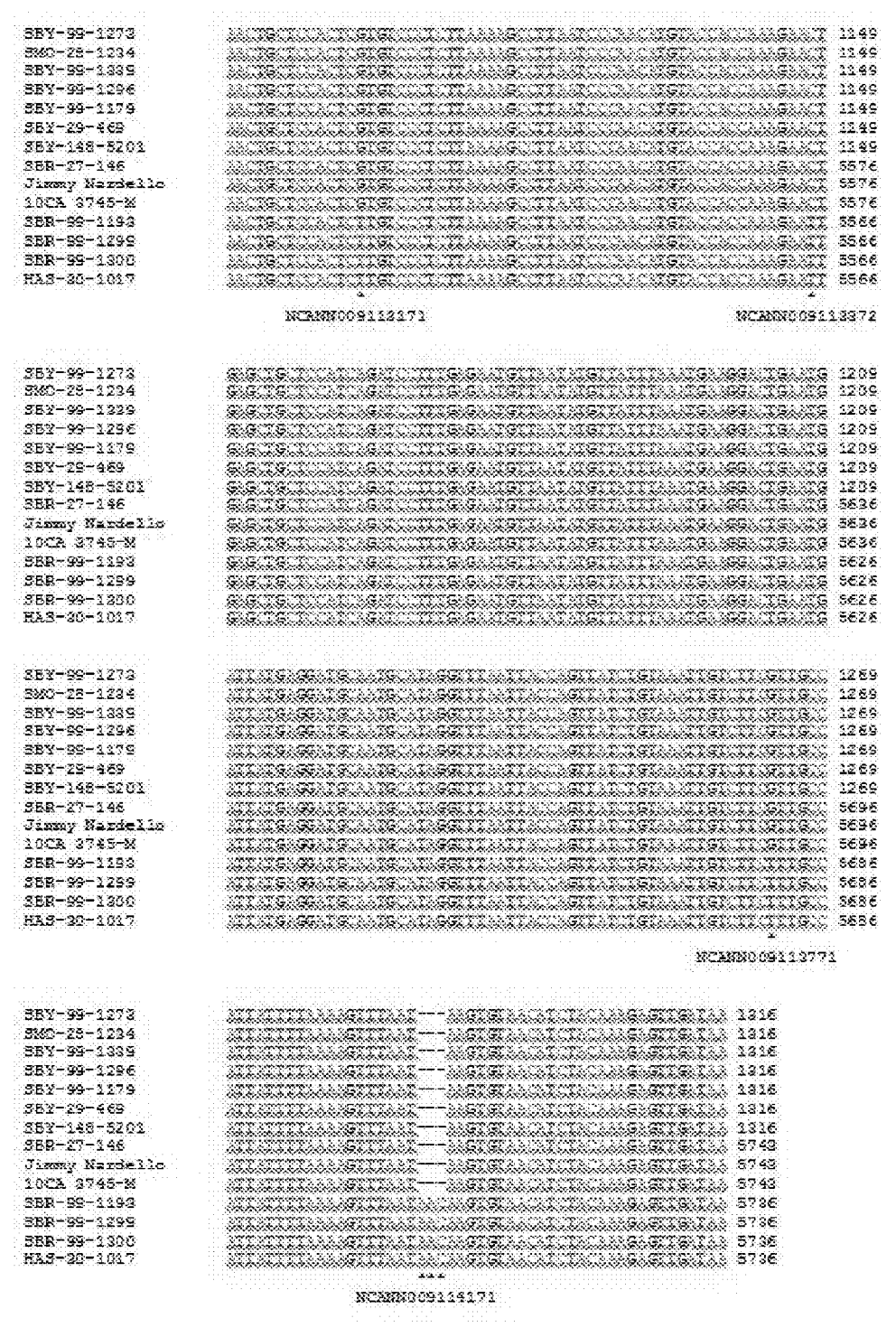

FIG. 8 gives an alignment of Ccs sequences from 14 pepper lines (SEQ ID NOs:40-53) showing the location of polymorphisms. A consensus CCS ORF sequence is given at SEQ ID NO:54. SNPs are indicated by asterisks. The predicted protein sequence of CCS is given at SEQ ID NO:55.

Of additional note is the discovery that plants can survive without a functional CCS gene. It follows that other mutations in the gene also may result in non-red fruit. An altered CCS genotype may therefore be provided by any suitable means; for example, EMS, MMS, other mutagen-derived, in situ-derived, or naturally-occurring mutations can provide an altered CCS genotype suitable for the development of the fruit color phenotypes described here. Color modulation of the fruit color phenotypes described here may also be achieved by transient disruption of CCS function at the time of fruit set and/or fruit color maturation.

Example 2

Zeaxanthin Epoxidase (Ze) Marker Development

The Zeaxanthin Epoxidase (Ze or ZEP hereafter) gene (Genbank X91491; SEQ ID NO:56) regulates the conversion of zeaxanthin to the yellow pigments antheraxanthin and violaxanthin. The gene is mapped to the lower part of chromosome 2 in pepper (Thorup et al. 2000) and the yellow-orange color polymorphism (YO_color) locus maps to the same region of chromosome 2. Map positions were derived from a linkage analysis study of an F2:F3 population (from a cross between a yellow line and an orange line) to arrive at a rough map position of 100.8 cM for the yellow-orange color locus (Tables 6-7).

TABLE 6

Map position of YO_color locus using an F2:F3 bi-parental mapping population. Nucleotide sequences around listed markers are given in SEQ ID NOs: 57-62.

| Marker | Chromosome | SBY-29-469/SMO-28-1234 F2:F3 | Map position (cM) |
|---|---|---|---|
| NE0235373 | 2 | 0 | 88.9 |
| NE0240266 | 2 | 2.9 | 94.2 |
| NE0237869 | 2 | n/a | 95.0 |
| YO_color* | 2 | 16.6 | 100.8 |
| NE0239621 | 2 | 22.4 | 103.6 |
| NE0240354 | 2 | 34.8 | 111.7 |
| NE0241248 | 2 | 37.1 | 113.6 |

*Yellow (Y) vs. orange (O) color scored as a binary trait in F3 families to permit inference of all three genotypic classes in the F2 generation.

TABLE 7

Primers and probes used for TaqMan™ assays with markers of Table 6 (SEQ ID NOs: 63-86).

| Marker | Position | Primer or probe name | Sequence | Allele |
|---|---|---|---|---|
| NE0235373 | 88.9 | NE0235373_F | CGTAAATTGTAGTCCTTGCCTCAGT | |
| | | NE0235373_R | GGACAAGGGAGGAAGTTGAATCTAA | |
| | | NE0235373_V | CTCTATTGACAAGAAACAA | T |
| | | NE0235373_M | CTATTGACAGGAAACAA | C |
| NE0240266 | 94.2 | NE0240266_F | CTGGTCCAACTCTACATGTACGT | |
| | | NE0240266_R | CCAATGGATAGTGAGATCGTATGGTAATT | |
| | | NE0240266_V | AGGGCGACACCATTGT | A |
| | | NE0240266_M | AGGGCGACACCCTTGT | C |
| NE0238769 | 95.0 | NE0238769_F | CAATCAATCAACAAGGACAAACCAATGA | |
| | | NE0238769_R | CTAGAGTATTACATTCTTTTGCCAAGGGA | |
| | | NE0238769_V | ATCTTGGATAGTACAGCTGTAT | C |
| | | NE0238769_M | ATCTTGGATAGTACAACTGTAT | T |
| NE0239621 | 103.6 | NE0239621_F | GTACTTTTTGTCTTGTTGGACCAATCC | |
| | | NE0239621_R | ACCATGTTGCAGTCAATACGTACA | |
| | | NE0239621_V | CCCCCTCCAATGTAAA | T |
| | | NE0239621_M | CCCCCTCCAGTGTAAA | C |
| NE0240354 | 111.7 | NE0240354_F | TCAGTTATATTAAAGAAAATGTATGATAAATAGCA | |
| | | NE0240354_R | GCAGTAAATGGATATATTATACGCAAAAGCA | |
| | | NE0240354_V | ATGTGTTGGTGTTGTATAA | A |
| | | NE0240354_M | ATGTGTTGGTGATGTATAA | T |
| NE0241248 | 113.6 | NE0241248_F | GTTGTTCCCTGCTCTTGCTGTA | |
| | | NE0241248_R | CACCGGCCAAGATTCCTCAA | |
| | | NE0241248_V | CCTGTGTTGTGTTGTTGT | T |
| | | NE0241248_M | CTGTGTTGTGCTGTTGT | C |

Association mapping provided additional evidence that the position on chromosome 2 is common across the relevant pepper germplasm. Data obtained from assaying 2,836 mapped SNPs from a total of 122 yellow and 17 orange lines of the sweet blocky, sweet mini, and sweet long fruit types was used in a case-control association analysis implemented in PLINK. The strongest association between yellow-vs. orange color and a mapped SNP was detected for NE0238769 at position 95.04 cM on chromosome 2.

Figure 4:
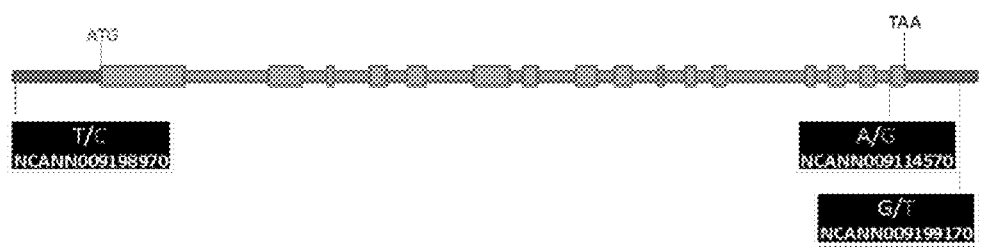
FIG. 4: The genomic structure of the Ze gene. Boxes set into top line represent coding regions (exons); other portions of the top line represent introns, and regions upstream of the ATG and downstream of the TAA represent the UTR. The start codon (ATG indicated on top line) and stop codon (TAA on top line) are also indicated, while the three identified SNPs are indicated on the bottom of the figure.

Only cDNA sequence was available for the *C. annuum* Ze gene in the public domain (Genbank X91491), and no SNPs were known to have been described in the coding sequence of the gene. Analysis of initial efforts to sequence the genomic gene sequence led to the conclusion that it was rich in introns (now known to be 15 introns in total) and extensive re-sequencing of genomic DNA was required to obtain the full sequence (introns and exons). In total 4803 bp were sequenced. The coding sequence (SEQ ID NO:56) comprises 1971 bp, corresponding to a 656 AA protein. This differs from Genbank X91491, which is 1983 bp in length, corresponding to a 660 AA protein. The coding sequence of SEQ ID NO:56 is divided over 16 exons. The 15 introns comprise 2831 bp while in total 950 bp are obtained from the UTR (Table 8). In total 3 SNPs were identified between yellow and orange lines (Table 8). The complete genomic organization of the Ze gene is represented in FIG. 4.

TABLE 8

Sizes in bp of coding and non-coding sequences in the pepper Ze gene.

| Coding sequence | | Non-Coding sequence | |
|---|---|---|---|
| | | 5' UTR | 526 |
| exon 1 | 497 | intron 1 | 505 |
| exon 2 | 196 | intron 2 | 150 |
| exon 3 | 42 | intron 3 | 213 |
| exon 4 | 101 | intron 4 | 117 |
| exon 5 | 116 | intron 5 | 285 |
| exon 6 | 212 | intron 6 | 86 |
| exon 7 | 90 | intron 7 | 226 |
| exon 8 | 123 | intron 8 | 104 |
| exon 9 | 99 | intron 9 | 163 |
| exon 10 | 31 | intron 10 | 130 |
| exon 11 | 65 | intron 11 | 96 |

TABLE 8-continued

Sizes in bp of coding and non-coding sequences in the pepper Ze gene.

| Coding sequence | | Non-Coding sequence | |
| --- | --- | --- | --- |
| exon 12 | 86 | intron 12 | 480 |
| exon 13 | 55 | intron 13 | 81 |
| exon 14 | 89 | intron 14 | 96 |
| exon 15 | 85 | intron 15 | 99 |
| exon 16 | 84 | | |
| | | 3' UTR | 424 |
| Total | 1971 | | 3781 |

TABLE 9

SNPs identified in the Ze gene between orange and yellow lines (SEQ ID NOs: 87-89).

| Marker | Yellow allele | Orange allele | Location |
| --- | --- | --- | --- |
| NCANN009198970 | T | C | 5' UTR |
| NCANN009114570 | A | G | Intron 15 |
| NCANN009199170 | G | T | 3' UTR |

Figure 5:
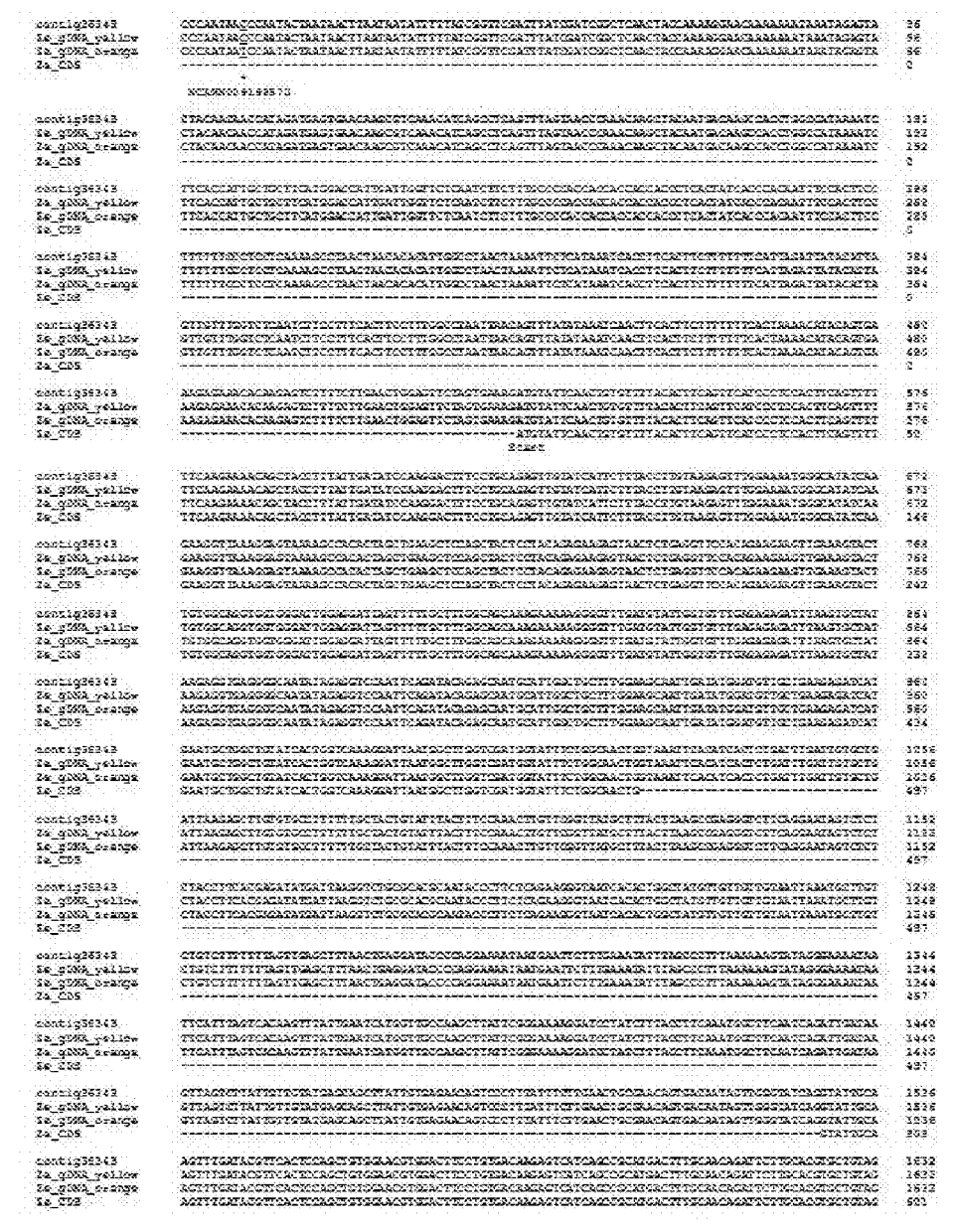
Figure 5:
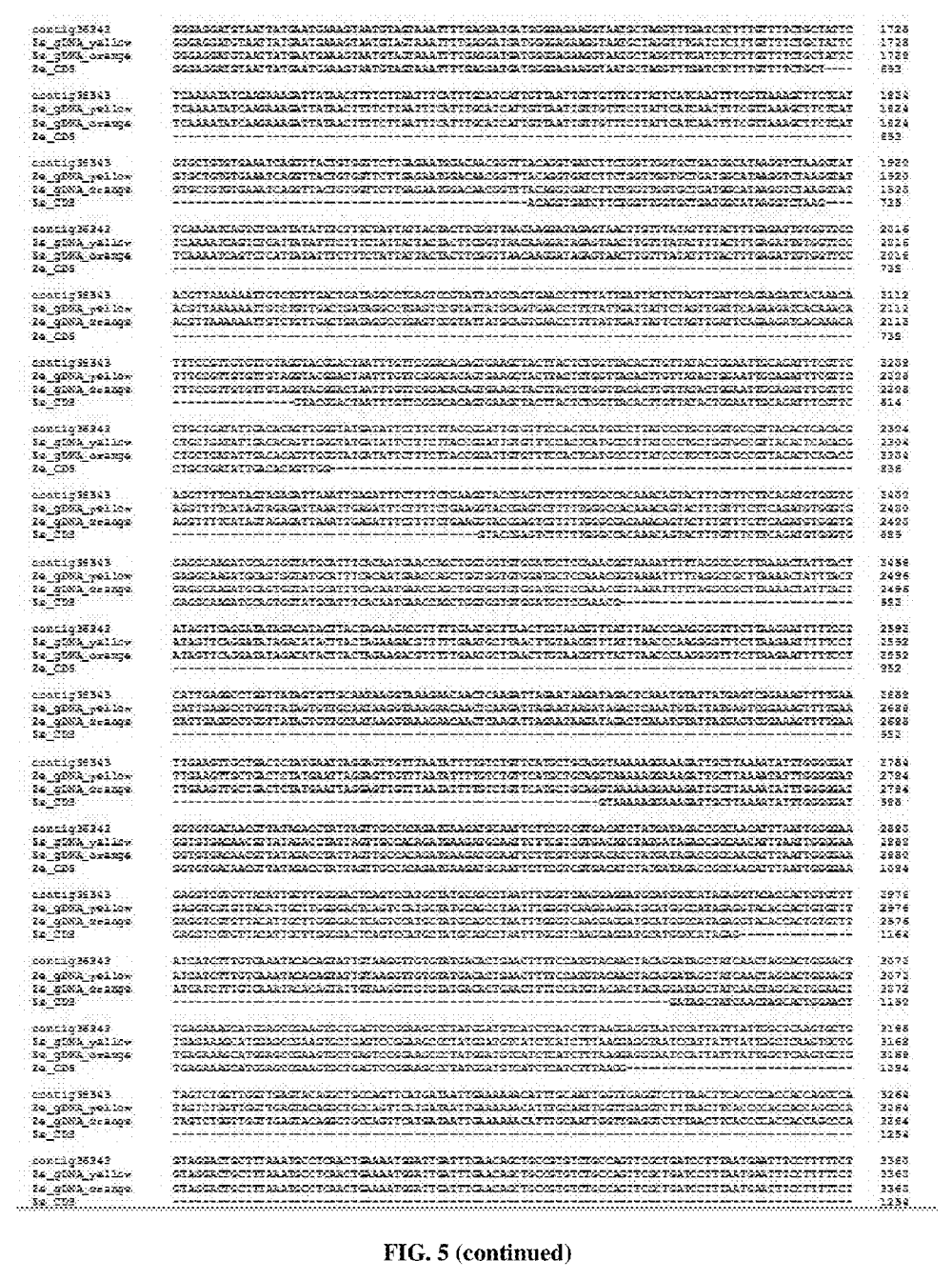
Figure 5:
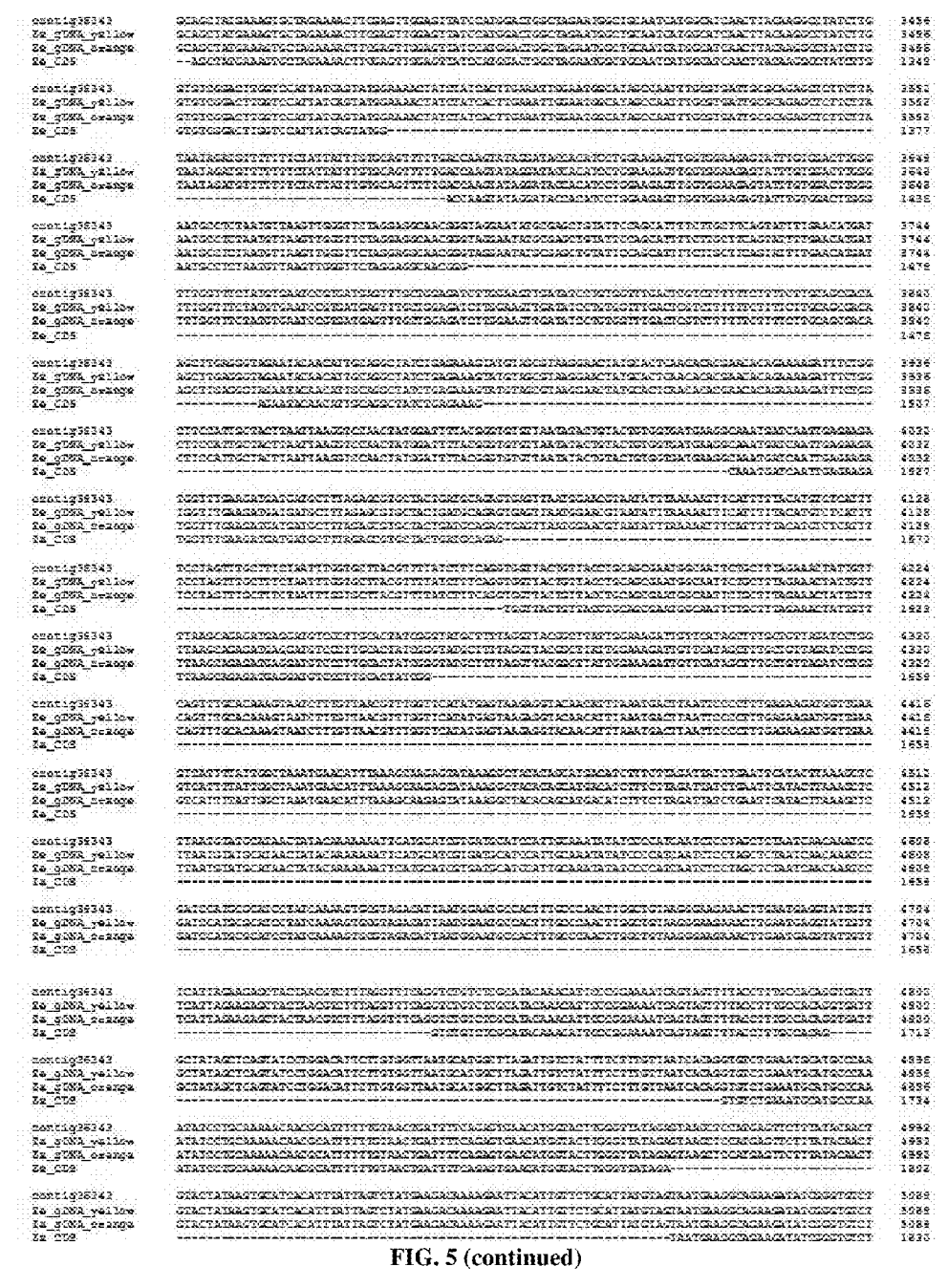

The [A/G] SNP in intron 15 (Table 9) is close to the intron-exon acceptor splice site and the allele found in orange lines (carrying the G allele) has a disrupted intron-exon acceptor site. In the Ze sequence of yellow fruited pepper lines, a typical acceptor splice site for an intron-exon barrier can be found on the borders of intron 15 and exon 16: CAG^GC (SEQ ID NO:90) (the ^ represents the actual splice site). The SNP in the allele found in orange lines has a sequence of CGGGC (SEQ ID NO:91), which is not a functional splice site. This SNP thus likely affects the plant's ability to produce a fully functional Zeaxanthin Epoxidase transcript and, as a result, significantly less yellow pigments are formed in plants carrying this allele in a homozygous state. As a result, these plants have orange fruits. The alignment in FIG. 5 shows the 3' region of the Ze gene and compares sequences of a yellow line to an orange line (SEQ ID NOs:96-97), the predicted coding sequence (SEQ ID NO:98), and a sequence from CM334 ("contig36343"; SEQ ID NO:99). All SNPs are indicated with an asterisk (*) and the marker names (MRNs) are indicated.

To carry out accuracy tests of marker NCANN009114570, a TaqMan™ assay was designed on the SNP NCANN009114570 (Table 10; SEQ ID NOs:92-95). For accuracy tests, marker NCANN009114570 was validated on a panel of 321 leaf samples. The panel was derived from variety trials and was dominated by lines bred for the Dutch greenhouse market. In all tested plants only one plant, out of 321 tested, gave an unexpected genotype, i.e. wherein the identified fruit color did not agree with the genotype at marker NCANN009114570 (yellow fruit expected for TT genotype; orange fruit expected for CC genotype), which was thought to be caused by an error in assignment of fruit color, as this is the same line used in CCS marker testing in which the phenotype and marker genotype did not agree. Thus, in this trial the marker was >99.6% accurate.

TABLE 10

Design details of TaqMan™ assay NCANN009114570 (SEQ ID NOs: 92-95).

| Name | description | Sequence | Allele* |
| --- | --- | --- | --- |
| NCANN009114570_F | forward primer | 1 CAGCAGTTTTTGAAGGAAATTTCATTGTC | |
| NCANN009114570_R | reverse primer | GGCATTGGCAGTAGCTTATTACTCA | |
| NCANN009114570_V | VIC probe | ATGTTATGCGGGCAGCA | C |
| NCANN009114570_M | FAM probe | ATGTTATGCAGGCAGCA | T |

*probes are designed on the reverse complement sequence

Marker NCANN009114570 was designed on the reverse complement sequence of the Ze gene. The [A/G] SNP in the gene is therefore registered as a [C/T] SNP.

In conclusion, marker NCANN009114570 is based on a SNP that disrupts the production of a fully functional Zeaxanthin Epoxidase ("ZEP") transcript. The presence of this mutation appears almost perfectly correlated with the absence of yellow pigments in orange pepper fruits. The marker is highly predictive for mature fruit color in pepper and is a suitable marker for MAS and MABC applications.

This mutation yields a plant that can survive without a functional ZEP protein. It follows that other mutations in the gene also may result in the absence of yellow pigments in orange pepper fruits. An altered ZEP genotype may therefore be provided by any suitable means; for example, EMS, MMS, other mutagen-derived, in situ-derived, or naturally-occurring mutations can provide an altered ZEP genotype suitable for the development of the fruit color phenotypes described here. Color modulation of the fruit color phenotypes described here may also be achieved by transient disruption of ZEP function at the time of fruit set and/or fruit color maturation.

Example 3

Carotenoid Profiles of Red, Orange, and Yellow Pepper Fruits

The carotenoid profiles of various colored pepper fruits were measured, and those data used and to test the predictiveness of markers NCANN009113770 (CCS) and NCANN009114570 (ZEP) for determining the genotypes and phenotypes of the genes responsible for mature pepper fruit color. Carotenoid contents and profiles were analyzed in a panel of 133 pepper varieties representing red (n=55), orange (n=23), and yellow (n=55) mature fruit colors. The panel was selected from variety trials and contained lines predominantly for the Dutch greenhouse market. Carotenoid values were obtained using an Ultra high performance liquid chromatography (UHPLC) UV detection assay. Marker assay test results were obtained from DNA samples isolated from collected leaf samples.

Reversed Phase Ultra High Pressure Liquid Chromatography and UV DAD Detection of Carotenoid Pigments: The pigment carotenoid content of the pepper samples was analyzed by reverse phase ultra high pressure liquid chromatography (UHPLC) UV DAD. All procedures were performed on ice, using amber glassware and/or reduced light where possible. Pepper samples were cut into pieces, removing and discarding the peduncle, seeds, and placental tissue, leaving only the pericarp. The pepper sample was weighed and an equal amount of nanopure water (1:1, weight/weight) was added. Samples were blended in a Vitamix blender (Vitamix Corporation, Cleveland, Ohio, USA) for approximately 30 seconds on high. The puree was transferred to a 50 mL centrifuge tube, and sample extraction and analysis was either performed immediately or stored at −80° C. Pureed pepper pericarp (0.5 g) was extracted with acetone:methanol:hexane (2:1:1, v/v/v, 0.5% BHT) containing 0.5 ppm β-apo-8'-carotenal (Sigma-Aldrich, St. Louis, USA). The extraction mixture was sonicated for 20 minutes on ice. After sonication, 1 M sodium chloride in water was added to the extraction mixture. Extraction vials were centrifuged and 1 ml aliquots of upper hexane phase were syringe filtered and placed in amber vials and either analyzed immediately or stored at −20° C. until analysis. Extracts were separated and analyzed using an Agilent 1260 UHPLC with quaternary pump and Waters BEH C18 column. The injection volume was 2 μl and the eluent flow was 0.375 μl/min. Detection and quantitation was by UV DAD by monitoring at 450±20 nm with no reference wavelength.

Data Processing: Chromatograms were processed using Agilent Chemstation® software to integrate and identify peaks. Carotenoids were identified based upon relative retention time and UV absorption spectra in comparison to authentic standards. Carotenoids were quantified based upon generated relative response factors (RRF) using β-apo-8'-carotenal as an internal standard. Carotenoid esters were tentatively identified based upon absorption spectra, retention time and literature reference values. Retention characteristics of carotenoid esters were used to tentatively identify as either monoester or diester carotenoid pigments. Relative quantification was performed for monoester and diester carotenoid pigments using the calculated RRF values of the free carotenoid authentic standards.

Spectrophotometric Determination of Carotenoid Pigments. UV absorption spectra (375-550 nm) were collected with a UV-Vis spectrophotometer. Briefly, 1.0 grams of pepper puree used was placed in a 50 ml conical tube. To the sample, 40 ml of 100% acetone was added. The tubes were shaken and placed in the dark at room temperature overnight. Prior to analysis, sample tubes were centrifuged for 15 minutes at 3000 rpm at room temperature (RT). A 1.0 ml aliquot was placed in a cuvette and spectra were recorded. Spectra were normalized to the spectra of pure acetone.

TABLE 11

Total carotenoid concentrations (μg/g FW) according to mature pepper fruit phenotype and genotype.

| Fruit Color | NCANN009113770 (INS/DEL) | NCANN009114570 (T/C) | Sample Number (n) | Capsanthin | Capsorubin | Zeaxanthin | β-carotene | β-cryptoxanthin |
|---|---|---|---|---|---|---|---|---|
| Red | INS | T | 36 | 60.80 ± 17.31 | 6.75 ± 2.05 | 1.57 ± 0.38 | 9.67 ± 3.46 | 0.94 ± 0.35 |
| Red | INS | H | 5 | 60.89 ± 21.54 | 5.67 ± 2.10 | 2.83 ± 1.15 | 9.48 ± 4.16 | 1.27 ± 0.56 |
| Red | INS | C | 2 | 25.38 ± 9.97 | 0.78 ± 0.14 | 23.92 ± 5.35 | 17.27 ± 7.11 | 1.91 ± 0.85 |
| Red | H | H | 6 | 64.28 ± 18.19 | 5.58 ± 2.05 | 3.21 ± 1.38 | 15.07 ± 6.16 | 1.79 ± 0.69 |
| Red | H | T | 6 | 49.85 ± 7.25 | 5.058 ± 0.92 | 2.08 ± 0.55 | 15.11 ± 5.15 | 1.23 ± 0.36 |
| Orange | DEL | C | 23 | ND | ND | 38.03 ± 9.98 | 14.07 ± 5.41 | 1.27 ± 0.44 |
| Yellow | DEL | T | 55 | ND | ND | 0.29 ± 0.12 | 0.94 ± 0.40 | 0.17 ± 0.13 |

| Fruit Color | NCANN009113770 (INS/DEL) | NCANN009114570 (T/C) | Sample Number (n) | Violaxanthin | Antheraxanthin | Lutein | α-Carotene |
|---|---|---|---|---|---|---|---|
| Red | INS | T | 36 | 2.58 ± 0.72 | 3.43 ± 0.99 | ND | ND |
| Red | INS | H | 5 | 2.53 ± 0.74 | 4.43 ± 1.65 | ND | ND |
| Red | INS | C | 2 | 9.88 ± 3.95 | 0.14 ± 0.02 | ND | ND |
| Red | H | H | 6 | 3.47 ± 1.02 | 4.28 ± 1.42 | ND | ND |
| Red | H | T | 6 | 2.82 ± 0.41 | 3.32 ± 0.62 | ND | ND |
| Orange | DEL | C | 23 | 1.73 ± 0.50 | 6.66 ± 2.42 | 7.32 ± 1.21 | 0 ± 0 |
| Yellow | DEL | T | 55 | 10.32 ± 3.45 | 1.08 ± 0.41 | 3.47 ± 0.67 | 0.81 ± 0.38 |

*Mean ± SD;
ND—Not Detected;
H—Heterozygous

In red vs. non-red varieties, 55 phenotypic red varieties were analyzed for carotenoid content. As shown in Table 11, all lines phenotypically scored as red contained the red carotenoids capsanthin and capsorubin. Of the 78 non-red varieties (orange and yellow), no capsanthin or capsorubin pigments were detected in any samples tested. Marker NCANN009113770 was applied to the sample set to understand the predictability of red vs. non-red classification. As shown in Table 12, samples containing the CCS insertion (n=43) or heterozygotic (H) for the insertion (n=12), contained the red carotenoids capsanthin and capsorubin. Of the samples positive for the deletion (n=78), no capsanthin or capsorubin pigments were detected. These data indicate that the carotenoids capsanthin and capsorubin are indicative of red pepper fruits and that marker NCANN009113770 predicts the presence or absence of the red carotenoids capsanthin and capsorubin in this subset of red peppers.

Within the non-red varieties, varieties were scored as orange (n=23) or yellow (n=55) based upon visual appearance. As indicated in Table 11, all non-red varieties were positive for the CCS deletion according to the NCANN009113770 marker and were devoid of the red carotenoids capsanthin and capsorubin in their fruits. Among orange varieties, the highest concentration of carotenoids was evidenced from the orange carotenoid fraction, namely zeaxanthin and β-carotene. Zeaxanthin concentrations were highest in the orange varieties compared to both red and yellow varieties. Among yellow varieties, the highest concentration of carotenoids was evidenced in the yellow carotenoids, namely violaxanthin and lutein. The yellow carotenoid concentrations were significantly higher than orange carotenoids in the yellow pepper varieties.

orange varieties, the orange carotenoid fraction constitutes the major carotenoid fraction compared to the yellow carotenoids. In yellow varieties, the yellow carotenoid fraction constitutes the largest carotenoid pool compared to the orange fraction. These data further indicate that mature pepper fruit color is driven by the underlying carotenoid profiles, which constitutes the red, orange, and yellow phenotypic appearance of pepper fruit colors.

Based upon the analytical data, red pepper fruits contain the red carotenoids capsanthin and capsorubin while they are not detected in non-red (orange or yellow) fruits. The presence of red carotenoids was associated with the presence of the CCS insertion (NCANN009113770) while the absence of red carotenoids is associated with the CCS deletion. In orange and yellow fruits, increased concentration of zeaxanthin is associated with orange mature pepper fruit color. Moreover, the increase in zeaxanthin is correlated

TABLE 12

Carotenoid color ratios according to mature pepper fruit phenotype and genotype.

| Fruit Color | NCANN009113770 (INS/DEL) | NCANN009114570 (T/C) | Sample Number (n) | Carotenoid Color Ratio* | | |
|---|---|---|---|---|---|---|
| | | | | Red Ratio $R_{Total}/(Y_{Total} + O_{Total})$ | Orange Ratio $O_{Total}/(R_{Total} + Y_{Total})$ | Yellow Ratio $Y_{Total}/(R_{Total} + O_{Total})$ |
| Red | INS | T | 36 | 3.76 ± 0.52 | 0.17 ± 0.03 | 0.08 ± 0.01 |
| Red | INS | H | 5 | 3.27 ± 0.54 | 0.19 ± 0.04 | 0.09 ± 0.01 |
| Red | INS | C | 2 | 0.49 ± 0.03 | 1.21 ± 0.10 | 0.14 ± 0.01 |
| Red | H | H | 6 | 2.60 ± 0.57 | 0.26 ± 0.06 | 0.09 ± 0.01 |
| Red | H | T | 6 | 2.33 ± 0.49 | 0.30 ± 0.06 | 0.08 ± 0.01 |
| Orange | DEL | C | 23 | NA | 3.37 ± 0.39 | 0.30 ± 0.03 |
| Yellow | DEL | T | 55 | NA | 0.09 ± 0.02 | 11.75 ± 2.92 |

*Mean ± SD

The NCANN009114570 marker is predicted to specify the presence of a fully functional or impaired-function ZEP enzyme. Accordingly, perturbation in this enzyme (e.g. in translation or catalytic function) is expected to produce changes in the carotenoid profile namely through accumulation of zeaxanthin or production of the carotenoids antheraxanthin and violaxanthin. All yellow varieties (n=55) were positive for the T-allele, indicating presence of a fully functional ZEP enzyme. Yellow varieties accumulated the yellow carotenoid violaxanthin at the highest concentration. In comparison, all orange varieties were positive for the C-allele (Table 11), indicating the presence of a ZEP enzyme with reduced function. Accordingly, the orange varieties accumulated significant concentrations of zeaxanthin, implicating a non-functional ZEP protein. Further evidence of a impaired function ZEP is provided within the red varieties. Two red varieties that contained the CCS insertion also contained the C-allele of ZEP. These varieties, while still producing significantly lower concentrations of capsanthin and capsorubin, produced significantly higher concentration of zeaxanthin compared to other red varieties (Table 10). The zeaxanthin concentrations were similar to levels seen in orange varieties. These data indicate that the C-allele of the ZEP protein encodes a ZEP enzyme with significantly decreased function resulting in the accumulation of the orange carotenoid zeaxanthin.

To further understand the contribution of colored carotenoid fractions, color ratios were constructed based upon the total carotenoid concentration of the red, orange, or yellow carotenoid fractions. As shown in Table 12, for red varieties the red carotenoid fraction constitutes the largest pool of carotenoids when compared with the contribution of the orange or yellow carotenoids to the total carotenoid pool. In with the C-allele of marker NCANN009114570. The presence of the ZEP T-allele results in shift in carotenoid fractions towards the yellow carotenoids, resulting in yellow fruit color. Further evidence of the ZEP function and prediction accuracy of marker NCANN009114570 is found in two varieties phenotypically described as red but predicted by this marker to be orange. The major carotenoid accumulated by these two varieties is the orange carotenoid zeaxanthin and the carotenoid distribution, as evidenced by the carotenoid ratios, is aligned with the observed orange carotenoid profiles. The analytical data combined with the marker information, indicate that the CCS and ZEP enzymes predict mature pepper fruit color.

Example 4

Linkage Disequilibrium Decay Surrounding Ccs and Ze

Markers based on causal genes are especially valuable for breeding and trait integration purposes when linkage disequilibrium (LD) around a trait locus is low. On the other hand, when LD around the causal mutation is relatively higher, then a linked marker in strong LD with the causal gene may suffice for most breeding applications. To better understand the value of the discovered mutations, for breeding, an LD analysis using marker data was performed for chromosomes 2 and 6 harboring the color loci Ze and Ccs, respectively. In total, 5191 SNP markers were used in this analysis. The analysis was performed on several pepper subpopulations (based on fruit type) and monomorphic markers within these populations were excluded in the analysis. In total, 882 pepper lines were used for the analysis.

LD was estimated using the $r^2$ metric (Hill and Robertson, TAG 38:226-231, 1968) and was calculated for all pairs of markers on LG6 and LG2 for each subpopulation. LD decay was examined using the equation: $LD_{ij}=1/(1+4b_jd_i)+e_{ij}$, where LD is the observed $r^2$ between the i-th marker pair in subpopulation j, $d_i$ is the genetic distance between the i-th marker pair in Morgans, $b_j$ is the coefficient of LD decay in subpopulation j, and $e_{ij}$ is the random residual. The extent of LD decay was taken to be the genetic distance required for LD to decay to $r^2$=0.1 or to 50% of the maximum estimated value, predicted using the aforementioned model.

LD appears to decay relatively rapidly in pepper: $r^2$ was estimated to reduce to 0.1 within 0.55 cM on LG6 and 1.65 cM on LG2 when elite hot and sweet pepper lines were considered together (e.g. see Table 13). Much of this diversity is attributable to hot pepper varieties: LD decays over 0.41 cM and 0.47 cM in LG6 and LG2, respectively. Conversely, for sweet pepper varieties, LD decays over 0.96 cM on LG6 and 2.47 cM on LG2. That is, for sweet peppers, LD appears to decay ~2.6 times slower on LH2 than LG6. Within sweet pepper varieties, the difference in LD decay is more substantial between bell (blocky; "SB") and mini ("SM") peppers, although LD and LD decay estimates are affected by sample size. For bell peppers, LD decays almost three times slower on LG2 than LG6, which is comparable to estimates of the total population studied.

Excluding all subpopulations with fewer than 20 lines, it takes up to 4.1cM for LD to decay to $r^2$=0.1 on LG6 and up to 10 cM for LD to decay to $r^2$=0.1 on LG2. In consideration of immediate regions of the trait loci, LD decays to $r^2$=0.1 within 2 cM at the CCS locus and 4 cM at the Ze locus. Moreover, LD decay estimates surrounding the traits were very different to those observed for entire linkage groups. When only six relevant pepper types (where mature color varies and where color markers are thus most likely to be useful) were examined, LD decay surrounding Ccs was estimated as unchanged compared to the rest of the linkage group but was 1.5-times faster surrounding Ze than the rest of LG2. Thus, the presumptive causal mutation in Ze described here is of particular value when compared to a physically linked SNP since LD decays relatively rapidly around this locus.

TABLE 13

Summary of LD decay estimates on LG6 and LG2 for each subpopulation. S[BM]RYO indicates the combined population of six pepper types: SBR (i.e. sweet, bell, red subpopulation), SBY (i.e. sweet, bell, yellow subpopulation), SBO (i.e. sweet, bell, orange subpopulation), SMR (i.e. sweet, mini, red subpopulation), SMY (i.e. sweet, mini, yellow subpopulation), and SMO. "cM to ½ $r^2_{max}$" is the genetic distance in cM for $r^2$ to decay to 50% of its predicted maximum; "cM to $r^2$ = 0.1" is the genetic distance in cM for $r^2$ to decay to 0.1; L2:L6 is the ratio of LD decay estimates between LG2 and LG6.

| | | LG6 | | LG2 | | LG2:LG6 | |
|---|---|---|---|---|---|---|---|
| Sub-population | N | cM to ½ $r^2_{max}$ | cM to $r^2$ = 0.1 | cM to ½ $r^2_{max}$ | cM to $r^2$ = 0.1 | cM to ½ $r^2_{max}$ | cM to $r^2$ = 0.1 |
| All | 882 | 0.06 | 0.55 | 0.18 | 1.65 | 2.99 | 2.99 |
| sweet | 537 | 0.11 | 0.96 | 0.27 | 2.47 | 2.57 | 2.57 |
| hot | 345 | 0.05 | 0.41 | 0.05 | 0.47 | 1.15 | 1.15 |
| bell | 319 | 0.21 | 1.87 | 0.60 | 5.43 | 2.90 | 2.90 |
| mini | 17 | 1.90 | 17.10 | 3.14 | 28.22 | 1.65 | 1.65 |
| red | 224 | 0.19 | 1.75 | 0.62 | 5.54 | 3.17 | 3.17 |
| yellow | 95 | 0.45 | 4.06 | 1.10 | 9.94 | 2.45 | 2.45 |
| orange | 17 | 1.07 | 9.67 | 5.78 | 52.06 | 5.39 | 5.39 |
| S[BM][RYO] | 339 | 0.40 | 1.78 | 0.62 | 5.56 | 1.55 | 3.12 |
| SBR | 221 | 0.40 | 1.80 | 0.71 | 6.36 | 1.77 | 3.53 |
| SBY | 89 | 0.66 | 4.11 | 0.68 | 6.09 | 1.03 | 1.48 |
| SBO | 12 | 1.64 | 12.99 | 4.99 | 44.87 | 3.03 | 3.45 |
| SMR | 5 | 13.05 | 115.66 | 12.06 | 108.54 | 0.92 | 0.94 |
| SMY | 6 | 52.51 | 470.75 | 9.60 | 86.39 | 0.18 | 0.18 |
| SMO | 6 | 14.26 | 126.53 | 47.19 | 424.75 | 3.31 | 3.36 |
| All (subregion) | 882 | 0.12 | 1.05 | 0.07 | 0.67 | 0.64 | 0.64 |
| S[BM][RYO] (subregion) | 339 | 0.61 | 1.93 | 0.42 | 3.82 | 0.69 | 1.97 |

Example 5

Breeding for Fruit Color Using Markers for Ccs and Ze

The identification of the presumptive causal SNPs in the two major color genes in pepper allows inference as to mature fruit color in pepper based on marker data. Table 14 shows the predicted fruit colors based on the markers NCANN009113770 (red vs. yellow; based on the Ccs gene) and NCANN009114570 (yellow vs. orange based on the Ze gene). The Ccs red allele is dominant to the yellow allele, and the yellow Ze allele is dominant to the orange allele. Therefore, a plant heterozygous for both genes has red fruits.

TABLE 14

Expected fruit colors based on Ccs and Ze genotypes.

| | | | NCANN009113770 | | |
|---|---|---|---|---|---|
| | | | INSINS CCSCCS | INSDEL CCSccs | DELDEL ccsccs |
| NCANN009114570 | AA | ZEZE | Red | Red | Yellow |
| | AG | ZEze | Red | Red | Yellow |
| | GG | zeze | Red* | Red* | Orange |

*Plants with a CCSCCSzeze genotype (red-orange fruits) are visually scored to have red fruits, however the carotenoid profile is more consistent with orange fruits. It is expected that the same is true of plants with the CCSccszeze genotype.

Figure 6:
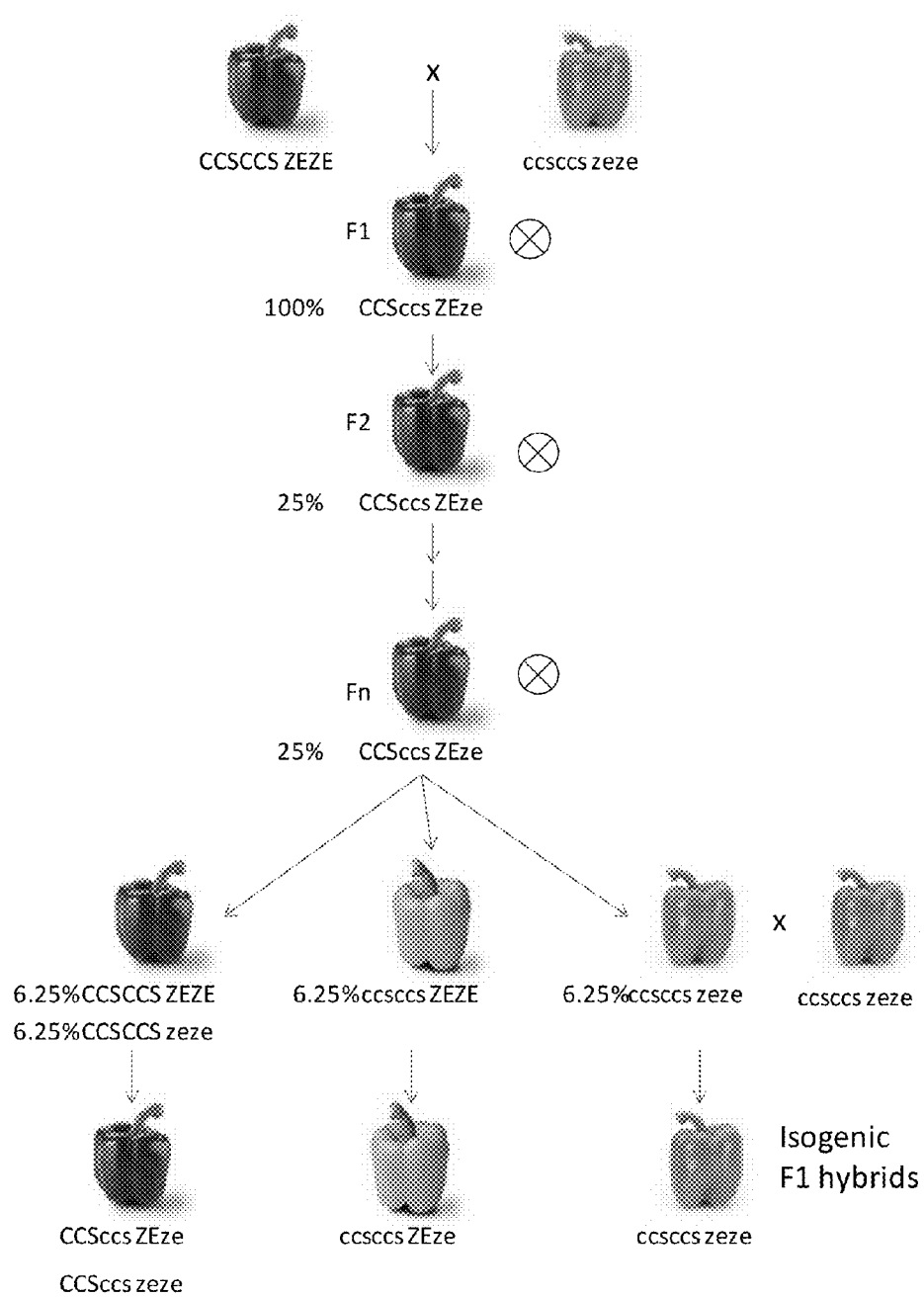
FIG. 6: An exemplary breeding scheme to create nearly isogenic orange, yellow, and red fruited pepper lines.

These two markers allow for marker assisted breeding in pepper for mature fruit color as described below. Sources of the genetic diversity described here exist in publically available germplasm. For example, diversity in the described color markers exists in the commercial hybrids Orange Glory (ccsccs zeze), Derby (ccsccs ZEZE), Shanghai (ccsccs ZEZE), Aifos (CCSCCS ZEZE) and Darsena (CCSCCS ZEZE). For instance, as discussed above, breeding for fruit color in peppers can be performed, wherein these color markers (or analogous linked markers) allow for simplification of multiple breeding programs based on color into one multi-color breeding program (FIG. 6). This can be achieved by crossing a red line that has both the intact Ccs and Ze alleles (CCSCCS ZEZE) with an orange line (ccsccs zeze) and maintaining both loci in a heterozygous state throughout the breeding process. In each generation, the subset of plants heterozygous for both color loci are selected with markers, and breeders may perform additional phenotypic selection on these plants. When the line is sufficiently genetically and phenotypically fixed after n generations the line can be selfed one final time and the progeny of the desired color genotype and phenotype can be selected using the markers for Ccs and Ze. This results in homozygous nearly isogenic lines that only differ in the mature fruit colors red, yellow and orange and loci tightly linked to the color loci. These nearly isogenic lines can be used to produce nearly isogenic hybrids, which are of interest because each of the differently colored nearly isogenic hybrids will have similar horticultural properties, allowing growers to manage each variety in the same way. Currently, red, yellow and orange commercial pepper varieties are each distinct and may each have different pruning, nutritional, or pest control needs, adding complexity and expense to operations producing more than one color type.

Figure 7:
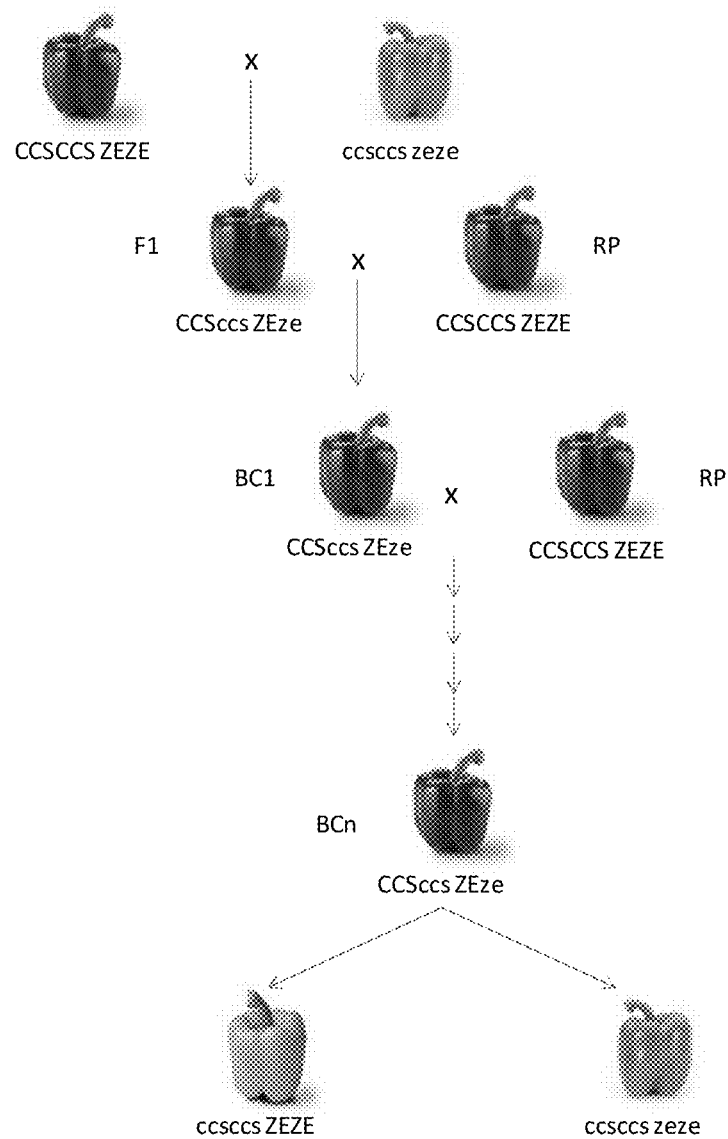
FIG. 7: Exemplary breeding scheme to create nearly isogenic orange, yellow, and red fruited pepper lines through marker assisted backcrossing ("MABC").

Isogenic inbred lines may also be created through marker assisted back crossing (MABC) using the new markers. Because red lines are typically the most advanced with respect to agronomic and disease traits, an improved orange or yellow line could be created by crossing an orange line with good color (color donor) to an elite red line with good agronomic and disease traits (recurrent parent). (FIG. 7).

Finally conventional marker-assisted breeding (MAS) can benefit greatly from the use of these color markers. Again, because red is the most economically important color and typically the most focused on for breeding efforts, MAS can be used to improve the orange and yellow germplasm. In a red by orange cross the red colored parent can be used to introduce more advanced agronomic traits while the orange parent is used to introduce the preferred color alleles. The color markers can be used to fix the color loci in the F2 generation and in subsequent generations, the lines with the best agronomic traits can be selected on a family basis. These methodologies may be used within and among any pepper species that are crossable in the genus *Capsicum*. For example these markers may be used to move these color mutations, and thus a desired fruit color phenotype, into any desired pepper genetic background.

What is claimed is:

1. A package of *Capsicum annuum* pepper fruits comprising at least two different colors of pepper fruits selected from the group consisting of red, yellow, orange, and red-orange, wherein the peppers are grown from near isogenic pepper varieties, wherein the near isogenic pepper varieties are at least 95% identical over the entire genome, wherein the pepper varieties are hybrid varieties, and wherein all of said hybrid varieties share a parent line; and wherein at least one of the near-isogenic pepper varieties produces red-orange fruit, said pepper variety producing red-orange fruit comprising two recessive and non-functional alleles at the Zeaxanthin Epoxidase (Ze) locus and at least one dominant and functional allele at the Capsanthin-Capsorubin Synthase (Ccs) locus.

2. The package of claim 1, comprising from about 1 to about 5 pepper fruits per color.

3. The package of claim 1, comprising at least three different colors of pepper fruits.

4. The package of claim 1, comprising at least four different colors of pepper fruits.

5. The package of claim 1, wherein the package further comprises a green pepper fruit.

6. The package of claim 1, wherein said pepper varieties are sweet peppers.

7. A method of producing *Capsicum annuum* pepper fruits comprising: growing at least two near isogenic pepper lines that collectively comprise functional and non-functional Capsanthin-Capsorubin Synthase (Ccs) and Zeaxanthin Epoxidase (Ze) alleles, and harvesting pepper fruit therefrom, wherein the near isogenic pepper lines are at least 95% identical over the entire genome, wherein the pepper fruit are of at least two different colors selected from the group consisting of red, yellow, orange, red-orange, and green; and wherein at least one of the near-isogenic pepper lines produces red-orange fruit, said pepper line producing red-orange fruit comprising two recessive and non-functional alleles at the Zeaxanthin Epoxidase (Ze) locus and at least one dominant and functional allele at the Capsanthin-Capsorubin Synthase (Ccs) locus.

8. The method of claim 7, further comprising packaging the pepper fruit in a single package, wherein the pepper fruit are of at least two different colors selected from the group consisting of red, yellow, orange, red-orange, and green.

9. A container comprising seeds of at least two near isogenic *Capsicum annuum* pepper varieties, wherein the near isogenic pepper varieties are at least 95% identical over the entire genome, wherein the pepper varieties produce fruit of different fruit colors, wherein the fruit colors are selected from the group consisting of: red, yellow, orange, and red-orange; and wherein at least one of the near-isogenic pepper varieties produces red-orange fruit, said pepper variety producing red-orange fruit comprising two recessive and non-functional alleles at the Zeaxanthin Epoxidase (Ze) locus and at least one dominant and functional allele at the Capsanthin-Capsorubin Synthase (Ccs) locus.

10. The container of claim 9, defined as comprising seeds of at least three near isogenic pepper varieties that produce fruit of different fruit colors.

11. The container of claim 9, defined as comprising seeds of at least four near isogenic pepper varieties that produce fruit of different fruit colors.

\* \* \* \* \*

SEQUENCE LISTING

```
<160> NUMBER OF SEQ ID NOS: 99

<210> SEQ ID NO 1
<211> LENGTH: 1497
<212> TYPE: DNA
<213> ORGANISM: Capsicum annuum

<400> SEQUENCE: 1
atggaaaccc ttctaaagcc ttttccatct cctttacttt ccattcctac tcctaacatg      60
tatagtttca aacacaactc cacttttcca aatccaacca aacaaaaaga ttcaagaaag     120
ttccattata gaaacaaaag cagtacacat ttttgtagct ttcttgattt agcacccaca     180
tcaaagccag agtctttaga tgttaacatc tcatgggttg atactgatct ggacggggct     240
gaattcgacg tgatcatcat tggaactggc cctgccgggc ttcggctagc tgaacaagtt     300
tctaaatatg gtattaaggt atgttgcgtt gacccttcac cactttccat gtggccaaat     360
aattatggtg tttgggttga tgagtttgaa aagttgggat tagaagattg tctagatcat     420
aagtggcctg tgagttgtgt tcatataagt gatcacaaga ctaagtattt ggacagacca     480
tatggtagag taagtagaaa gaagttgaag ttgaaattgt tgaatagttg tgttgaaaat     540
agagtgaagt tttataaagc caaggttttg aaagtgaagc atgaagaatt tgagtcttcg     600
attgtttgtg atgatggtag gaagataagc ggtagcttga ttgttgatgc aagtggctat     660
gctagtgatt ttatagagta tgacaagcca agaaaccatg gttatcaagt tgctcatggg     720
attttagcag aagttgataa tcatccattt gatttggata aaatgatgct tatggattgg     780
agggattctc atttaggtaa tgagccatat ctgagggtga agaatactaa agaaccaaca     840
ttcttgtatg caatgccatt tgataggaat ttggtattct tggaagagac ttctttagtg     900
agtcggccta tgttatcgta tatggaagtg aaaagaagga tggtagcaag attaagacat     960
ttggggatca aagtgagaag tgtccttgag gaagagaagt gtgtgatcac tatgggagga    1020
```

```
ccacttccgc ggattcctca aaatgttatg gctattggtg ggacttcagg gatagttcat    1080
ccatcgtctg ggtacatggt ggctcgtagc atggcattgg caccagtact ggctgaggcc    1140
atcgtcgaaa gccttggctc aacaagaatg ataagagggt ctcaacttta ccatagagtt    1200
tggaatggtt tgtggccttc ggatagaaga cgtgttagaa aatgttattg tttcggaatg    1260
gagactttgt tgaagcttga tttggaaggt actaggagat tgtttgatgc tttctttgat    1320
gttgatccca agtactggca cgggttcctt tcttcaagat tgtctgtcaa agaacttgct    1380
gtactcagtt tgtaccttttt tggacatgcc tctaatttgg ctaggttgga tattgttaca    1440
aagtgcactg tccccttggt taaactgctg ggcaatctag caatagagag cctttga       1497
```

```
<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
caactccact tttccaaatc                                                   20

<210> SEQ ID NO 3
<211> LENGTH: 20
<212> TYPE: DNA
<213> ORGANISM: Artificial sequence
<220> FEATURE:
<223> OTHER INFORMATION: Primer

<400> SEQUENCE: 3
ggttgatact gatctggacg                                                   20

<210> SEQ ID NO 4
<211> LENGTH: 21
<212> TYPE: DNA
<213> ORGANISM: Artificial sequence
<220> FEATURE:
<223> OTHER INFORMATION: Primer

<400> SEQUENCE: 4
gtgagtcggc ctatgttatc g                                                 21

<210> SEQ ID NO 5
<211> LENGTH: 21
<212> TYPE: DNA
<213> ORGANISM: Artificial sequence
<220> FEATURE:
<223> OTHER INFORMATION: Primer

<400> SEQUENCE: 5
gtgagtcggc ctatgttatc g                                                 21

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
tgttgatccc aagtactggc                                                   20

<210> SEQ ID NO 7
```

```
<211> LENGTH: 22
<212> TYPE: DNA
<213> ORGANISM: Artificial sequence
<220> FEATURE:
<223> OTHER INFORMATION: Primer

<400> SEQUENCE: 7
agacttggta tcagattgtg gc                                              22

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
agccacaatc cgataccaag                                                 20

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
gagggacaag agtggagcag                                                 20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
tcgaaagcct tggctcaaca                                                 20

<210> SEQ ID NO 11
<211> LENGTH: 23
<212> TYPE: DNA
<213> ORGANISM: Artificial sequence
<220> FEATURE:
<223> OTHER INFORMATION: Primer

<400> SEQUENCE: 11
ttttgtatct ccctttccca gaa                                             23

<210> SEQ ID NO 12
<211> LENGTH: 26
<212> TYPE: DNA
<213> ORGANISM: Artificial sequence
<220> FEATURE:
<223> OTHER INFORMATION: Primer

<400> SEQUENCE: 12
tctctaacac gtcttctatc cgaagg                                          26

<210> SEQ ID NO 13
<211> LENGTH: 18
<212> TYPE: DNA
<213> ORGANISM: Artificial sequence
<220> FEATURE:
<223> OTHER INFORMATION: Primer

<400> SEQUENCE: 13
```

```
agaatgataa gagggtct                                               18

<210> SEQ ID NO 14
<211> LENGTH: 18
<212> TYPE: DNA
<213> ORGANISM: Artificial sequence
<220> FEATURE:
<223> OTHER INFORMATION: Probe

<400> SEQUENCE: 14
cttttagagt ttggaatg                                               18

<210> SEQ ID NO 15
<211> LENGTH: 25
<212> TYPE: DNA
<213> ORGANISM: Artificial sequence
<220> FEATURE:
<223> OTHER INFORMATION: Primer

<400> SEQUENCE: 15
ccaaacactt tgaattggct ggata                                       25

<210> SEQ ID NO 16
<211> LENGTH: 36
<212> TYPE: DNA
<213> ORGANISM: Artificial sequence
<220> FEATURE:
<223> OTHER INFORMATION: Primer

<400> SEQUENCE: 16
actatattaa ctttcctaat aattcttgct ttccca                           36

<210> SEQ ID NO 17
<211> LENGTH: 22
<212> TYPE: DNA
<213> ORGANISM: Artificial sequence
<220> FEATURE:
<223> OTHER INFORMATION: Probe

<400> SEQUENCE: 17
tgctgttaat gattaataac at                                          22

<210> SEQ ID NO 18
<211> LENGTH: 20
<212> TYPE: DNA
<213> ORGANISM: Artificial sequence
<220> FEATURE:
<223> OTHER INFORMATION: Probe

<400> SEQUENCE: 18
ctgttaatga ttaaaaacat                                             20

<210> SEQ ID NO 19
<211> LENGTH: 206
<212> TYPE: DNA
<213> ORGANISM: Capsicum annuum
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (88)..(91)
```

<223> OTHER INFORMATION: n is a, c, g, or t

<400> SEQUENCE: 19

```
agccacaatc cgataccaag tctgtatttg gaagcacngn ctaattgtta tggttaccaa    60
acactttgaa ttggctggat aataacannn nggaaattta tgttwttaat cattaacagc   120
aaattgggaa agcaagaatt attaggaaag ttaatatagt gtcttggtta ttctaatgga   180
gtgggttatg caaattaagt tccctt                                        206
```

<210> SEQ ID NO 20
<211> LENGTH: 206
<212> TYPE: DNA
<213> ORGANISM: Capsicum annuum
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (88)..(91)
<223> OTHER INFORMATION: n is a, c, g, or t

<400> SEQUENCE: 20

```
agccacaatc cgataccaag tctgtatttg gaagcacngn ctaattgtta tggttaccaa    60
acactttgaa ttggctggat aataacannn nggaaattta tgttwttaat cattaacagc   120
aaattgggaa agcaagaatt attaggaaag ttaatatagt gtcttggtta ttctaatgga   180
gtgggttatg caaattaagt tccctt                                        206
```

<210> SEQ ID NO 21
<211> LENGTH: 5105
<212> TYPE: DNA
<213> ORGANISM: Capsicum annuum
<220> FEATURE:
<221> NAME/KEY: misc_feature
<222> LOCATION: (4775)..(4775)
<223> OTHER INFORMATION: A may be either A or a deletion

<400> SEQUENCE: 21

```
tgttgaatgg aaaatattgg aagaatttca tttcatttta caaaaataaa gagtgtagag    60
ggtattttg taaatcaata ttttttctat aaaaaatata taagaaatat tatttaata   120
catcaaatca atactgtat aagaaataat gttaacataa ttaatgcaag tatagctaat   180
accaacatta ctaatgcaag tattactaat acaccatatt ctatattaat cttatatact   240
ctaccaaacg accctaagtg tgtatctata tcctccgaga atttggaatt tgcaaattcc   300
aagttttgta tctcccttc ccagaaatta agataattct ggtgctttta gcattagaaa   360
agtatttatt gggtagggaa atgtcatgac ttcacagcat taagcatcaa gggtataact   420
taatgaaata gtggtcaatg aattatattg agaatgacga ggtctctgtt ccaactttgg   480
tagactttgg aaatgctcgt ctggacgccg cccattcttt ctagtcttgg tgccattcta   540
tttggtctga gactggcatg atgccaaatt ctaaccttt cacaatgagc attcgaccta   600
ctcttctttt ttacgactct atttgaccta ctaggcattg gccaacttgg ctaaccactt   660
gaggaactag agttcggatt caatagaatc taataaattt aatcaaaaga cttcatgtat   720
attgaaaaat ctatttataa ctaactttaa atcggccttt acgtatcgac gtaatcaaaa   780
ttgtgtcagc ttgccacgtg gggtctagta tgagtttgaa attggtcata ggggccccaa   840
```

```
ttccactaat acagctgccg tccatgcact acaagacaaa tacaccacta tgtttgttag      900
tgcttggtaa atgtaaaaca aacttttgat gagaatctat tcgtggcatc gaagtgctgc      960
aaattggctt ttacctctgc tacttcaagc ctcactgatt ttcaccccaa ctttctcatt     1020
tcccttttcaa ggatttgatt ttccagttgg gcatgttaaa aacaacaatt ttcctcaaaa    1080
ctgtagaaat gatttytcat attttaatca gtcaaattat ttaaacaaga agttgatttt     1140
tttttaattt ttttttttac aaaaaaattt caaatgtcaa gtaagatttt tcaaattgaa     1200
actgaataag ctgcgacttt agaaacaaaa aactaagata agtaaaaata ccaaaaagag     1260
tgaatcacat caattgaatt cttccaacag ttcgtttttt agtttctgtt ttgggaagag     1320
gagtactaca aggtaggacc tccaacaatc aacaatatct aagttgcaaa agttttgtg      1380
cgttttttag tttctgtttc gagaagagga atactacaag ttcgtttttt agtttctgtt    1440
ttgggaagag gagtactgca aggtaggacc tccaacaatt atcaatatct aaattgcaaa    1500
aatttcagtt cgttttttagt ttctgtttcg ggaagaggaa tactacaagt tcgtttttta    1560
gtttctatttt tgggaagagg agtactacaa ggtaggacct ccaataccta aattgcaaaa    1620
atttcagttc gttttttagt ttcagtttag ggaagaggaa tactacaagg taggacctcc    1680
aacaatcatc agtacctaaa ttgcaaaaat ttcagttcgt tttttagttt atgtttggga    1740
agaagaatac tacaaggcag tggcggagct accttatgat tagggggttc atccgaacct    1800
ccttcgacgg aaaattatac tattttata agtgaaaatt atttttatg tatatataat     1860
tgatgttgaa cccccttcgg ttagttcatg tatctatatt ttttattt gaacccccgat      1920
gaaaattttg gctccgccac tgctacaagg taggacctcc aacaatcacc aatacctaaa    1980
ttgcaaaaat ttcagtttgt tttttagttt ctgttttggg aagaggaata ctacaaggta    2040
ggacctccaa caatcaccaa tacctaaatt gcaacgtttt tttagtttct gttttgggaa    2100
gaggaatact acatggtagg gcctccaaca atcaccaata cctaaattgc aaaaatttca    2160
gttcgtatttt tcgtttctat tttgggaagt ggaatagtat aaggtaggac ctccaacaat    2220
caccaataccc taaattaaag ttccgattca ttttttagtt tctgttttgg aaagagaaat    2280
actacaaggt agggcctaca acaatcacca gtacctaaat tgtaaaaatt tcagttcgtt    2340
ttttagtttc tattttgaga agaggaatgc tacaaggtag ggcctacaac aatcaccagt    2400
acctaaattg taaaaatttc agttcgtttt ttagtttctg ttttgggaag aggaatacta    2460
caaggtaggg ccttcaacaa tcagcaatac ctaaattaca aaatttcaa ttcgttttttt     2520
agtttctgtt ttgggaagag gaatactaca aggcagtggc ggagctacct tatgattagg    2580
ggttcatccg aacctccttc gacggaaaat tatactattt ttatatagta aaaattattt    2640
tttatgtata tataattgat gttgaacccc cttcggttag tttgtgtatc tatatttttt    2700
tattttgaac ctccttgata aaaaattttg actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaatacct aaattgcaaa aatttcagtt    2880
tgttttttag tttctgtttt gggaagagga atactacaag gtaaggcctc caacaatcac    2940
caatacctaa attgcaaaaa tttcagttcg tattttcgtt tctatttttgg gaagtggaat    3000
agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
```

```
taaggtagga cctccaacaa tcaccaatac ctaaattgca aaagttccga ttctttttt     3240 agtttctgtt ttggaaagag aaatactaca agataggacc ttcaacaatc accaatacct   3300
aaattgcaaa aacttcagtt cattttttag tttctgtttt gggaagaaga atacttcaag   3360
gtaacaatca ccaataccta aawwaaattt cagttagttt tttagtttct gtttttggga   3420
agaggaatac tttcttttgc tatataaagc caaagtaggt acctataagc atcaatattt   3480
tgtattgctt agtgattccc ctagttcggt atttcattt ttttcactat actatatcac    3540
ctcctctcat aaatagccat tataaatctt gcattttctc taatgaaaac ccttctaaag   3600
ccttttccat ctcctttact ttccattcct actcctaaca tgtatagttt caaacacaac   3660
tccacttttc caaatccaac caaacaaaaa gattcaagaa agttccatta tagaaacaaa   3720
agcagtacac atttttgtag ctttcttgat ttagcaccca catcaaagcc agagtcttta   3780
gatgttaaca tctcatgggt tgatactgat ctggacgggg ctgaattcga cgtgatcatc   3840
attggaactg gccctgccgg gcttcggcta gctgaacaag tttctaaata tggtattaag   3900
gtatgttgcg ttgacccttc accactttcc atgtggccaa ataattatgg tgtttgggtt   3960
gatgagtttg aaaagttggg attagaagat tgtctagatc ataagtggcc tgtgagttgt   4020
gttcatataa gtgatcacaa gactaagtat ttggacagac catatggtag agtaagtaga   4080
aagaagttga agttgaaatt gttgaatagt tgtgttgaaa atagagtgaa gttttataaa   4140
gccaaggttt tgaaagtgaa gcatgaagaa tttgagtctt cgattgtttg tgatgatggt   4200
aggaagataa gcggtagctt gattgttgat gcaagtggct atgctagtga ttttatagag   4260
tatgacaagc caagaaacca tggttatcaa gttgctcatg ggattttagc agaagttgat   4320
aatcatccat ttgatttgga taaaatgatg cttatggatt ggagggattc tcatttaggt   4380
aatgagccat atctgagggt gaagaatact aaagaaccaa cattcttgta tgcaatgcca   4440
tttgatagga atttggtatt cttggaagag acttctttag tgagtcggcc tatgttatcg   4500
tatatggaag tgaaaagaag gatggtagca agattaagac atttggggat caaagtgaga   4560
agtgtccttg aggaagagaa gtgtgtgatc actatgggag gaccacttcc gcggattcct   4620
caaaatgtta tggctattgg tgggacttca gggatagttc atccatcgtc tgggtacatg   4680
gtggctcgta gcatggcatt ggcaccagta ctggctgagg ccatcgtcga aagccttggc   4740
tcaacaagaa tgataagagg gtctcaactt taccatagag tttggaatgg tttgtggcct   4800
tcggatagaa gacgtgttag agaatgttat tgtttcggaa tggagacttt gttgaagctt   4860
gatttggaag gtactaggag attgtttgat gctttctttg atgttgatcc caagtactgg   4920
cacgggttcc tttcttcaag attgtctgtc aaagaacttg ctgtactcag tttgtacctt   4980
tttggacatg cctctaattt ggctaggttg gatattgtta caagtgcac tgtcccttg    5040 gttaaactgc tgggcaatct agcaatagag agcctttgaa ttaatatgat agttttgaag   5100
cactg                                                              5105

<210> SEQ ID NO 22
<211> LENGTH: 678
<212> TYPE: DNA
<213> ORGANISM: Capsicum annuum

<400> SEQUENCE: 22
tgttgaatgg aaaatattgg aagaatttca tttcatttta caaaaataaa gagtgtagag    60 ggtattttg taaatcaata ttttttctat aaaaaatata aagaaatat tattttaata    120 catcaaatca aatactgtat aagaaataat gttaacataa ttaatgcaag tatagctaat   180
```

```
accaacatta ctaatgcaag tattactaat acaccatatt ctatattaat cttatatact      240
ctaccaaacg accctaagtg tgtatctata tcctccgaga atttggaatt tgcaaattcc      300 aagtttgta  tctcccttc  ccagaaatta agataattct ggtgctttta gagtttggaa      360
tggtttgtgg ccttcggata gaagacgtgt tagagaatgt tattgtttcg gaatggagac     420
tttgttgaag cttgatttgg aaggtactag gagattgttt gatgctttct ttgatgttga     480
tcccaagtac tggcacgggt tcctttcttc aagattgtct gtcaaagaac ttgctgtact     540
cagtttgtac cttttggac  atgcctctaa tttggctagg ttggatattg ttacaaagtg     600
cactgtcccc ttggttaaac tgctgggcaa tctagcaata gagagccttt gaattaatat     660
gatagttttg aagcactg                                                   678
```

```
<210> SEQ ID NO 23
<211> LENGTH: 1000
<212> TYPE: DNA
<213> ORGANISM: Capsicum annuum
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 23
tagagtttgg aatggtttgt ggccttcgga tagaagacgt gttagagaat gttattgttt      60
cggaatggag actttgttga agcttgattt ggaaggtact aggagattgt ttgatgcttt     120
```

```
ctttgatgtt gatcccaagt actggcacgg gttcctttct tcaagattgt ctgtcaaaga      180
acttgctgta ctcagtttgt accttttttgg acatgcctct aatttggcta ggttggatat    240
tgttacaaag tgcactgtcc ccttggttaa actgctgggc aatctagcaa tagagagcct     300
ttgaattaat atgatagttt tgaagcactg yttttcatttt aatttcttag gttattttca    360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnnn nnncattgga caaaagtata gagccacaat cngataccaa     540
gtctgtattt ggaagcacng nctaattgtt atggttacca acactttga attggctgga     600 taataacann nnggaanttt atgttattaa tcattaacag caaattggga aagcaagaat     660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagttttag                          1000

<210> SEQ ID NO 24
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
```

<220> FEATURE:
<221> NAME/KEY: misc_feature
<222> LOCATION: (945)..(947)
<223> OTHER INFORMATION: n is a, c, g, or t

<400> SEQUENCE: 24

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga    180
acttgctgta ctcagtttgt acctttttgg acatgcctct aatttggcta ggttggatat    240
tgttacaaag tgcactgtcc ccttggttaa actgctgggc aatctagcaa tagagagcct    300
ttgaattaat atgatagttt tgaagcactg ntttcattttt aatttcttag gttattttca   360
tcttttmtca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnnn nnncattgga caaaagtata gagccacaat cngataccaa    540
gtctgtattt ggaagcacng nctaattgtt atggttacca aacactttga attggctgga   600
taataacann nnggaanttt atgttattaa tcattaacag caaattggga aagcaagaat    660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagtttttag                         1000
```

<210> SEQ ID NO 25
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (503)..(503)
<223> OTHER INFORMATION: G is either G or a deletion
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:

<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 25

```
tagagtttgg aatggtttgt ggccttcgga tagaagacgt gttagagaat gttattgttt      60
cggaatggag actttgttga agcttgattt ggaaggtact aggagattgt ttgatgcttc     120
ctttgatgtt gatcccaagt actggcacgg gttcctttct tcaagattgt ctgtcaaaga    180
acttgctgta ctcagtttgt acctttttgg acatgcctct aatttggcta ggttggatat    240
tgttacaaag tgcactgtcc ccttggttaa actgctgggc aatctagcaa tagagagcct    300
ttgaattaat atgatagttt tgaagcactg ntttcatttt aatttcttag ttattttca     360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgt atggttgtcg atgcattgga caaaagtata gagccacaat cngataccaa    540
gtctgtattt ggaagcacng nctaattgtt atggttacca acactttga attggctgga    600
taataacann nnggaanttt atgttattaa tcattaacag caaattggga agcaagaat     660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagtttttag                        1000
```

<210> SEQ ID NO 26
<211> LENGTH: 986
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (518)..(518)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (595)..(598)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (931)..(933)
<223> OTHER INFORMATION: n is a, c, g, or t

<400> SEQUENCE: 26

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga    180
acttgctgta ctcagtttgt acctttttgg acatgcctct aatttggcta ggttggatat    240
tgttacaaag tgcactgtcc ccttggttaa actgctgggc aatctagcaa tagagagcct    300
ttgaattaat atgatagttt tgaagcactg ntttcatttt aatttcttag gttattttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgc attggacaaa agtatagagc cacaatcnga taccaagtct gtatttggaa    540
gcacngncta attgttatgg ttaccaaaca ctttgaattg ctggataat aacannnngg     600
aantttatgt tattaatcat taacagcaaa ttgggaaagc aagaattatt aggaaagtta    660
atatagtgtc ttggttattc taatggagtg ggttatgcaa attaagttcc cttntcaaag    720
tttggtttat gaactgctcc actcntgtcc ctcttaaaag ccttaatccc aacatgtacc    780
accaaagaan tgagctgctc catcagatcc tttgagaatg ttaatatgtt atttaaatga    840
aggactgaat gattatgagg atgcaatgca taggtttaat taccagttat ctgtaaattg    900
tcttcnttgc cattattta aaagtttaat nnnaagtgta acatctacaa agagttgata    960
attacaaagc agctactagt ttttag                                         986
```

<210> SEQ ID NO 27
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)

```
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 27
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttccttcct tcaagattgt ctgtcaaaga     180
acttgctgta ctcagtttgt accttttgg acatgcctct aatttggcta ggttggatat      240
tgttacaaag tgcactgtcc ccttggttaa actgctgggc aatctagcaa tagagagcct     300
ttgaattaat atgatagttt tgaagcactg ntttcatttt aatttcttag gttattttca     360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnnn nnncattgga caaaagtata gagccacaat cygataccaa     540
gtctgtattt ggaagcacng nctaattgtt atggttacca aacactttga attggctgga     600
taataacann nnggaanttt atgttattaa tcattaacag caaattggga aagcaagaat     660
tattaggaaa gttaatatag tgtcttggtt attctaatgg agtgggttat gcaaattaag     720
ttcccttntc aaagtttggt ttatgaactg ctccactcnt gtccctctta aaagccttaa     780
tcccaacatg taccaccaaa gaantgagct gctccatcag atcctttgag aatgttaata     840
tgttatttaa atgaaggact gaatgattat gaggatgcaa tgcataggtt taattaccag     900
ttatctgtaa attgtcttcn ttgccattat tttaaaagtt taatnnnaag tgtaacatct     960
acaaagagtt gataattaca aagcagctac tagtttttag                          1000
```

```
<210> SEQ ID NO 28
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 28
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga     180
acttgctgta ctcagtttgt accttttggg acatgcctct aatttggcta ggttggatat     240
tgttacaaag tgcactgtcc ccttggttaa actgctgggc aatctagcaa tagagagcct     300
ttgaattaat atgatagttt tgaagcactg ntttcatttt aatttcttag gttattttca     360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnnn nnncattgga caaaagtata gagccacaat cngataccaa     540
gtctgtattt ggaagcacwg nctaattgtt atggttacca aacactttga attggctgga     600
taataacann nnggaanttt atgttattaa tcattaacag caaattggga aagcaagaat     660
tattaggaaa gttaatatag tgtcttggtt attctaatgg agtgggttat gcaaattaag     720
```

|                                                              |      |
|--------------------------------------------------------------|------|
| ttcccttntc aaagtttggt ttatgaactg ctccactcnt gtccctctta aaagccttaa | 780  |
| tcccaacatg taccaccaaa gaantgagct gctccatcag atcctttgag aatgttaata | 840  |
| tgttatttaa atgaaggact gaatgattat gaggatgcaa tgcataggtt taattaccag | 900  |
| ttatctgtaa attgtcttcn ttgccattat tttaaaagtt taatnnnaag tgtaacatct | 960  |
| acaaagagtt gataattaca aagcagctac tagttttag                   | 1000 |

```
<210> SEQ ID NO 29
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 29
```

|                                                              |     |
|--------------------------------------------------------------|-----|
| tagagtttgg aatggtttgt ggccttcgga tagaagacgt gttagagaat gttattgttt | 60  |
| cggaatggag actttgttga agcttgattt ggaaggtact aggagattgt ttgatgcttt | 120 |
| ctttgatgtt gatcccaagt actggcacgg gttcctttct tcaagattgt ctgtcaaaga | 180 |
| acttgctgta ctcagtttgt accttttgg acatgcctct aatttggcta ggttggatat | 240 |
| tgttacaaag tgcactgtcc ccttggttaa actgctgggc aatctagcaa tagagagcct | 300 |
| ttgaattaat atgatagttt tgaagcactg ntttcatttt aatttcttag gttattttca | 360 |
| tcttttntca atgcaaaagt gaaacaaaag ctatacacat tgtcatcgtt gttcaaactc | 420 |

```
agacaagttt gcctagctct atgtatttat ccttaacata tgtattcatc aaattcgaaa    480
tatacaatgn nnnnnnnnnn nnncattgga caaaagtata gagccacaat cngataccaa    540
gtctgtattt ggaagcacng kctaattgtt atggttacca aacactttga attggctgga    600
taataacann nnggaantt t atgttattaa tcattaacag caaattggga aagcaagaat    660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagtttttag                         1000
```

<210> SEQ ID NO 30
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (612)..(612)
<223> OTHER INFORMATION: A may be either A or a deletion
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 30

```
tagagtttgg aatggtttgt ggccttcgga tagaagacgt gttagagaat gttattgttt    60
cggaatggag actttgttga agcttgattt ggaaggtact aggagattgt ttgatgcttt   120
ctttgatgtt gatcccaagt actggcacgg gttcctttct tcaagattgt ctgtcaaaga   180
acttgctgta ctcagtttgt acctttttgg acatgcctct aatttggcta ggttggatat   240
tgttacaaag tgcactgtcc ccttggttaa actgctgggc aatctagcaa tagagagcct   300
ttgaattaat atgatagttt tgaagcactg nttcatttt aatttcttag gttattttca   360
tcttttntca atgcaaaagt gaaacaaaag ctatacacat tgtcatcgtt gttcaaactc   420
agacaagttt gcctagctct atgtatttat ccttaacata tgtattcatc aaattcgaaa   480
tatacaatgn nnnnnnnnn nnncattgga caaaagtata gagccacaat cngataccaa   540
gtctgtattt ggaagcacng nctaattgtt atggttacca aacactttga attggctgga   600
taataacaaa caggaanttt atgttattaa tcattaacag caaattggga aagcaagaat   660
tattaggaaa gttaatatag tgtcttggtt attctaatgg agtgggttat gcaaattaag   720
ttcccttntc aaagtttggt ttatgaactg ctccactcnt gtccctctta aaagccttaa   780
tcccaacatg taccaccaaa gaantgagct gctccatcag atcctttgag aatgttaata   840
tgttatttaa atgaaggact gaatgattat gaggatgcaa tgcataggtt taattaccag   900
ttatctgtaa attgtcttcn ttgccattat tttaaaagtt taatnnnaag tgtaacatct   960
acaaagagtt gataattaca aagcagctac tagttttag                        1000
```

<210> SEQ ID NO 31
<211> LENGTH: 996
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (613)..(613)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (916)..(916)
<223> OTHER INFORMATION: n is a, c, g, or t
<220> FEATURE:
<221> NAME/KEY: misc_feature
<222> LOCATION: (941)..(943)
<223> OTHER INFORMATION: n is a, c, g, or t

<400> SEQUENCE: 31

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga    180
acttgctgta ctcagtttgt acctttttgg acatgcctct aatttggcta ggttggatat    240
tgttacaaag tgcactgtcc ccttggttaa actgctgggc aatctagcaa tagagagcct    300
ttgaattaat atgatagttt tgaagcactg ntttcatttt aatttcttag gttattttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnnn nnncattgga caaaagtata gagccacaat cngataccaa    540
gtctgtattt ggaagcacng nctaattgtt atggttacca aacactttga attggctgga    600
taataacagg aantttatgt tattaatcat taacagcaaa ttgggaaagc aagaattatt    660
aggaaagtta atatagtgtc ttggttattc taatggagtg ggttatgcaa attaagttcc    720
cttntcaaag tttggtttat gaactgctcc actcntgtcc ctcttaaaag ccttaatccc    780
aacatgtacc accaaagaan tgagctgctc catcagatcc tttgagaatg ttaatatgtt    840
atttaaatga aggactgaat gattatgagg atgcaatgca taggtttaat taccagttat    900
ctgtaaattg tcttcnttgc cattatttta aaagtttaat nnnaagtgta acatctacaa    960
agagttgata attacaaagc agctactagt ttttag                              996
```

<210> SEQ ID NO 32
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)

```
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 32
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga     180
acttgctgta ctcagtttgt acctttttgg acatgcctct aatttggcta ggttggatat     240
tgttacaaag tgcactgtcc ccttggtaa actgctgggc aatctagcaa tagagagcct     300
ttgaattaat atgatagttt tgaagcactg ntttcatttt aatttcttag gttattttca     360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnn nnncattgga caaaagtata gagccacaat cngataccaa     540
gtctgtattt ggaagcacng nctaattgtt atggttacca aacactttga attggctgga     600
taataacann nnggaamttt atgttattaa tcattaacag caaattggga aagcaagaat     660
tattaggaaa gttaatatag tgtcttggtt attctaatgg agtgggttat gcaaattaag     720
ttcccttntc aaagtttggt ttatgaactg ctccactcnt gtccctctta aaagccttaa     780
tcccaacatg taccaccaaa gaantgagct gctccatcag atcctttgag aatgttaata     840
tgttatttaa atgaaggact gaatgattat gaggatgcaa tgcataggtt taattaccag     900
ttatctgtaa attgtcttcn ttgccattat tttaaaagtt taatnnnaag tgtaacatct     960
acaaagagtt gataattaca aagcagctac tagtttttag                         1000

<210> SEQ ID NO 33
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
```

<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 33

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga     180
acttgctgta ctcagtttgt accttttggg acatgcctct aatttggcta ggttggatat     240
tgttacaaag tgcactgtcc ccttggttaa actgctgggc aatctagcaa tagagagcct     300
ttgaattaat atgatagttt tgaagcactg ntttcatttt aatttcttag gttattttca     360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnnn nnncattgga caaaagtata gagccacaat cngataccaa     540
gtctgtattt ggaagcacng nctaattgtt atggttacca acactttga attggctgga     600
taataacann nnggaanttt atgttattaa tcattaacag caaattggga aagcaagaat     660
tattaggaaa gttaatatag tgtcttggtt attctaatgg agtgggttat gcaaattaag     720
ttcccttrtc aaagtttggt ttatgaactg ctccactcnt gtccctctta aaagccttaa     780
tcccaacatg taccaccaaa gaantgagct gctccatcag atcctttgag aatgttaata     840
tgttatttaa atgaaggact gaatgattat gaggatgcaa tgcataggtt taattaccag     900
ttatctgtaa attgtcttcn ttgccattat tttaaaagtt taatnnnaag tgtaacatct     960
acaaagagtt gataattaca aagcagctac tagttttag                           1000
```

<210> SEQ ID NO 34
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:

```
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 34
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttccttttct tcaagattgt ctgtcaaaga    180
acttgctgta ctcagtttgt acctttttgg acatgcctct aatttggcta ggttggatat     240
tgttacaaag tgcactgtcc ccttggttaa actgctgggc aatctagcaa tagagagcct     300
ttgaattaat atgatagttt tgaagcactg ntttcatttt aatttcttag gttattttca     360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnnn nnncattgga caaaagtata gagccacaat cngataccaa     540
gtctgtattt ggaagcacng nctaattgtt atgttaccaa acactttga attggctgga     600 taataacann nnggaantttt atgttattaa tcattaacag caaattggga aagcaagaat     660
tattaggaaa gttaatatag tgtcttggtt attctaatgg agtgggttat gcaaattaag     720
ttcccttntc aaagtttggt ttatgaactg ctccactckt gtccctctta aaagccttaa     780
tcccaacatg taccaccaaa gaantgagct gctccatcag atcctttgag aatgttaata     840
tgttatttaa atgaaggact gaatgattat gaggatgcaa tgcataggtt aattaccag      900 ttatctgtaa attgtcttcn ttgccattat tttaaaagtt taatnnnaag tgtaacatct     960
acaaagagtt gataattaca aagcagctac tagtttttag                          1000
```

```
<210> SEQ ID NO 35
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 35
tagagtttgg aatggtttgt ggccttcgga tagaagacgt gttagagaat gttattgttt     60
cggaatggag actttgttga agcttgattt ggaaggtact aggagattgt ttgatgcttt    120
ctttgatgtt gatcccaagt actggcacgg gttcctttct tcaagattgt ctgtcaaaga    180
acttgctgta ctcagtttgt accttttggg acatgcctct aatttggcta ggttggatat    240
tgttacaaag tgcactgtcc ccttggttaa actgctgggc aatctagcaa tagagagcct    300
ttgaattaat atgatagttt tgaagcactg ntttcatttt aatttcttag gttattttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnnn nnncattgga caaaagtata gagccacaat cngataccaa    540
gtctgtattt ggaagcacng nctaattgtt atggttacca aacactttga attggctgga    600
taataacann nnggaantttt atgttattaa tcattaacag caaattggga aagcaagaat    660
```

```
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaaytgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagtttttag                         1000

<210> SEQ ID NO 36
<211> LENGTH: 1000
<212> TYPE: DNA
<213> ORGANISM: Capsicum annum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 36
tagagtttgg aatggtttgt ggccttcgga tagaagacgt gttagagaat gttattgttt     60
cggaatggag actttgttga agcttgattt ggaaggtact aggagattgt ttgatgcttt    120
ctttgatgtt gatcccaagt actggcacgg gttccttttct tcaagattgt ctgtcaaaga    180
acttgctgta ctcagtttgt accttttttgg acatgcctct aatttggcta ggttggatat    240
tgttacaaag tgcactgtcc ccttggttaa actgctgggc aatctagcaa tagagagcct    300
ttgaattaat atgatagttt tgaagcactg ntttcatttt aatttcttag gttattttca    360
```

```
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnnn nnncattgga caaaagtata gagccacaat cngataccaa    540
gtctgtattt ggaagcacng nctaattgtt atggttacca aacactttga attggctgga    600
taataacann nnggaanttt atgttattaa tcattaacag caaattggga aagcaagaat    660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttck ttgccattat tttaaaagtt taatnnnaag tgtaacatct    960
acaaagagtt gataattaca aagcagctac tagttttag                         1000
```

<210> SEQ ID NO 37
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (947)..(947)

<223> OTHER INFORMATION: C may be either C or a deletion

<400> SEQUENCE: 37

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga    180
acttgctgta ctcagtttgt accttttttgg acatgcctct aatttggcta ggttggatat    240
tgttacaaag tgcactgtcc ccttggttaa actgctgggc aatctagcaa tagagagcct    300
ttgaattaat atgatagttt tgaagcactg ntttcatttt aatttcttag gttattttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnn nnncattgga caaaagtata gagccacaat cngataccaa     540
gtctgtattt ggaagcacng nctaattgtt atggttacca aacactttga attggctgga    600
taataacann nnggaanttt atgttattaa tcattaacag caaattggga aagcaagaat    660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taataacaag tgtaacatct    960
acaaagagtt gataattaca aagcagctac tagtttttag                         1000
```

<210> SEQ ID NO 38
<211> LENGTH: 997
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t

```
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t

<400> SEQUENCE: 38
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga     180
acttgctgta ctcagtttgt acctttttgg acatgcctct aatttggcta ggttggatat     240
tgttacaaag tgcactgtcc ccttggttaa actgctgggc aatctagcaa tagagagcct     300
ttgaattaat atgatagttt tgaagcactg ntttcatttt aatttcttag gttattttca     360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnnn nnncattgga caaaagtata gagccacaat cngataccaa     540
gtctgtattt ggaagcacng nctaattgtt atggttacca aacactttga attggctgga     600
taataacann nnggaanttt atgttattaa tcattaacag caaattggga aagcaagaat     660
tattaggaaa gttaatatag tgtcttggtt attctaatgg agtgggttat gcaaattaag     720
ttcccttntc aaagtttggt ttatgaactg ctccactcnt gtccctctta aaagccttaa     780
tcccaacatg taccaccaaa gaantgagct gctccatcag atcctttgag aatgttaata     840
tgttatttaa atgaaggact gaatgattat gaggatgcaa tgcataggtt taattaccag     900
ttatctgtaa attgtcttcn ttgccattat tttaaaagtt taataagtgt aacatctaca     960
aagagttgat aattacaaag cagctactag tttttag                              997

<210> SEQ ID NO 39
<211> LENGTH: 14
<212> TYPE: DNA
<213> ORGANISM: Capsicum annuum

<400> SEQUENCE: 39
tatggttgtc gatg                                                        14

<210> SEQ ID NO 40
<211> LENGTH: 5736
<212> TYPE: DNA
<213> ORGANISM: Capsicum annuum

<400> SEQUENCE: 40
tgttgaatgg aaaatattgg aagaatttca tttcatttta caaaaataaa gagtgtagag      60 ggtattttg taaatcaata tttttctat aaaaaatata taagaaatat tattttaata      120
catcaaatca aatactgtat aagaaataat gttaacataa ttaatgcaag tatagctaat     180
accaacatta ctaatgcaag tattactaat acaccatatt ctatattaat cttatatact     240
ctaccaaacg accctaagtg tgtatctata tcctccgaga atttggaatt tgcaaattcc     300
aagttttgta tctccctttc ccagaaatta agataattct ggtgctttta gcattagaaa     360
```

```
agtatttatt gggtagggaa atgtcatgac ttcacagcat taagcatcaa gggtataact      420
taatgaaata gtggtcaatg aattatattg agaatgacga ggtctctgtt ccaactttgg      480
tagactttgg aaatgctcgt ctggacgccg cccattcttt ctagtcttgg tgccattcta      540
tttggtctga gactggcatg atgccaaatt ctaaccttt cacaatgagc attcgaccta      600
ctcttctttt ttacgactct atttgaccta ctaggcattg gccaacttgg ctaaccactt      660
gaggaactag agttcggatt caatagaatc taataatttt aatcaaaaga cttcatgtat      720
attgaaaaat ctatttataa ctaactttaa atcggccttt acgtatcgac gtaatcaaaa      780
ttgtgtcagc ttgccacgtg gggtctagta tgagtttgaa attggtcata ggggccccaa      840
ttccactaat acagctgccg tccatgcact acaagacaaa tacaccacta tgtttgttag      900
tgcttggtaa atgtaaaaca aacttttgat gagaatctat tcgtggcatc gaagtgctgc      960
aaattggctt ttacctctgc tacttcaagc ctcactgatt ttcaccccaa ctttctcatt     1020
tcccttccaa ggatttgatt ttccagttgg gcatgttaaa aacaacaatt ttcctcaaaa     1080
ctgtagaaat gatttctcat attttaatca gtcaaattat ttaaacaaga agttgatttt     1140
tttttaattt tttttttttac aaaaaaattt caaatgtcaa gtaagatttt tcaaattgaa     1200
actgaataag ctgcgacttt agaaacaaaa aactaagata agtaaaaata ccaaaaagag     1260
tgaatcacat caattgaatt cttccaacag ttcgttttttt agtttctgtt ttgggaagag     1320
gagtactaca aggtaggacc tccaacaatc aacaatatct aagttgcaaa agttttgtg     1380 cgttttttag tttctgtttc gagaagagga atactacaag ttcgtttttt agtttctgtt     1440
ttgggaagag gagtactgca aggtaggacc tccaacaatt atcaatatct aaattgcaaa     1500
aatttcagtt cgtttttagt ttctgtttcg ggaagaggaa tactacaagt tcgttttttta     1560 gtttctattt tgggaagagg agtactacaa ggtaggacct ccaataccta aattgcaaaa     1620
atttcagttc gttttttagt ttcagtttag ggaagaggaa tactacaagg taggacctcc     1680
aacaatcatc agtacctaaa ttgcaaaaat ttcagttcgt tttttagttt atgtttggga     1740
agaagaatac tacaaggcag tggcggagct accttatgat tagggggttc atccgaacct     1800
ccttcgacgg aaaattatac tattttttata agtgaaaatt atttttttatg tatatataat     1860 tgatgttgaa ccccttcgg ttagttcatg tatctatatt ttttttatttt gaacccccgat     1920 gaaaattttg gctccgccac tgctacaagg taggacctcc aacaatcacc aatacctaaa     1980
ttgcaaaaat ttcagtttgt tttttagttt ctgttttggg aagaggaata ctacaaggta     2040
ggacctccaa caatcaccaa tacctaaatt gcaacgtttt tttagtttct gttttgggaa     2100
gaggaatact acatggtagg gcctccaaca atcaccaata cctaaattgc aaaaatttca     2160
gttcgtattt tcgtttctat tttgggaagt ggaatagtat aagtaggac ctccaacaat     2220 caccaatacc taaattaaag ttccgattca tttttagtt tctgttttgg aaagagaaat     2280
actacaaggt agggcctaca acaatcacca gtacctaaat tgtaaaaatt tcagttcgtt     2340
ttttagtttc tattttgaga agaggaatgc tacaaggtag ggcctacaac aatcaccagt     2400
acctaaattg taaaaatttc agttcgtttt ttagtttctg ttttgggaag aggaatacta     2460
caaggtaggg ccttcaacaa tcagcaatac ctaaattaca aaaatttcaa ttcgtttttt     2520
agtttctgtt ttgggaagag gaatactaca aggcagtggc ggagctacct tatgattagg     2580
ggttcatccg aacctccttc gacgaaaat tatactattt ttatatagta aaaattattt     2640
tttatgtata taattgat gttgaacccc cttcggttag tttgtgtatc tatattttt     2700 tattttgaac ctccttgata aaaattttg actccgccat tgctacaagg tagaacctcc     2760
```

```
aacaatcacc aataaactaaa ttgcaaaaat ttcagttcgt tttttaattt ctgttttggg    2820
aagaggaata ctacaaggcc tccaacaatc accaatacct aaattgcaaa aatttcagtt    2880
tgttttttag tttctgtttt gggaagagga atactacaag gtaaggcctc caacaatcac    2940
caatacctaa attgcaaaaa tttcagttcg tattttcgtt tctatttggg gaagtggaat    3000
agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttcttttttt    3240
agtttctgtt ttggaaagag aaatactaca agataggacc ttcaacaatc accaatacct    3300
aaattgcaaa aacttcagtt catttttag tttctgtttt gggaagaaga atacttcaag    3360
gtaacaatca ccaatacctt aattaaattt cagttagttt tttagtttct gttttttgga    3420
agaggaatac tttcttttgc tatataaagc caaagtaggt acctataagc atcaatattt    3480
tgtattgctt agtgattccc ctagttcggt atttcatttt ttttcactat actatatcac    3540
ctcctctcat aaatagccat tataaatctt gcattttctc taatgaaaac ccttctaaag    3600
ccttttccat ctcctttact ttccattcct actcctaaca tgtatagttt caaacacaac    3660 tccactttc caaatccaac caaacaaaaa gattcaagaa agttccatta tagaaacaaa    3720
agcagtacac attttgtag cttctttgat ttagcaccca catcaaagcc agagtcttta    3780
gatgttaaca tctcatgggt tgatactgat ctggacgggg ctgaattcga cgtgatcatc    3840
attggaactg gccctgccgg gcttcggcta gctgaacaag tttctaaata tggtattaag    3900
gtatgttgcg ttgaccccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat tggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gcggtagctt gattgttgat gcaagtggct atgctagtga ttttatagag    4260
tatgacaagc caagaaacca tggttatcaa gttgctcatg ggatttagc agaagttgat    4320 aatcatccat ttgatttgga taaaatgatg cttatggatt ggagggattc tcatttaggt    4380
aatgagccat atctgagggt gaagaatact aaagaaccaa cattcttgta tgcaatgcca    4440
tttgatagga attttggtatt cttggaagag acttctttag tgagtcggcc tatgttatcg    4500
tatatggaag tgaaaagaag gatggtagca agattaagac atttggggat caaagtgaga    4560
agtgtccttg aggaagagaa gtgtgtgatc actatgggag gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag tttggaatgg tttgtggcct    4800
tcggatagaa gacgtgttag agaatgttat tgtttcggaa tggagacttt gttgaagctt    4860
gatttggaag gtactaggag attgtttgat gctttctttg atgttgatcc caagtactgg    4920
cacgggttcc tttcttcaag attgtctgtc aaagaacttg ctgtactcag tttgtacctt    4980
tttggacatg cctctaattt ggctaggttg gatattgtta caagtgcac tgtcccttg    5040 gttaaactgc tgggcaatct agcaatagag agcctttgaa ttaatatgat agttttgaag    5100
```

-continued

| | |
|---|---|
| cactgttttc attttaattt cttaggttat tttcatcttt tctcaatgca aaagtgaaac | 5160 |
| aaaagctata cacattgtca tcgttgttca aactcagaca agtttgccta gctctatgta | 5220 |
| tttatcctta acatatgtat tcatcaaatt cgaaatatac aatgcattgg acaaaagtat | 5280 |
| agagccacaa tccgatacca agtctgtatt tggaagcact gtctaattgt tatggttacc | 5340 |
| aaacactttg aattggctgg ataataacaa acaggaaatt tatgttttta atcattaaca | 5400 |
| gcaaattggg aaagcaagaa ttattaggaa agttaatata gtgtcttggt tattctaatg | 5460 |
| gagtgggtta tgcaaattaa gttcccttat caaagtttgg tttatgaact gctccactct | 5520 |
| tgtccctctt aaaagcctta atcccaacat gtaccaccaa agaattgagc tgctccatca | 5580 |
| gatcctttga gaatgttaat atgttattta aatgaaggac tgaatgatta tgaggatgca | 5640 |
| atgcataggt ttaattacca gttatctgta aattgtcttc tttgccatta ttttaaaagt | 5700 |
| ttaataacaa gtgtaacatc tacaaagagt tgataa | 5736 |

<210> SEQ ID NO 41
<211> LENGTH: 5736
<212> TYPE: DNA
<213> ORGANISM: Capsicum annuum

<400> SEQUENCE: 41

| | |
|---|---|
| tgttgaatgg aaaatattgg aagaatttca tttcatttta caaaaataaa gagtgtagag | 60 |
| ggtatttttg taaatcaata ttttttctat aaaaaatata taagaaatat tattttaata | 120 |
| catcaaatca aatactgtat aagaaataat gttaacataa ttaatgcaag tatagctaat | 180 |
| accaacatta ctaatgcaag tattactaat acaccatatt ctatattaat cttatatact | 240 |
| ctaccaaacg accctaagtg tgtatctata tcctccgaga atttggaatt tgcaaattcc | 300 |
| aagttttgta tctcccttc ccagaaatta agataattct ggtgctttta gcattagaaa | 360 |
| agtatttatt gggtagggaa atgtcatgac ttcacagcat taagcatcaa gggtataact | 420 |
| taatgaaata gtggtcaatg aattatattg agaatgacga ggtctctgtt ccaactttgg | 480 |
| tagactttgg aaatgctcgt ctggacgccg cccattcttt ctagtcttgg tgccattcta | 540 |
| tttggtctga gactggcatg atgccaaatt ctaacctttt cacaatgagc attcgaccta | 600 |
| ctcttctttt ttacgactct atttgaccta ctaggcattg gccaacttgg ctaaccactt | 660 |
| gaggaactag agttcggatt caatagaatc taataatttt aatcaaaaga cttcatgtat | 720 |
| attgaaaaat ctatttataa ctaactttaa atcggccttt acgtatcgac gtaatcaaaa | 780 |
| ttgtgtcagc ttgccacgtg gggtctagta tgagtttgaa attggtcata ggggccccaa | 840 |
| ttccactaat acagctgccg tccatgcact acaagacaaa tacaccacta tgtttgttag | 900 |
| tgcttggtaa atgtaaaaca aacttttgat gagaatctat tcgtggcatc gaagtgctgc | 960 |
| aaattggctt ttacctctgc tacttcaagc ctcactgatt ttcaccccaa ctttctcatt | 1020 |
| tccctttcaa ggatttgatt ttccagttgg gcatgttaaa aacaacaatt ttcctcaaaa | 1080 |
| ctgtagaaat gatttctcat attttaatca gtcaaattat ttaaacaaga agttgatttt | 1140 |
| tttttaattt tttttttttac aaaaaaattt caaatgtcaa gtaagatttt tcaaattgaa | 1200 |
| actgaataag ctgcgacttt agaaacaaaa aactaagata agtaaaaata ccaaaaagag | 1260 |
| tgaatcacat caattgaatt cttccaacag ttcgtttttt agtttctgtt ttgggaagag | 1320 |
| gagtactaca aggtaggacc tccaacaatc aacaatatct aagttgcaaa agttttttgtg | 1380 |
| cgtttttttag tttctgtttc gagaagagga atactacaag ttcgtttttt agtttctgtt | 1440 |
| ttgggaagag gagtactgca aggtaggacc tccaacaatt atcaatatct aaattgcaaa | 1500 |

```
aatttcagtt cgttttttagt ttctgtttcg ggaagaggaa tactacaagt tcgtttttta   1560
gtttctattt tgggaagagg agtactacaa ggtaggacct ccaatacccta aattgcaaaa   1620 atttcagttc gttttttagt ttcagtttag ggaagaggaa tactacaagg taggacctcc   1680
aacaatcatc agtacctaaa ttgcaaaaat ttcagttcgt tttttagttt atgtttggga   1740
agaagaatac tacaaggcag tggcggagct accttatgat tagggggttc atccgaacct   1800
ccttcgacgg aaaattatac tatttttata agtgaaaatt attttttatg tatatataat   1860
tgatgttgaa cccccttcgg ttagttcatg tatctatatt tttttatttt gaaccccgat   1920
gaaaattttg gctccgccac tgctacaagg taggacctcc aacaatcacc aatacctaaa   1980
ttgcaaaaat ttcagtttgt tttttagttt ctgttttggg aagaggaata ctacaaggta   2040
ggacctccaa caatcaccaa tacctaaatt gcaacgtttt tttagtttct gttttgggaa   2100
gaggaatact acatggtagg gcctccaaca atcaccaata cctaaattgc aaaaatttca   2160
gttcgtattt tcgtttctat tttgggaagt ggaatagtat aaggtaggac tccaacaat   2220 caccaatacc taaattaaag ttccgattca tttttttagtt tctgttttgg aaagagaaat   2280
actacaaggt agggcctaca acaatcacca gtacctaaat tgtaaaaatt tcagttcgtt   2340
ttttagtttc tattttgaga agaggaatgc tacaaggtag ggcctacaac aatcaccagt   2400
acctaaattg taaaaatttc agttcgtttt tagttctg ttttgggaag aggaatacta   2460
caaggtaggg ccttcaacaa tcagcaatac ctaaattaca aaaatttcaa ttcgttttt   2520 agtttctgtt ttgggaagag gaatactaca aggcagtggc ggagctacct tatgattagg   2580
ggttcatccg aacctccttc gacggaaaat tatactattt ttatatagta aaaattattt   2640
tttatgtata taattgat gttgaacccc cttcggttag tttgtgtatc tatatttttt   2700
tattttgaac ctccttgata aaaaattttg actccgccat tgctacaagg tagaacctcc   2760
aacaatcacc aatacctaaa ttgcaaaaat ttcagttcgt tttttaattt ctgttttggg   2820
aagaggaata ctacaaggcc tccaacaatc accaatacct aaattgcaaa aatttcagtt   2880
tgttttttag tttctgtttt gggaagagga atactacaag gtaaggcctc caacaatcac   2940
caatacctaa attgcaaaaa tttcagttcg tatttttcgtt tctatttggg gaagtggaat   3000
agtataaggt aggacctcca acaatcacca atacctaaat tgcaaaagtt ccgattcatt   3060
ttttagtttc tgttttggaa agagaaatac tacaaggtag ggtctccaac aatcaccagt   3120
acctaaattg taaaaatttc agttcgtttt tagtttcta ttttgggaag tggaatagta   3180
taaggtagga cctccaacaa tcaccaatac ctaaattgca aaagtccga ttctttttt   3240 agtttctgtt ttgggaagag aaatactaca agataggacc ttcaacaatc accaatacct   3300
aaattgcaaa aacttcagtt catttttag tttctgtttt gggaagaaga atacttcaag   3360
gtaacaatca ccaatacctta aattaaattt cagttagttt tttagtttct gttttggga   3420 agaggaatac tttcttttgc tatataaagc caaagtaggt acctataagc atcaatattt   3480
tgtattgctt agtgattccc ctagttcggt atttcatttt ttttcactat actatatcac   3540
ctcctctcat aaatagccat tataaatctt gcatttctc taatggaaac ccttctaaag   3600 cctttttccat ctcctttact ttccattcct actcctaaca tgtatagttt caaacacaac   3660
tccacttttc caaatccaac caaacaaaaa gattcaagaa agttccatta tagaaacaaa   3720
agcagtacac attttgtag ctttcttgat ttagcaccca catcaaagcc agagtcttta   3780
gatgttaaca tctcatgggt tgatactgat ctggacgggg ctgaattcga cgtgatcatc   3840
```

| | | | | |
|---|---|---|---|---|
| attggaactg | gccctgccgg | gcttcggcta | gctgaacaag | tttctaaata tggtattaag | 3900 |
| gtatgttgcg | ttgacccttc | accactttcc | atgtggccaa | ataattatgg tgtttgggtt | 3960 |
| gatgagtttg | aaaagttggg | attagaagat | tgtctagatc | ataagtggcc tgtgagttgt | 4020 |
| gttcatataa | gtgatcacaa | gactaagtat | ttggacagac | catatggtag agtaagtaga | 4080 |
| aagaagttga | agttgaaatt | gttgaatagt | tgtgttgaaa | atagagtgaa gttttataaa | 4140 |
| gccaaggttt | tgaaagtgaa | gcatgaagaa | tttgagtctt | cgattgtttg tgatgatggt | 4200 |
| aggaagataa | gcggtagctt | gattgttgat | gcaagtggct | atgctagtga ttttatagag | 4260 |
| tatgacaagc | caagaaacca | tggttatcaa | gttgctcatg | ggattttagc agaagttgat | 4320 |
| aatcatccat | ttgatttgga | taaaatgatg | cttatggatt | ggagggattc tcatttaggt | 4380 |
| aatgagccat | atctgagggt | gaagaatact | aaagaaccaa | cattcttgta tgcaatgcca | 4440 |
| tttgatagga | atttggtatt | cttggaagag | acttctttag | tgagtcggcc tatgttatcg | 4500 |
| tatatggaag | tgaaaagaag | gatggtagca | agattaagac | atttggggat caaagtgaga | 4560 |
| agtgtccttg | aggaagagaa | gtgtgtgatc | actatgggag | gaccacttcc gcggattcct | 4620 |
| caaaatgtta | tggctattgg | tgggacttca | gggatagttc | atccatcgtc tgggtacatg | 4680 |
| gtggctcgta | gcatggcatt | ggcaccagta | ctggctgagg | ccatcgtcga aagccttggc | 4740 |
| tcaacaagaa | tgataagagg | gtctcaactt | taccatagag | tttggaatgg tttgtggcct | 4800 |
| tcggatagaa | gacgtgttag | agaatgttat | tgtttcggaa | tggagacttt gttgaagctt | 4860 |
| gatttggaag | gtactaggag | attgtttgat | gctttctttg | atgttgatcc caagtactgg | 4920 |
| cacgggttcc | tttcttcaag | attgtctgtc | aaagaacttg | ctgtactcag tttgtacctt | 4980 |
| tttggacatg | cctctaattt | ggctaggttg | gatattgtta | caaagtgcac tgtccccttg | 5040 |
| gttaaactgc | tgggcaatct | agcaatagag | agcctttgaa | ttaatatgat agttttgaag | 5100 |
| cactgttttc | attttaattt | cttaggttat | tttcatcttt | tctcaatgca aaagtgaaac | 5160 |
| aaaagctata | cacattgtca | tcgttgttca | aactcagaca | agtttgccta gctctatgta | 5220 |
| tttatcctta | acatatgtat | tcatcaaatt | cgaaatatac | aatgcattgg acaaaagtat | 5280 |
| agagccacaa | tccgatacca | agtctgtatt | tggaagcact | gtctaattgt tatggttacc | 5340 |
| aaacactttg | aattggctgg | ataataacaa | acaggaaatt | tatgttttta atcattaaca | 5400 |
| gcaaattggg | aaagcaagaa | ttattaggaa | agttaatata | gtgtcttggt tattctaatg | 5460 |
| gagtgggtta | tgcaaattaa | gttcccttat | caaagtttgg | tttatgaact gctccactct | 5520 |
| tgtccctctt | aaaagcctta | atcccaacat | gtaccaccaa | agaattgagc tgctccatca | 5580 |
| gatcctttga | aatgttaat | atgttattta | aatgaaggac | tgaatgatta tgaggatgca | 5640 |
| atgcataggt | ttaattacca | gttatctgta | aattgtcttc | tttgccatta ttttaaaagt | 5700 |
| ttaataacaa | gtgtaacatc | tacaaagagt | tgataa | | 5736 |

<210> SEQ ID NO 42
<211> LENGTH: 5736
<212> TYPE: DNA
<213> ORGANISM: Capsicum annuum

<400> SEQUENCE: 42

| | | | | |
|---|---|---|---|---|
| tgttgaatgg | aaaatattgg | aagaatttca | tttcatttta | caaaaataaa gagtgtagag | 60 |
| ggtatttttg | taaatcaata | ttttttctat | aaaaaatata | taagaaatat tattttaata | 120 |
| catcaaatca | aatactgtat | aagaaataat | gttaacataa | ttaatgcaag tatagctaat | 180 |
| accaacatta | ctaatgcaag | tattactaat | acaccatatt | ctatattaat cttatatact | 240 |

```
ctaccaaacg accctaagtg tgtatctata tcctccgaga atttggaatt tgcaaattcc    300
aagttttgta tctcccttc ccagaaatta agataattct ggtgctttta gcattagaaa    360
agtatttatt gggtagggaa atgtcatgac ttcacagcat taagcatcaa gggtataact    420
taatgaaata gtggtcaatg aattatattg agaatgacga ggtctctgtt ccaactttgg    480
tagactttgg aaatgctcgt ctggacgccg cccattcttt ctagtcttgg tgccattcta    540
tttggtctga gactggcatg atgccaaatt ctaaccttt cacaatgagc attcgaccta    600
ctcttctttt ttacgactct atttgaccta ctaggcattg gccaacttgg ctaaccactt    660
gaggaactag agttcggatt caatagaatc taataatttt aatcaaaaga cttcatgtat    720
attgaaaaat ctatttataa ctaactttaa atcggccttt acgtatcgac gtaatcaaaa    780
ttgtgtcagc ttgccacgtg gggtctagta tgagtttgaa attggtcata ggggccccaa    840
ttccactaat acagctgccg tccatgcact acaagacaaa tacaccacta tgtttgttag    900
tgcttggtaa atgtaaaaca aacttttgat gagaatctat tcgtggcatc gaagtgctgc    960
aaattggctt ttacctctgc tacttcaagc ctcactgatt ttcaccccaa ctttctcatt   1020 tcccttcaa ggatttgatt ttccagttgg gcatgttaaa aacaacaatt ttcctcaaaa   1080
ctgtagaaat gatttctcat atttaatca gtcaaattat ttaaacaaga agttgattt   1140 ttttaattt tttttttac aaaaaaattt caaatgtcaa gtaagatttt tcaaattgaa   1200
actgaataag ctgcgacttt agaaacaaaa aactaagata agtaaaaata ccaaaaagag   1260
tgaatcacat caattgaatt cttccaacag ttcgttttt agtttctgtt ttgggaagag   1320
gagtactaca aggtaggacc tccaacaatc aacaatatct aagttgcaaa agttttgtg   1380 cgttttttag tttctgtttc gagaagagga atactacaag ttcgtttttt agtttctgtt   1440
ttgggaagag gagtactgca aggtaggacc tccaacaatt atcaatatct aaattgcaaa   1500
aatttcagtt cgttttagt ttctgtttcg gaagaggaa tactacaagt tcgtttttta   1560
gtttctattt tgggaagagg agtactacaa ggtaggacct ccaataccta aattgcaaaa   1620
atttcagttc gtttttagt ttcagttag ggaagaggaa tactacaagg taggacctcc   1680
aacaatcatc agtacctaaa ttgcaaaaat ttcagttcgt ttttagttt atgtttggga   1740 agaagaatac tacaaggcag tggcggagct accttatgat taggggttc atccgaacct   1800 ccttcgacgg aaaattatac tatttttata agtgaaaatt atttttatg tatatataat   1860 tgatgttgaa ccccttcgg ttagttcatg tatctatatt ttttatttt gaaccccgat   1920 gaaaatttg gctccgccac tgctacaagg taggacctcc aacaatcacc aatacctaaa   1980
ttgcaaaaat ttcagtttgt ttttagttt ctgttttggg agaggaata ctacaaggta   2040 ggacctccaa caatcaccaa tacctaaatt gcaacgtttt tttagtttct gttttgggaa   2100
gaggaatact acatggtagg gcctccaaca atcaccaata cctaaattgc aaaaatttca   2160
gttcgtattt tcgtttctat tttgggaagt ggaatagtat aagtaggac ctccaacaat   2220 caccaatacc taaattaaag ttccgattca ttttttagtt tctgttttgg aaagagaaat   2280
actacaaggt agggcctaca acaatcacca gtacctaaat tgtaaaaatt tcagttcgtt   2340 ttttagttc tattttgaga agaggaatgc tacaaggtag gcctacaac aatcaccagt   2400 acctaaattg taaaaatttc agttcgtttt ttagtttctg ttttgggaag aggaatacta   2460
caaggtaggg ccttcaacaa tcagcaatac ctaaattaca aaaatttcaa ttcgtttttt   2520
agtttctgtt ttgggaagag gaatactaca aggcagtggc ggagctacct tatgattagg   2580
```

```
ggttcatccg aacctccttc gacggaaaat tatactatttt ttatatagta aaaattattt    2640
tttatgtata tataattgat gttgaacccc cttcggttag tttgtgtatc tatattttt     2700 tattttgaac ctccttgata aaaattttg  actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaatacct aaattgcaaa aatttcagtt    2880
tgttttttag tttctgtttt gggaagagga atactacaag gtaaggcctc caacaatcac    2940
caatacctaa attgcaaaaa tttcagttcg tattttcgtt tctatttggg gaagtggaat    3000
agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttctttttt     3240 agttctgtt ttggaaagag aaatactaca agataggacc ttcaacaatc accaatacct    3300
aaattgcaaa aacttcagtt catttttag tttctgtttt gggaagaaga atacttcaag     3360
gtaacaatca ccaatacctaa attaaattt  cagttagttt tttagtttct gttttgga     3420 agaggaatac tttctttgc  tatataaagc caaagtaggt acctataagc atcaatattt    3480
tgtattgctt agtgattccc ctagttcggt atttcatttt tttcactat actatatcac     3540 ctcctctcat aaatagccat tataaatctt gcattttctc taatgaaaac ccttctaaag    3600 cctttttccat ctcctttact ttccattcct actcctaaca tgtatagttt caaacacaac    3660 tccactttc caaatccaac caaacaaaaa gattcaagaa agttccatta tagaaacaaa    3720
agcagtacac attttttgtag ctttcttgat ttagcaccca catcaaagcc agagtcttta    3780
gatgttaaca tctcatgggt tgatactgat ctggacgggg ctgaattcga cgtgatcatc    3840
attggaactg gccctgccgg gcttcggcta gctgaacaag tttctaaata tggtattaag    3900
gtatgttgcg ttgacccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat tggacagac  catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gcggtagctt gattgttgat gcaagtggct atgctagtga ttttatagag    4260
tatgacaagc caagaaacca tggttatcaa gttgctcatg ggattttagc agaagttgat    4320
aatcatccat ttgatttgga taaaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttctttag tgagtcggcc tatgttatcg    4500
tatatggaag tgaaaagaag gatggtagca agattaagac atttggggat caaagtgaga    4560
agtgtccttg aggaagagaa gtgtgtgatc actatgggag gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag tttggaatgg tttgtggcct    4800
tcggatagaa gacgtgttag agaatgttat tgtttcggaa tggagacttt gttgaagctt    4860
gatttggaag gtactaggag attgtttgat gctttctttg atgttgatcc caagtactgg    4920
cacgggttcc tttcttcaag attgtctgtc aaagaacttg ctgtactcag tttgtacctt    4980
```

```
tttggacatg cctctaattt ggctaggttg gatattgtta caaagtgcac tgtcccttg      5040 gttaaactgc tgggcaatct agcaatagag agcctttgaa ttaatatgat agttttgaag     5100
cactgttttc attttaattt cttaggttat tttcatcttt tctcaatgca aaagtgaaac     5160
aaaagctata cacattgtca tcgttgttca aactcagaca agtttgccta gctctatgta     5220
tttatcctta acatatgtat tcatcaaatt cgaaatatac aatgcattgg acaaaagtat     5280
agagccacaa tccgatacca agtctgtatt tggaagcact gtctaattgt tatggttacc     5340
aaacactttg aattggctgg ataataacaa acaggaaatt tatgttttta atcattaaca     5400
gcaaattggg aaagcaagaa ttattaggaa agttaatata gtgtcttggt tattctaatg     5460
gagtgggtta tgcaaattaa gttcccttat caaagtttgg tttatgaact gctccactct     5520
tgtccctctt aaaagcctta atcccaacat gtaccaccaa agaattgagc tgctccatca     5580
gatcctttga gaatgttaat atgttattta aatgaaggac tgaatgatta tgaggatgca     5640
atgcataggt ttaattacca gttatctgta aattgtcttc tttgccatta tttaaaagt      5700 ttaataacaa gtgtaacatc tacaaagagt tgataa                                5736

<210> SEQ ID NO 43
<211> LENGTH: 5736
<212> TYPE: DNA
<213> ORGANISM: Capsicum annuum

<400> SEQUENCE: 43
tgttgaatgg aaaatattgg aagaatttca tttcatttta caaaaataaa gagtgtagag       60
ggtatttttg taaatcaata ttttttctat aaaaaatata taagaaatat tatttaata      120 catcaaatca atactgtat aagaaataat gttaacataa ttaatgcaag tatagctaat       180
accaacatta ctaatgcaag tattactaat acaccatatt ctatattaat cttatatact      240
ctaccaaacg accctaagtg tgtatctata tcctccgaga atttggaatt tgcaaattcc      300
aagttttgta tctcccttc ccagaaatta agataattct ggtgctttta gcattagaaa       360
agtatttatt gggtagggaa atgtcatgac ttcacagcat taagcatcaa gggtataact      420
taatgaaata gtggtcaatg aattatattg agaatgacga ggtctctgtt ccaactttgg      480
tagactttgg aaatgctcgt ctggacgccg cccattcttt ctagtcttgg tgccattcta      540
tttggtctga gactggcatg atgccaaatt ctaaccttt cacaatgagc attcgaccta       600
ctcttctttt ttacgactct atttgaccta ctaggcattg gccaacttgg ctaaccactt      660
gaggaactag agttcggatt caatagaatc taataatttt aatcaaaaga cttcatgtat      720
attgaaaaat ctatttataa ctaactttaa atcggccttt acgtatcgac gtaatcaaaa      780
ttgtgtcagc ttgccacgtg gggtctagta tgagtttgaa attggtcata ggggccccaa      840
ttccactaat acagctgccg tccatgcact acaagacaaa taccactta tgtttgttag       900 tgcttggtaa atgtaaaaca aacttttgat gagaatctat tcgtggcatc gaagtgctgc      960
aaattggctt ttacctctgc tacttcaagc ctcactgatt ttcaccccaa ctttctcatt     1020
tccctttcaa ggatttgatt ttccagttgg gcatgttaaa acaacaatt ttcctcaaaa      1080 ctgtagaaat gatttctcat attttaatca gtcaaattat ttaaacaaga agttgatttt     1140
tttttaattt tttttttac aaaaaaattt caaatgtcaa gtaagatttt tcaaattgaa      1200
actgaataag ctgcgacttt agaaacaaaa aactaagata agtaaaaata ccaaaaagag     1260
tgaatcacat caattgaatt cttccaacag ttcgtttttt agtttctgtt ttgggaagag     1320
```

```
gagtactaca aggtaggacc tccaacaatc aacaatatct aagttgcaaa agtttttgtg    1380
cgttttttag tttctgtttc gagaagagga atactacaag ttcgtttttt agtttctgtt    1440
ttgggaagag gagtactgca aggtaggacc tccaacaatt atcaatatct aaattgcaaa    1500
aatttcagtt cgttttttagt ttctgtttcg ggaagaggaa tactacaagt tcgtttttta    1560 gtttctatttt tgggaagagg agtactacaa ggtaggacct ccaataccta aattgcaaaa    1620
atttcagttc gttttttagt ttcagtttag ggaagaggaa tactacaagg taggacctcc    1680
aacaatcatc agtacctaaa ttgcaaaaat ttcagttcgt tttttagttt atgtttggga    1740
agaagaatac tacaaggcag tggcggagct accttatgat tagggggttc atccgaacct    1800
ccttcgacgg aaaattatac tattttttata agtgaaaatt attttttatg tatatataat    1860
tgatgttgaa cccccttcgg ttagttcatg tatctatatt ttttattttt gaacccccgat    1920 gaaaattttg gctccgccac tgctacaagg taggacctcc aacaatcacc aatacctaaa    1980
ttgcaaaaat ttcagtttgt ttttttagttt ctgttttggg aagaggaata ctacaaggta    2040
ggacctccaa caatcaccaa tacctaaatt gcaacgtttt tttagtttct gttttgggaa    2100
gaggaatact acatggtagg gcctccaaca atcaccaata cctaaattgc aaaaatttca    2160 gttcgtatttt tcgtttctat tttgggaagt ggaatagtat aaggtaggac ctccaacaat    2220
caccaatacc taaattaaag ttccgattca tttttttagtt tctgttttgg aaagagaaat    2280
actacaaggt agggcctaca acaatcacca gtacctaaat tgtaaaaatt tcagttcgtt    2340 ttttagttttc tatttttgaga agaggaatgc tacaaggtag ggcctacaac aatcaccagt    2400
acctaaattg taaaaatttc agttcgtttt ttagtttctg ttttgggaag aggaatacta    2460
caaggtaggg ccttcaacaa tcagcaatac ctaaattaca aaaatttcaa ttcgttttttt    2520 agtttctgtt ttgggaagag gaatactaca aggcagtggc ggagctacct tatgattagg    2580
ggttcatccg aacctccttc gacggaaaat tatactatttt ttatatagta aaaattattt    2640
tttatgtata tataattgat gttgaacccc cttcggttag tttgtgtatc tatattttt    2700 tatttttgaac ctccttgata aaaaattttg actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaatacct aaattgcaaa aatttcagtt    2880
tgttttttag tttctgtttt gggaagagga atactacaag gtaaggcctc aacaatcac    2940 caatacctaa attgcaaaaa tttcagttcg tattttcgtt tctattttgg gaagtggaat    3000
agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttctttttt    3240 agttctgtt ttgggaagag aaatactaca agataggacc ttcaacaatc accaatacct    3300
aaattgcaaa aacttcagtt catttttttag tttctgtttt gggaagaaga atacttcaag    3360
gtaacaatca ccaataccta aattaaattt cagttagttt tttagtttct gttttggga    3420 agaggaatac tttctttgc tatataaagc caaagtaggt acctataagc atcaatattt    3480
tgtattgctt agtgattccc ctagttcggt atttcatttt ttttcactat actatatcac    3540
ctcctctcat aaatagccat tataaatctt gcattttctc taatggaaac ccttctaaag    3600 cctttttccat ctccttttact ttccattcct actcctaaca tgtatagttt caaacacaac    3660
tccacttttc caaatccaac caaacaaaaa gattcaagaa agttccatta tagaaacaaa    3720
```

```
agcagtacac attttttgtag ctttcttgat ttagcaccca catcaaagcc agagtctttta    3780
gatgttaaca tctcatgggt tgatactgat ctggaccggg ctgaattcga cgtgatcatc    3840
attggaactg gccctgccgg gcttcggcta gctgaacaag tttctaaata tggtattaag    3900
gtatgttgcg ttgacccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat ttggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gtggtagctt gattgttgat gcaagtggct atgctagtga ttttatagag    4260
tatgacaagc caagaaacca tggttatcaa gttgctcatg gattttagc agaagttgat     4320
aatcatccat ttgatttgga taaaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttcttttag tgagtcggcc tatgttatcg    4500
tatatgaagg tgaaaagaag gatggtagca agattaagac atttgggat caaagtgaga    4560
agtgtccttg aggaagagaa gtgtgtgatc actatgggag gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag tttggaatgg tttgtggcct    4800
tcggatagaa gacgtgttag agaatgttat tgtttcggaa tggagacttt gttgaagctt    4860
gatttggaag gtactaggag attgtttgat gctttctttg atgttgatcc caagtactgg    4920
cacgggttcc tttcttcaag attgtctgtc aaagaacttg ctgtactcag tttgtaccttt    4980
tttggacatg cctctaattt ggctaggttg gatattgtta caaagtgcac tgtccccttg    5040
gttaaactgc tgggcaatct agcaatagag agcctttgaa ttaatatgat agttttgaag    5100
cactgttttc attttaattt cttaggttat tttcatcttt tctcaatgca aaagtgaaac    5160
aaaagctata cacattgtca tcgttgttca aactcagaca agtttgccta gctctatgta    5220
tttatcctta acatatgtat tcatcaaatt cgaaatatac aatgcattgg acaaaagtat    5280
agagccacaa tctgatacca agtctgtatt tggaagcaca ggctaattgt tatggttacc    5340
aaacactttg aattggctgg ataataacaa acaggaaatt tatgttttta atcattaaca    5400
gcaaattggg aaagcaagaa ttattaggaa agttaatata gtgtcttggt tattctaatg    5460
gagtgggtta tgcaaattaa gttcccttgt caaagtttgg tttatgaact gctccactct    5520
tgtccctctt aaaagcctta atcccaacat gtaccaccaa agaattgagc tgctccatca    5580
gatcctttga gaatgttaat atgttattta aatgaaggac tgaatgatta tgaggatgca    5640
atgcataggt ttaattacca gttatctgta aattgtcttc tttgccatta ttttaaaagt    5700
ttaataacaa gtgtaacatc tacaaagagt tgataa                              5736
```

<210> SEQ ID NO 44
<211> LENGTH: 5743
<212> TYPE: DNA
<213> ORGANISM: Capsicum annuum

<400> SEQUENCE: 44

```
tgttgaatgg aaaatattgg aagaatttca tttcatttta caaaaataaa gagtgtagag     60
```

```
ggtattttg  taaatcaata  ttttttctat  aaaaaatata  taagaaatat  tattttaata   120
catcaaatca  aatactgtat  aagaaataat  gttaacataa  ttaatgcaag  tatagctaat   180
accaacatta  ctaatgcaag  tattactaat  acaccatatt  ctatattaat  cttatatact   240
ctaccaaacg  accctaagtg  tgtatctata  tcctccgaga  atttggaatt  tgcaaattcc   300
aagttttgta  tctcccttc   ccagaaatta  agataattct  ggtgctttta  gcattagaaa   360
agtatttatt  gggtagggaa  atgtcatgac  ttcacagcat  taagcatcaa  gggtataact   420
taatgaaata  gtggtcaatg  aattatattg  agaatgacga  ggtctctgtt  ccaactttgg   480
tagactttgg  aaatgctcgt  ctggacgccg  cccattcttt  ctagtcttgg  tgccattcta   540
tttggtctga  gactggcatg  atgccaaatt  ctaaccttt   cacaatgagc  attcgaccta   600 ctcttcttt   ttacgactct  atttgaccta  ctaggcattg  gccaacttgg  ctaaccactt   660
gaggaactag  agttcggatt  caatagaatc  taataatttt  aatcaaaaga  cttcatgtat   720
attgaaaaat  ctatttataa  ctaactttaa  atcggccttt  acgtatcgac  gtaatcaaaa   780
ttgtgtcagc  ttgccacgtg  gggtctagta  tgagtttgaa  attggtcata  ggggcccaa    840 ttccactaat  acagctgccg  tccatgcact  acaagacaaa  tacaccacta  tgtttgttag   900
tgcttggtaa  atgtaaaaca  aacttttgat  gagaatctat  tcgtggcatc  gaagtgctgc   960
aaattggctt  ttacctctgc  tacttcaagc  ctcactgatt  tcaccccaa   ctttctcatt  1020 tcccttttcaa ggatttgatt  ttccagttgg  gcatgttaaa  aacaacaatt  ttcctcaaaa  1080
ctgtagaaat  gatttctcat  attttaatca  gtcaaattat  ttaaacaaga  agttgatttt  1140
tttttaattt  ttttttttac  aaaaaaattt  caaatgtcaa  gtaagattt   tcaaattgaa  1200 actgaataag  ctgcgacttt  agaaacaaaa  aactaagata  agtaaaaata  ccaaaaagag  1260
tgaatcacat  caattgaatt  cttccaacag  ttcgtttttt  agtttctgtt  ttgggaagag  1320
gagtactaca  aggtaggacc  tccaacaatc  aacaatatct  aagttgcaaa  agttttgtg   1380 cgttttttag  tttctgtttc  gagaagagga  atactacaag  ttcgttttt   agtttctgtt  1440 ttgggaagag  gagtactgca  aggtaggacc  tccaacaatt  atcaatatct  aaattgcaaa  1500
aatttcagtt  cgttttttagt ttctgtttcg  ggaagaggaa  tactacaagt  tcgtttttta  1560 gtttctatt   tgggaagagg  agtactacaa  ggtaggacct  ccaatacccta aattgcaaaa  1620 atttcagttc  gttttttagt  ttcagtttag  ggaagaggaa  tactacaagg  taggacctcc  1680
aacaatcatc  agtacctaaa  ttgcaaaaat  ttcagttcgt  ttttagttt   atgtttggga  1740 agaagaatac  tacaaggcag  tggcggagct  accttatgat  tagggggttc  atccgaacct  1800
ccttcgacgg  aaaattatac  tatttttata  agtgaaaatt  attttttatg  tatatataat  1860
tgatgttgaa  cccccttcgg  ttagttcatg  tatctatatt  ttttattt    gaaccccgat  1920 gaaaattttg  gctccgccac  tgctacaagg  taggacctcc  aacaatcacc  aatacctaaa  1980
ttgcaaaaat  ttcagtttgt  ttttagtttt  ctgttttggg  aagaggaata  ctacaaggta  2040
ggacctccaa  caatcaccaa  tacctaaatt  gcaacgtttt  tttagtttct  gttttgggaa  2100
gaggaatact  acatggtagg  gcctccaaca  atcaccaata  cctaaattgc  aaaaatttca  2160
gttcgtattt  tcgtttctat  tttgggaagt  ggaatagtat  aagtaggac   ctccaacaat  2220 caccaatacc  taaattaaag  ttccgattca  tttttagtt   tctgttttgg  aaagagaaat  2280
actacaaggt  agggcctaca  acaatcacca  gtacctaaat  tgtaaaaatt  tcagttcgtt  2340
ttttagtttc  tattttgaga  agaggaatgc  tacaaggtag  ggcctacaac  aatcaccagt  2400
acctaaattg  taaaaatttc  agttcgtttt  ttagtttctg  ttttgggaag  aggaatacta  2460
```

```
caaggtaggg ccttcaacaa tcagcaatac ctaaattaca aaaatttcaa ttcgtttttt    2520
agtttctgtt ttgggaagag gaatactaca aggcagtggc ggagctacct tatgattagg    2580
ggttcatccg aacctccttc gacggaaaat tatactattt ttatatagta aaaattattt    2640
tttatgtata tataattgat gttgaacccc cttcggttag tttgtgtatc tatattttt     2700 tattttgaac ctccttgata aaaaattttg actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaatacct aaattgcaaa aatttcagtt    2880 tgtttttag tttctgtttt gggaagagga atactacaag gtaaggcctc caacaatcac     2940
caatacctaa attgcaaaaa tttcagttcg tattttcgtt tctatttttgg gaagtggaat   3000 agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttcttttttt    3240
agtttctgtt ttggaaagag aaatactaca agataggacc ttcaacaatc accaatacct    3300
aaattgcaaa aacttcagtt cattttttag tttctgtttt gggaagaaga atacttcaag    3360
gtaacaatca ccaatacctaa aattaaattt cagttagttt tttagtttct gttttttggga   3420 agaggaatac tttcttttgc tatataaagc caaagtaggt acctataagc atcaatattt    3480
tgtattgctt agtgattccc ctagttcggt atttcatttt ttttcactat actatatcac    3540
ctcctctcat aaatagccat tataaatctt gcattttctc taatgaaaac ccttctaaag    3600
ccttttccat ctcctttact ttccattcct actcctaaca tgtatagttt caaacacaac    3660 tccactttc caaatccaac caaacaaaaa gattcaagaa agttccatta tagaaacaaa     3720
agcagtacac atttttgtag ctttcttgat ttagcaccca catcaaagcc agagtcttta    3780
gatgttaaca tctcatgggt tgatactgat ctggacgggg ctgaattcga cgtgatcatc    3840
attggaactg gccctgccgg gcttcggcta gctgaacaag tttctaaata tggtattaag    3900
gtatgttgcg ttgacccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat ttggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gcggtagctt gattgttgat gcaagtggct atgctagtga ttttatagag    4260
tatgacaagc caagaaacca tggttatcaa gttgctcatg ggattttagc agaagttgat    4320
aatcatccat ttgatttgga taaaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttctttag tgagtcggcc tatgttatcg    4500
tatatggaag tgaaaagaag gatggtagca agattaagac atttgggat caaagtgaga     4560 agtgtccttg aggaagagaa gtgtgtgatc actatggaga gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag tttggaatgg tttgtggcct    4800
```

-continued

| | |
|---|---|
| tcggatagaa gacgtgttag agaatgttat tgtttcggaa tggagacttt gttgaagctt | 4860 |
| gatttggaag gtactaggag attgtttgat gctttctttg atgttgatcc caagtactgg | 4920 |
| cacgggttcc tttcttcaag attgtctgtc aaagaacttg ctgtactcag tttgtacctt | 4980 |
| tttggacatg cctctaattt ggctaggttg gatattgtta caagtgcac tgtcccttg | 5040 |
| gttaaactgc tgggcaatct agcaatagag agcctttgaa ttaatatgat agttttgaag | 5100 |
| cactgctttc atttaattt cttaggttat tttcatcttt tatcaatgca aaagtgaaac | 5160 |
| aaaagctata cacattgtca tcgttgttca aactcagaca agtttgccta gctctatgta | 5220 |
| tttatcctta acatatgtat tcatcaaatt cgaaatatac aatgtatggt tgtcgatgca | 5280 |
| ttggacaaaa gtatagagcc acaatctgat accaagtctg tatttggaag cactggctaa | 5340 |
| ttgttatggt taccaaacac tttgaattgg ctggataata acaggaaatt tatgttatta | 5400 |
| atcattaaca gcaaattggg aaagcaagaa ttattaggaa agttaatata gtgtcttggt | 5460 |
| tattctaatg gagtgggtta tgcaaattaa gttcccttat caagtttggg tttatgaact | 5520 |
| gctccactcg tgtccctctt aaaagcctta atcccaacat gtaccaccaa gaactgagc | 5580 |
| tgctccatca gatcctttga gaatgttaat atgttattta aatgaaggac tgaatgatta | 5640 |
| tgaggatgca atgcataggt ttaattacca gttatctgta aattgtcttc gttgccatta | 5700 |
| ttttaaaagt ttaataagtg taacatctac aaagagttga taa | 5743 |

<210> SEQ ID NO 45
<211> LENGTH: 5743
<212> TYPE: DNA
<213> ORGANISM: Capsicum annuum

<400> SEQUENCE: 45

| | |
|---|---|
| tgttgaatgg aaatattgg aagaatttca tttcatttta caaaaataaa gagtgtagag | 60 |
| ggtattttg taaatcaata tttttctat aaaaaatata taagaaatat tatttaata | 120 |
| catcaaatca aatactgtat aagaaataat gttaacataa ttaatgcaag tatagctaat | 180 |
| accaacatta ctaatgcaag tattactaat acaccatatt ctatattaat cttatatact | 240 |
| ctaccaaacg accctaagtg tgtatctata tcctccgaga atttggaatt tgcaaattcc | 300 |
| aagttttgta tctccctttc ccagaaatta agataattct ggtgctttta gcattagaaa | 360 |
| agtatttatt gggtagggaa atgtcatgac ttcacagcat taagcatcaa gggtataact | 420 |
| taatgaaata gtggtcaatg aattatattg agaatgacga ggtctctgtt ccaactttgg | 480 |
| tagactttgg aaatgctcgt ctggacgccg cccattcttt ctagtcttgg tgccattcta | 540 |
| tttggtctga gactggcatg atgccaaatt ctaaccttt cacaatgagc attcgaccta | 600 |
| ctcttctttt ttacgactct atttgaccta ctaggcattg gccaacttgg ctaaccactt | 660 |
| gaggaactag agttcggatt caatagaatc taataatttt aatcaaaaga cttcatgtat | 720 |
| attgaaaaat ctatttataa ctaactttaa atcggccttt acgtatcgac gtaatcaaaa | 780 |
| ttgtgtcagc ttgccacgtg gggtctagta tgagtttgaa attggtcata ggggcccaa | 840 |
| ttccactaat acagctgccg tccatgcact acaagacaaa tacaccacta tgtttgttag | 900 |
| tgcttggtaa atgtaaaaca aactttttgat gagaatctat tcgtggcatc gaagtgctgc | 960 |
| aaattggctt ttacctctgc tacttcaagc ctcactgatt ttcaccccaa ctttctcatt | 1020 |
| tcccttttcaa ggatttgatt ttccagttgg gcatgttaaa aacaacaatt ttcctcaaaa | 1080 |
| ctgtagaaat gatttctcat atttttaatca gtcaaattat ttaaacaaga agttgatttt | 1140 |
| tttttaattt ttttttttac aaaaaaattt caaatgtcaa gtaagatttt tcaaattgaa | 1200 |

```
actgaataag ctgcgacttt agaaacaaaa aactaagata agtaaaaata ccaaaaagag   1260
tgaatcacat caattgaatt cttccaacag ttcgttttt agtttctgtt ttgggaagag    1320
gagtactaca aggtaggacc tccaacaatc aacaatatct aagttgcaaa agttttgtg    1380 cgttttttag tttctgtttc gagaagagga atactacaag ttcgttttt agtttctgtt    1440 ttgggaagag gagtactgca aggtaggacc tccaacaatt atcaatatct aaattgcaaa    1500
aatttcagtt cgttttttagt ttctgtttcg ggaagaggaa tactacaagt tcgtttttta    1560 gtttctatttt tgggaagagg agtactacaa ggtaggacct ccaataccta aattgcaaaa    1620
atttcagttc gttttttagt ttcagtttag ggaagaggaa tactacaagg taggacctcc    1680
aacaatcatc agtacctaaa ttgcaaaaat ttcagttcgt ttttagtttt atgtttggga    1740
agaagaatac tacaaggcag tggcggagct accttatgat tagggggttc atccgaacct    1800
ccttcgacgg aaaattatac tattttata agtgaaaatt atttttatg tatatataat      1860 tgatgttgaa cccccttcgg ttagttcatg tatctatatt tttattt gaaccccgat       1920 gaaaattttg gctccgccac tgctacaagg taggacctcc aacaatcacc aatacctaaa    1980
ttgcaaaaat ttcagtttgt tttttagttt ctgttttggg aagaggaata ctacaaggta    2040
ggacctccaa caatcaccaa tacctaaatt gcaacgtttt tttagtttct gttttgggaa    2100
gaggaatact acatggtagg gcctccaaca atcaccaata cctaaattgc aaaaatttca    2160 gttcgtatttt tcgtttctat tttgggaagt ggaatagtat aaggtaggac ctccaacaat    2220
caccaatacc taaattaaag ttccgattca ttttttagtt tctgttttgg aaagagaaat    2280
actacaaggt agggcctaca acaatcacca gtacctaaat tgtaaaaatt tcagttcgtt    2340
ttttagtttc tattttgaga agaggaatgc tacaaggtag ggcctacaac aatcaccagt    2400
acctaaattg taaaaatttc agttcgtttt ttagtttctg ttttgggaag aggaatacta    2460
caaggtaggg ccttcaacaa tcagcaatac ctaaattaca aaaatttcaa ttcgtttttt    2520
agtttctgtt ttgggaagag gaatactaca aggcagtggc ggagctacct tatgattagg    2580
ggttcatccg aacctccttc gacggaaaat tatactattt tatatagta aaaattattt     2640 tttatgtata taattgat gttgaacccc cttcggttag tttgtgtatc tatattttt      2700 tattttgaac ctccttgata aaaattttg actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaataccct aaattgcaaa aatttcagtt    2880
tgttttttag tttctgtttt gggaagagga atactacaag gtaaggcctc caacaatcac    2940
caatacctaa attgcaaaaa tttcagttcg tattttcgtt tctattttgg gaagtggaat    3000
agtataaggt aggacctcca acaatcacca tacctaaat tgcaaaagtt ccgattcatt     3060
ttttagtttc tgttttggaa agagaaatac tacaaggtag ggtctccaac aatcaccagt    3120
acctaaattg taaaaatttc agttcgtttt tagtttcta ttttgggaag tggaatagta     3180
taaggtagga cctccaacaa tcaccaatac ctaaattgca aaagttccga ttcttttttt    3240
agtttctgtt ttgggaagag aaatactaca agataggacc ttcaacaatc accaatacct    3300
aaattgcaaa aacttcagtt cattttttag tttctgtttt gggaagaaga atacttcaag    3360
gtaacaatca ccaataccta aattaaattt cagttagttt tttagtttct gttttgggaa    3420
agaggaatac tttctttgc tatataaagc caaagtaggg acctaaagc atcaatattt      3480 tgtattgctt agtgattccc ctagttcggt atttcatttt ttttcactat actatatcac    3540
```

-continued
ctcctctcat aaatagccat tataaatctt gcattttctc taatggaaac ccttctaaag 3600
ccttttccat ctcctttact ttccattcct actcctaaca tgtatagttt caaacacaac 3660
tccacttttc caaatccaac caaacaaaaa gattcaagaa agttccatta tagaaacaaa 3720
agcagtacac atttttgtag ctttcttgat ttagcaccca catcaaagcc agagtcttta 3780
gatgttaaca tctcatgggt tgatactgat ctggacgggg ctgaattcga cgtgatcatc 3840
attggaactg gccctgccgg gcttcggcta gctgaacaag tttctaaata tggtattaag 3900
gtatgttgcg ttgacccttc accactttcc atgtggccaa ataattatgg tgtttgggtt 3960
gatgagtttg aaaagttggg attagaagat tgtctagatc ataagtggcc tgtgagttgt 4020
gttcatataa gtgatcacaa gactaagtat ttggacagac catatggtag agtaagtaga 4080
aagaagttga agttgaaatt gttgaatagt tgtgttgaaa atagagtgaa gttttataaa 4140
gccaaggttt tgaaagtgaa gcatgaagaa tttgagtctt cgattgtttg tgatgatggt 4200
aggaagataa gcggtagctt gattgttgat gcaagtggct atgctagtga ttttatagag 4260
tatgacaagc caagaaacca tggttatcaa gttgctcatg ggattttagc agaagttgat 4320
aatcatccat ttgatttgga taaaatgatg cttatggatt ggagggattc tcatttaggt 4380
aatgagccat atctgagggt gaagaatact aaagaaccaa cattcttgta tgcaatgcca 4440
tttgatagga atttggtatt cttggaagag acttctttag tgagtcggcc tatgttatcg 4500
tatatggaag tgaaaagaag gatggtagca agattaagac atttggggat caaagtgaga 4560
agtgtccttg aggaagagaa gtgtgtgatc actatgggag gaccacttcc gcggattcct 4620
caaaatgtta tggctattgg tgggacttca gggatagttc atccatcgtc tgggtacatg 4680
gtggctcgta gcatggcatt ggcaccagta ctggctgagg ccatcgtcga aagccttggc 4740
tcaacaagaa tgataagagg gtctcaactt taccatagag tttggaatgg tttgtggcct 4800
tcggatagaa gacgtgttag agaatgttat tgtttcggaa tggagacttt gttgaagctt 4860
gatttggaag gtactaggag attgtttgat gctttctttg atgttgatcc caagtactgg 4920
cacgggttcc tttcttcaag attgtctgtc aaagaacttg ctgtactcag tttgtacctt 4980
tttggacatg cctctaattt ggctaggttg gatattgtta caaagtgcac tgtccccttg 5040
gttaaactgc tgggcaatct agcaatagag agcctttgaa ttaatatgat agttttgaag 5100
cactgctttc attttaattt cttaggttat tttcatcttt tatcaatgca aaagtgaaac 5160
aaaagctata cacattgtca tcgttgttca aactcagaca agtttgccta gctctatgta 5220
tttatcctta acatatgtat tcatcaaatt cgaaatatac aatgtatggt tgtcgatgca 5280
ttggacaaaa gtatagagcc acaatctgat accaagtctg tatttggaag cactggctaa 5340
ttgttatggt taccaaacac tttgaattgg ctggataata acaggaaatt tatgttatta 5400
atcattaaca gcaaattggg aaagcaagaa ttattaggaa agttaatata gtgtcttggt 5460
tattctaatg gagtgggtta tgcaaattaa gttcccttat caaagtttgg tttatgaact 5520
gctccactcg tgtccctctt aaaagcctta atcccaacat gtaccaccaa agaactgagc 5580
tgctccatca gatcctttga gaatgttaat atgttattta aatgaaggac tgaatgatta 5640
tgaggatgca atgcataggt ttaattacca gttatctgta aattgtcttc gttgccatta 5700
ttttaaaagt ttaataagtg taacatctac aaagagttga taa 5743

<210> SEQ ID NO 46
<211> LENGTH: 5743
<212> TYPE: DNA
<213> ORGANISM: Capsicum annuum

```
<400> SEQUENCE: 46
tgttgaatgg aaaatattgg aagaatttca tttcatttta caaaaataaa gagtgtagag      60
ggtatttttg taaatcaata ttttttctat aaaaaatata taagaaatat tattttaata     120
catcaaatca aatactgtat aagaaataat gttaacataa ttaatgcaag tatagctaat     180
accaacatta ctaatgcaag tattactaat acaccatatt ctatattaat cttatatact     240
ctaccaaacg accctaagtg tgtatctata tcctccgaga atttggaatt tgcaaattcc     300
aagttttgta tctcccttc ccagaaatta agataattct ggtgctttta gcattagaaa     360
agtatttatt gggtagggaa atgtcatgac ttcacagcat taagcatcaa gggtataact     420
taatgaaata gtggtcaatg aattatattg agaatgacga ggtctctgtt ccaactttgg     480
tagactttgg aaatgctcgt ctggacgccg cccattcttt ctagtcttgg tgccattcta     540
tttggtctga gactggcatg atgccaaatt ctaaccttt cacaatgagc attcgaccta     600
ctcttctttt ttacgactct atttgaccta ctaggcattg gccaacttgg ctaaccactt     660
gaggaactag agttcggatt caatagaatc taataatttt aatcaaaaga cttcatgtat     720
attgaaaaat ctatttataa ctaactttaa atcggccttt acgtatcgac gtaatcaaaa     780
ttgtgtcagc ttgccacgtg gggtctagta tgagtttgaa attggtcata ggggcccaa     840 ttccactaat acagctgccg tccatgcact acaagacaaa tacaccacta tgttgttag      900 tgcttggtaa atgtaaaaca aacttttgat gagaatctat tcgtggcatc gaagtgctgc     960
aaattggctt ttacctctgc tacttcaagc ctcactgatt ttcacccca cttcctcatt    1020 tccctttcaa ggatttgatt ttccagttgg gcatgttaaa acaacaatt ttcctcaaaa     1080 ctgtagaaat gatttctcat attttaatca gtcaaattat ttaaacaaga agttgatttt    1140
tttttaattt tttttttac aaaaaaattt caaatgtcaa gtaagatttt tcaaattgaa     1200
actgaataag ctgcgacttt agaaacaaaa aactaagata agtaaaaata ccaaaagag     1260 tgaatcacat caattgaatt cttccaacag ttcgtttttt agtttctgtt ttgggaagag    1320
gagtactaca aggtaggacc tccaacaatc aacaatatct aagttgcaaa agttttgtg    1380 cgttttttag tttctgttc gagaagagga atactacaag ttcgtttttt agtttctgtt    1440
ttgggaagag gagtactgca aggtaggacc tccaacaatt atcaatatct aaattgcaaa    1500
aatttcagtt cgttttagt ttctgttcg ggaagaggaa tactacaagt tcgttttta     1560 gtttctattt tgggaagagg agtactacaa ggtaggacct ccaataccta aattgcaaaa    1620
atttcagttc gttttttagt ttcagtttag ggaagaggaa tactacaagg taggacctcc    1680
aacaatcatc agtacctaaa ttgcaaaaat ttcagttcgt ttttagtttt atgtttggga    1740
agaagaatac tacaaggcag tggcggagct accttatgat taggggttc atccgaacct    1800 ccttcgacgg aaaattatac tattttata agtgaaaatt attttttatg tatatataat    1860
tgatgttgaa cccccttcgg ttagttcatg tatctatatt ttttattttt gaaccccgat    1920
gaaaattttg gctccgccac tgctacaagg taggacctcc aacaatcacc aatacctaaa    1980
ttgcaaaaat ttcagtttgt tttttagttt ctgttttggg aagaggaata ctacaaggta    2040
ggacctccaa caatcaccaa tacctaaatt gcaacgtttt tttagtttct gttttgggaa    2100
gaggaatact acatggtagg gcctccaaca atcaccaata cctaaattgc aaaaatttca    2160
gttcgtattt tcgtttctat tttgggaagt ggaaatagtat aaggtaggac ctccaacaat    2220
caccaatacc taaattaaag ttccgattca tttttagtt tctgttttgg aaagagaaat    2280
```

```
actacaaggt agggcctaca acaatcacca gtacctaaat tgtaaaaatt tcagttcgtt    2340
ttttagtttc tattttgaga agaggaatgc tacaaggtag ggcctacaac aatcaccagt    2400
acctaaattg taaaaatttc agttcgtttt ttagtttctg ttttgggaag aggaatacta    2460
caaggtaggg ccttcaacaa tcagcaatac ctaaattaca aaaatttcaa ttcgtttttt    2520
agtttctgtt ttgggaagag gaatactaca aggcagtggc ggagctacct tatgattagg    2580
ggttcatccg aacctccttc gacggaaaat tatactattt ttatatagta aaaattattt    2640
tttatgtata tataattgat gttgaacccc cttcggttag tttgtgtatc tatattttt    2700 tattttgaac ctccttgata aaaattttg actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaatacct aaattgcaaa aatttcagtt    2880
tgttttttag tttctgtttt gggaagagga atactacaag gtaaggcctc caacaatcac    2940
caatacctaa attgcaaaaa tttcagttcg tattttcgtt tctatttgg gaagtggaat    3000 agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttcttttttt    3240
agtttctgtt ttggaaagag aaatactaca agataggacc ttcaacaatc accaatacct    3300
aaattgcaaa aacttcagtt cattttttag tttctgtttt gggaagaaga atacttcaag    3360
gtaacaatca ccaatacctc aattaaattt cagttagttt tttagtttct gttttggga    3420 agaggaatac tttcttttgc tatataaagc caaagtaggt acctataagc atcaatattt    3480
tgtattgctt agtgattccc ctagttcggt atttcatttt tttcactat actatatcac    3540 ctcctctcat aaatagccat tataaatctt gcattttctc taatggaaac ccttctaaag    3600
ccttttccat ctccttttact ttccattcct actcctaaca tgtatagttt caaacacaac    3660
tccacttttc caaatccaac caaacaaaaa gattcaagaa agttccatta tagaaacaaa    3720
agcagtacac attttttgtag ctttcttgat ttagcaccca catcaaagcc agagtcttta    3780
gatgttaaca tctcatgggt tgatactgat ctggacgggg ctgaattcga cgtgatcatc    3840
attggaactg gccctgccgg gcttcggcta gctgaacaag tttctaaata tggtattaag    3900
gtatgttgcg ttgaccccttc accactttcc atgtggccaa taattatgg tgtttgggtt    3960 gatgagtttg aaaagttggg attagaagat tgtctagatc ataagtggcc tgtgagttgt    4020
gttcatataa gtgatcacaa gactaagtat ttggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gcggtagctt gattgttgat gcaagtggct atgctagtga ttttatagag    4260
tatgacaagc caagaaacca tggttatcaa gttgctcatg ggattttagc agaagttgat    4320
aatcatccat ttgatttgga taaaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttctttag tgagtcggcc tatgttatcg    4500 tatatgaag tgaaaagaag gatggtagca agattaagac atttggggat caaagtgaga    4560
agtgtccttg aggaagagaa gtgtgtgatc actatgggag gaccacttcc gcggattcct    4620
caaaatgtta tggctattgg tgggacttca gggatagttc atccatcgtc tgggtacatg    4680
```

-continued

| | |
|---|---|
| gtggctcgta gcatggcatt ggcaccagta ctggctgagg ccatcgtcga aagccttggc | 4740 |
| tcaacaagaa tgataagagg gtctcaactt taccatagag tttggaatgg tttgtggcct | 4800 |
| tcggatagaa gacgtgttag agaatgttat tgtttcggaa tggagacttt gttgaagctt | 4860 |
| gatttggaag gtactaggag attgtttgat gctttctttg atgttgatcc caagtactgg | 4920 |
| cacgggttcc tttcttcaag attgtctgtc aaagaacttg ctgtactcag tttgtacctt | 4980 |
| tttggacatg cctctaattt ggctaggttg atattgtta caagtgcac tgtccccttg | 5040 |
| gttaaactgc tgggcaatct agcaatagag agcctttgaa ttaatatgat agttttgaag | 5100 |
| cactgctttc attttaattt cttaggttat tttcatcttt tatcaatgca aaagtgaaac | 5160 |
| aaaagctata cacattgtca tcgttgttca aactcagaca agtttgccta gctctatgta | 5220 |
| tttatcctta acatatgtat tcatcaaatt cgaaatatac aatgtatggt tgtcgatgca | 5280 |
| ttggacaaaa gtatagagcc acaatctgat accaagtctg tatttggaag cactggctaa | 5340 |
| ttgttatggt taccaaacac tttgaattgg ctggataata acaggaaatt tatgttatta | 5400 |
| atcattaaca gcaaattggg aaagcaagaa ttattaggaa agttaatata gtgtcttggt | 5460 |
| tattctaatg gagtgggtta tgcaaattaa gttcccttat caaagtttgg tttatgaact | 5520 |
| gctccactcg tgtccctctt aaaagcctta atcccaacat gtaccaccaa agaactgagc | 5580 |
| tgctccatca gatcctttga gaatgttaat atgttattta aatgaaggac tgaatgatta | 5640 |
| tgaggatgca atgcataggt ttaattacca gttatctgta aattgtcttc gttgccatta | 5700 |
| ttttaaaagt ttaataagtg taacatctac aaagagttga taa | 5743 |

<210> SEQ ID NO 47
<211> LENGTH: 1316
<212> TYPE: DNA
<213> ORGANISM: Capsicum annuum

<400> SEQUENCE: 47

| | |
|---|---|
| tgttgaatgg aaaatattgg aagaatttca tttcatttta caaaaataaa gagtgtagag | 60 |
| ggtattttg taaatcaata ttttttctat aaaaaatata taagaaatat tattttaata | 120 |
| catcaaatca aatactgtat aagaaataat gttaacataa ttaatgcaag tatagctaat | 180 |
| accaacatta ctaatgcaag tattactaat acaccatatt ctatattaat cttatatact | 240 |
| ctaccaaacg accctaagtg tgtatctata tcctccgaga atttggaatt tgcaaattcc | 300 |
| aagttttgta tctcccttc ccagaaatta agataattct ggtgcttta gagtttggaa | 360 |
| tggtttgtgg ccttcggata gaagacgtgt tagagaatgt tattgtttcg gaatggagac | 420 |
| tttgttgaag cttgatttgg aaggtactag gagattgttt gatgctttct tgatgttga | 480 |
| tcccaagtac tggcacgggt tcctttcttc aagattgtct gtcaaagaac ttgctgtact | 540 |
| cagtttgtac cttttggac atgcctctaa tttggctagg ttggatattg ttacaaagtg | 600 |
| cactgtcccc ttggttaaac tgctgggcaa tctagcaata gagagccttt gaattaatat | 660 |
| gatagttttg aagcactgct ttcattttaa tttcttaggt tattttcatc ttttatcaat | 720 |
| gcaaaagtga acaaaagct atacacattg tcatcgttgt tcaaactcag acaagtttgc | 780 |
| ctagctctat gtatttatcc ttaacatatg tattcatcaa attcgaaata tacaatgtat | 840 |
| ggttgtcgat gcattggaca aaagtataga gccacaatct gataccaagt ctgtatttgg | 900 |
| aagcactggc taattgttat ggttaccaaa cactttgaat tggctggata taacaggaa | 960 |
| atttatgtta ttaatcatta acagcaaatt gggaaagcaa gaattattag gaaagttaat | 1020 |

```
atagtgtctt ggttattcta atggagtggg ttatgcaaat taagttccct tatcaaagtt    1080
tggtttatga actgctccac tcgtgtccct cttaaaagcc ttaatcccaa catgtaccac    1140
caaagaactg agctgctcca tcagatcctt tgagaatgtt aatatgttat ttaaatgaag    1200
gactgaatga ttatgaggat gcaatgcata ggtttaatta ccagttatct gtaaattgtc    1260
ttcgttgcca ttattttaaa agtttaataa gtgtaacatc tacaaagagt tgataa       1316
```

<210> SEQ ID NO 48
<211> LENGTH: 1316
<212> TYPE: DNA
<213> ORGANISM: Capsicum annuum

<400> SEQUENCE: 48

```
tgttgaatgg aaaatattgg aagaatttca tttcatttta caaaaataaa gagtgtagag     60 ggtattttg taaatcaata ttttttctat aaaaaatata taagaaatat tattttaata    120
catcaaatca aatactgtat aagaaataat gttaacataa ttaatgcaag tatagctaat    180
accaacatta ctaatgcaag tattactaat acaccatatt ctatattaat cttatatact    240
ctaccaaacg accctaagtg tgtatctata tcctccgaga atttggaatt tgcaaattcc    300
aagttttgta tctcccttc ccagaaatta agataattct ggtgctttta gagtttggaa     360
tggtttgtgg ccttcggata aagacgtgt tagagaatgt tattgtttcg aatggagac     420 tttgttgaag cttgatttgg aaggtactag gagattgttt gatgctttct ttgatgttga    480
tcccaagtac tggcacgggt tccttttcttc aagattgtct gtcaaagaac ttgctgtact    540 cagttttgtac cttttttggac atgcctctaa tttggctagg ttggatattg ttacaaagtg    600
cactgtcccc ttggttaaac tgctgggcaa tctagcaata gagagccttt gaattaatat    660
gatagttttg aagcactgct ttcattttaa tttcttaggt tattttcatc ttttatcaat    720
gcaaaagtga acaaaaagct atacacattg tcatcgttgt tcaaactcag acaagtttgc    780
ctagctctat gtatttatcc ttaacatatg tattcatcaa attcgaaata tacaatgtat    840
ggttgtcgat gcattggaca aaagtataga gccacaatct gataccaagt ctgtatttgg    900
aagcactggc taattgttat ggttaccaaa cactttgaat tggctggata taacaggaa     960 atttatgtta ttaatcatta acagcaaatt gggaaagcaa gaattattag gaaagttaat    1020
atagtgtctt ggttattcta atggagtggg ttatgcaaat taagttccct tatcaaagtt    1080
tggtttatga actgctccac tcgtgtccct cttaaaagcc ttaatcccaa catgtaccac    1140
caaagaactg agctgctcca tcagatcctt tgagaatgtt aatatgttat ttaaatgaag    1200
gactgaatga ttatgaggat gcaatgcata ggtttaatta ccagttatct gtaaattgtc    1260
ttcgttgcca ttattttaaa agtttaataa gtgtaacatc tacaaagagt tgataa       1316
```

<210> SEQ ID NO 49
<211> LENGTH: 1316
<212> TYPE: DNA
<213> ORGANISM: Capsicum annuum

<400> SEQUENCE: 49

```
tgttgaatgg aaaatattgg aagaatttca tttcatttta caaaaataaa gagtgtagag     60 ggtattttg taaatcaata ttttttctat aaaaaatata taagaaatat tattttaata    120
catcaaatca aatactgtat aagaaataat gttaacataa ttaatgcaag tatagctaat    180
accaacatta ctaatgcaag tattactaat acaccatatt ctatattaat cttatatact    240
ctaccaaacg accctaagtg tgtatctata tcctccgaga atttggaatt tgcaaattcc    300
```

```
aagttttgta tctcccttc ccagaaatta agataattct ggtgctttta gagtttggaa      360
tggtttgtgg ccttcggata gaagacgtgt tagagaatgt tattgtttcg gaatggagac      420
tttgttgaag cttgatttgg aaggtactag gagattgttt gatgctttct ttgatgttga      480
tcccaagtac tggcacgggt tcctttcttc aagattgtct gtcaaagaac ttgctgtact      540
cagtttgtac cttttggac atgcctctaa tttggctagg ttggatattg ttacaaagtg       600
cactgtcccc ttggttaaac tgctgggcaa tctagcaata gagagccttt gaattaatat      660
gatagttttg aagcactgct ttcattttaa tttcttaggt tattttcatc ttttatcaat      720
gcaaaagtga acaaaagct atacacattg tcatcgttgt tcaaactcag acaagtttgc       780
ctagctctat gtatttatcc ttaacatatg tattcatcaa attcgaaata tacaatgtat      840
ggttgtcgat gcattggaca aaagtataga gccacaatct gataccaagt ctgtatttgg      900
aagcactggc taattgttat ggttaccaaa cactttgaat tggctggata ataacaggaa      960
atttatgtta ttaatcatta acagcaaatt gggaaagcaa gaattattag gaaagttaat     1020
atagtgtctt ggttattcta atggagtggg ttatgcaaat taagttccct tatcaaagtt     1080
tggtttatga actgctccac tcgtgtccct cttaaaagcc ttaatcccaa catgtaccac     1140
caaagaactg agctgctcca tcagatcctt tgagaatgtt aatatgttat ttaaatgaag     1200
gactgaatga ttatgaggat gcaatgcata ggtttaatta ccagttatct gtaaattgtc     1260
ttcgttgcca ttattttaaa agtttaataa gtgtaacatc tacaaagagt tgataa        1316

<210> SEQ ID NO 50
<211> LENGTH: 1316
<212> TYPE: DNA
<213> ORGANISM: Capsicum annuum

<400> SEQUENCE: 50
tgttgaatgg aaaatattgg aagaatttca tttcatttta caaaaataaa gagtgtagag       60 ggtattttg taaatcaata tttttctat aaaaaatata taagaaatat tatttttaata      120 catcaaatca aatactgtat aagaaataat gttaacataa ttaatgcaag tatagctaat      180
accaacatta ctaatgcaag tattactaat acaccatatt ctatattaat cttatatact      240
ctaccaaacg accctaagtg tgtatctata tcctccgaga atttggaatt tgcaaattcc      300
aagttttgta tctcccttc ccagaaatta agataattct ggtgctttta gagtttggaa       360
tggtttgtgg ccttcggata gaagacgtgt tagagaatgt tattgtttcg gaatggagac      420
tttgttgaag cttgatttgg aaggtactag gagattgttt gatgctttct ttgatgttga      480
tcccaagtac tggcacgggt tcctttcttc aagattgtct gtcaaagaac ttgctgtact      540
cagtttgtac cttttggac atgcctctaa tttggctagg ttggatattg ttacaaagtg       600
cactgtcccc ttggttaaac tgctgggcaa tctagcaata gagagccttt gaattaatat      660
gatagttttg aagcactgct ttcattttaa tttcttaggt tattttcatc ttttatcaat      720
gcaaaagtga acaaaagct atacacattg tcatcgttgt tcaaactcag acaagtttgc       780
ctagctctat gtatttatcc ttaacatatg tattcatcaa attcgaaata tacaatgtat      840
ggttgtcgat gcattggaca aaagtataga gccacaatct gataccaagt ctgtatttgg      900
aagcactggc taattgttat ggttaccaaa cactttgaat tggctggata ataacaggaa      960
ctttatgtta ttaatcatta acagcaaatt gggaaagcaa gaattattag gaaagttaat     1020
atagtgtctt ggttattcta atggagtggg ttatgcaaat taagttccct tatcaaagtt     1080
```

| tggtttatga actgctccac tcgtgtccct cttaaaagcc ttaatcccaa catgtaccac | 1140 |
| caaagaactg agctgctcca tcagatcctt tgagaatgtt aatatgttat ttaaatgaag | 1200 |
| gactgaatga ttatgaggat gcaatgcata ggtttaatta ccagttatct gtaaattgtc | 1260 |
| ttcgttgcca ttattttaaa agtttaataa gtgtaacatc tacaaagagt tgataa | 1316 |

<210> SEQ ID NO 51
<211> LENGTH: 1316
<212> TYPE: DNA
<213> ORGANISM: Capsicum annuum

<400> SEQUENCE: 51

| tgttgaatgg aaatattgg aagaatttca tttcatttta caaaaataaa gagtgtagag | 60 |
| ggtattttg taaatcaata ttttttctat aaaaaatata taagaaatat tattttaata | 120 |
| catcaaatca aatactgtat aagaaataat gttaacataa ttaatgcaag tatagctaat | 180 |
| accaacatta ctaatgcaag tattactaat acaccatatt ctatattaat cttatatact | 240 |
| ctaccaaacg accctaagtg tgtatctata tcctccgaga atttggaatt tgcaaattcc | 300 |
| aagttttgta tctcccttc ccagaaatta agataattct ggtgctttta gagtttggaa | 360 |
| tggtttgtgg ccttcggata gaagacgtgt tagagaatgt tattgtttcg gaatgggagac | 420 |
| tttgttgaag cttgatttgg aaggtactag gagattgttt gatgctttct ttgatgttga | 480 |
| tcccaagtac tggcacgggt tccttttcttc aagattgtct gtcaaagaac ttgctgtact | 540 |
| cagtttgtac cttttggac atgcctctaa tttggctagg ttggatattg ttacaaagtg | 600 |
| cactgtcccc ttggttaaac tgctgggcaa tctagcaata gagagccttt gaattaatat | 660 |
| gatagttttg aagcactgct ttcattttaa tttcttaggt tattttcatc ttttatcaat | 720 |
| gcaaaagtga aacaaaagct atacacattg tcatcgttgt tcaaactcag acaagtttgc | 780 |
| ctagctctat gtatttatcc ttaacatatg tattcatcaa attcgaaata tacaatgtat | 840 |
| ggttgtcgat gcattggaca aaagtataga gccacaatct gataccaagt ctgtatttgg | 900 |
| aagcactggc taattgttat ggttaccaaa cactttgaat tggctggata ataacaggaa | 960 |
| atttatgtta ttaatcatta acagcaaatt gggaaagcaa gaattattag gaaagttaat | 1020 |
| atagtgtctt ggttattcta atggagtggg ttatgcaaat taagttccct tatcaaagtt | 1080 |
| tggtttatga actgctccac tcgtgtccct cttaaaagcc ttaatcccaa catgtaccac | 1140 |
| caaagaactg agctgctcca tcagatcctt tgagaatgtt aatatgttat ttaaatgaag | 1200 |
| gactgaatga ttatgaggat gcaatgcata ggtttaatta ccagttatct gtaaattgtc | 1260 |
| ttcgttgcca ttattttaaa agtttaataa gtgtaacatc tacaaagagt tgataa | 1316 |

<210> SEQ ID NO 52
<211> LENGTH: 1316
<212> TYPE: DNA
<213> ORGANISM: Capsicum annuum

<400> SEQUENCE: 52

| tgttgaatgg aaatattgg aagaatttca tttcatttta caaaaataaa gagtgtagag | 60 |
| ggtattttg taaatcaata ttttttctat aaaaaatata taagaaatat tattttaata | 120 |
| catcaaatca aatactgtat aagaaataat gttaacataa ttaatgcaag tatagctaat | 180 |
| accaacatta ctaatgcaag tattactaat acaccatatt ctatattaat cttatatact | 240 |
| ctaccaaacg accctaagtg tgtatctata tcctccgaga atttggaatt tgcaaattcc | 300 |
| aagttttgta tctcccttc ccagaaatta agataattct ggtgctttta gagtttggaa | 360 |

```
tggtttgtgg ccttcggata aagacgtgt tagagaatgt tattgtttcg gaatggagac    420
tttgttgaag cttgatttgg aaggtactag gagattgttt gatgctttct ttgatgttga    480
tcccaagtac tggcacgggt tcctttcttc aagattgtct gtcaaagaac ttgctgtact    540
cagtttgtac cttttggac atgcctctaa tttggctagg ttggatattg ttacaaagtg    600
cactgtcccc ttggttaaac tgctgggcaa tctagcaata gagagccttt gaattaatat    660
gatagttttg aagcactgct ttcattttaa tttcttaggt tattttcatc ttttatcaat    720
gcaaaagtga aacaaaagct atacacattg tcatcgttgt tcaaactcag acaagtttgc    780
ctagctctat gtatttatcc ttaacatatg tattcatcaa attcgaaata tacaatgtat    840
ggttgtcgat gcattggaca aaagtataga gccacaatct gataccaagt ctgtatttgg    900
aagcactggc taattgttat ggttaccaaa cactttgaat tggctggata taacaggaa    960 atttatgtta ttaatcatta acagcaaatt gggaaagcaa gaattattag gaaagttaat   1020
atagtgtctt ggttattcta atggagtggg ttatgcaaat taagttccct tatcaaagtt   1080
tggtttatga actgctccac tcgtgtccct cttaaaagcc ttaatcccaa catgtaccac   1140
caaagaactg agctgctcca tcagatcctt tgagaatgtt aatatgttat ttaaatgaag   1200
gactgaatga ttatgaggat gcaatgcata ggtttaatta ccagttatct gtaaattgtc   1260
ttcgttgcca ttattttaaa agtttaataa gtgtaacatc tacaaagagt tgataa       1316

<210> SEQ ID NO 53
<211> LENGTH: 1316
<212> TYPE: DNA
<213> ORGANISM: Capsicum annuum

<400> SEQUENCE: 53
tgttgaatgg aaaatattgg aagaatttca tttcatttta caaaaataaa gagtgtagag     60 ggtattttg taaatcaata ttttttctat aaaaaatata taagaaatat tattttaata    120
catcaaatca aatactgtat aagaaataat gttaacataa ttaatgcaag tatagctaat    180
accaacatta ctaatgcaag tattactaat acaccatatt ctatattaat cttatatact    240
ctaccaaacg accctaagtg tgtatctata tcctccgaga atttggaatt tgcaaattcc    300
aagttttgta tctcccttc ccagaaatta agataattct ggtgcttta gagtttggaa    360 tggtttgtgg ccttcggata gaagacgtgt tagagaatgt tattgtttcg gaatggagac    420
tttgttgaag cttgatttgg aaggtactag gagattgttt gatgctttct ttgatgttga    480
tcccaagtac tggcacgggt tcctttcttc aagattgtct gtcaaagaac ttgctgtact    540
cagtttgtac cttttggac atgcctctaa tttggctagg ttggatattg ttacaaagtg    600
cactgtcccc ttggttaaac tgctgggcaa tctagcaata gagagccttt gaattaatat    660
gatagttttg aagcactgct ttcattttaa tttcttaggt tattttcatc ttttatcaat    720
gcaaaagtga aacaaaagct atacacattg tcatcgttgt tcaaactcag acaagtttgc    780
ctagctctat gtatttatcc ttaacatatg tattcatcaa attcgaaata tacaatgtat    840
ggttgtcgat gcattggaca aaagtataga gccacaatct gataccaagt ctgtatttgg    900
aagcactggc taattgttat ggttaccaaa cactttgaat tggctggata taacaggaa    960 atttatgtta ttaatcatta acagcaaatt gggaaagcaa gaattattag gaaagttaat   1020
atagtgtctt ggttattcta atggagtggg ttatgcaaat taagttccct tatcaaagtt   1080
tggtttatga actgctccac tcgtgtccct cttaaaagcc ttaatcccaa catgtaccac   1140
```

-continued

| | |
|---|---|
| caaagaactg agctgctcca tcagatcctt tgagaatgtt aatatgttat ttaaatgaag | 1200 |
| gactgaatga ttatgaggat gcaatgcata ggtttaatta ccagttatct gtaaattgtc | 1260 |
| ttcgttgcca ttatttttaaa agtttaataa gtgtaacatc tacaaagagt tgataa | 1316 |

<210> SEQ ID NO 54
<211> LENGTH: 5760
<212> TYPE: DNA
<213> ORGANISM: Capsicum annuum

<400> SEQUENCE: 54

| | |
|---|---|
| tgttgaatgg aaaatattgg aagaatttca tttcatttta caaaaataaa gagtgtagag | 60 |
| ggtattttg taaatcaata ttttttctat aaaaaatata taagaaatat tatttttaata | 120 |
| catcaaatca aatactgtat aagaaataat gttaacataa ttaatgcaag tatagctaat | 180 |
| accaacatta ctaatgcaag tattactaat acaccatatt ctatattaat cttatatact | 240 |
| ctaccaaacg accctaagtg tgtatctata tcctccgaga atttggaatt tgcaaattcc | 300 |
| aagttttgta tctcccttc ccagaaatta agataattct ggtgctttta gcattagaaa | 360 |
| agtatttatt gggtagggaa atgtcatgac ttcacagcat taagcatcaa gggtataact | 420 |
| taatgaaata gtggtcaatg aattatattg agaatgacga ggtctctgtt ccaactttgg | 480 |
| tagactttgg aaatgctcgt ctggacgccg cccattcttt ctagtcttgg tgccattcta | 540 |
| tttggtctga aatggcatg atgccaaatt ctacctttc acaatgagca ttcgacctac | 600 |
| tcttcttttt tcgactcatt tgacctacta ggcattggcc aacttggcta accacttgag | 660 |
| gaactagagt tcggattcaa tagaatctaa taatttaat caaagacttt catgtatatt | 720 |
| gaaaaatcta tttataacta actttaaatc ggcctttacg tatcgacgta atcaaaattg | 780 |
| tgtcagcttg ccacgtgggg tctagtatga gtttgaaatt ggtcataggg gccccaattc | 840 |
| cactaataca gctgccgtcc atgcactaca agacaaatac accactatgt tgttagtgc | 900 |
| ttggtaaatg taaaacaaac ttttgatgag aatctattcg tggcatcgaa gtgctgcaaa | 960 |
| ttggctttta cctctgctac ttcaagcctc actgatttc accccaactt tctcatttcc | 1020 |
| cttttcaagga tttgatttc cagttgggca tgttaaaaac aacaatttc ctcaaaactg | 1080 |
| tagaaatgat ttctcatatt ttaatcagtc aaattattta acaagaagt tgattttttt | 1140 |
| ttaatttttt ttttttacaaa aaaatttcaa atgtcaagta agattttca aattgaaact | 1200 |
| gaataagctg cgactttaga aacaaaaaac taagataagt aaaaatacca aaaagagtga | 1260 |
| atcacatcaa ttgaattctt ccaacagttc gttttttagt ttctgttttg ggaagaggag | 1320 |
| tactacaagg taggacctcc aacaatcaac aatatctaag ttgcaaaagt ttttgtgcgt | 1380 |
| tttttagttt ctgtttcgag aagaggaata ctacaagttc gttttttagt ttctgttttg | 1440 |
| ggaagaggag tactgcaagg taggacctcc aacaattatc aatatctaaa ttgcaaaaat | 1500 |
| ttcagttcgt ttttagtttc tgtttcggga agaggaatac tacaagttcg ttttttagtt | 1560 |
| tctattttgg gaagaggagt actacaaggt aggacctcca atacctaaat tgcaaaaatt | 1620 |
| tcagttcgtt tttagtttc agtttaggga agaggaatac tacaaggtag gacctccaac | 1680 |
| aatcatcagt acctaaattg caaaaatttc agttcgtttt ttagtttatg ttttgggaag | 1740 |
| aagaatacta caaggcagtg gcggagctac cttatgatta gggggttcat ccgaacctcc | 1800 |
| ttcgacggaa aattatacta ttttttataag tgaaaattat ttttttatgta tatataattg | 1860 |
| atgttgaacc cccttcggtt agttcatgta tctatatttt tttatttttga accccgatga | 1920 |
| aaatttggc tccgccactg ctacaaggta ggacctccaa caatcaccaa tacctaaatt | 1980 |

```
gcaaaaattt cagtttgttt tttagtttct gttttgggaa gaggaatact acaaggtagg    2040
acctccaaca atcaccaata cctaaattgc aacgttttt agtttctgtt ttgggaagag    2100
gaatactaca tggtagggcc tccaacaatc accaatacct aaattgcaaa aatttcagtt    2160
cgtattttcg tttctatttt gggaagtgga atagtataag gtaggacctc caacaatcac    2220
caatacctaa attaaagttc cgattcattt tttagtttct gttttggaaa gagaaatact    2280
acaaggtagg gcctacaaca atcaccagta cctaaattgt aaaaatttca gttcgttttt    2340
tagtttctat tttgagaaga ggaatgctac aaggtagggc ctacaacaat caccagtacc    2400
taaattgtaa aaatttcagt tcgttttta gtttctgttt tgggaagagg aatactacaa    2460
ggtagggcct tcaacaatca gcaatacc ta aattacaaaa atttcaattc gttttttagt    2520
ttctgttttg ggaagaggaa tactacaagg cagtggcgga gctaccttat gattaggggt    2580
tcatccgaac ctccttcgac ggaaaattat actattttta tatagtaaaa attattttt    2640 atgtatatat aattgatgtt gaaccccctt cggttagttt gtgtatctat attttttat    2700 tttgaacctc cttgataaaa aattttgact ccgccattgc tacaaggtag aacctccaac    2760
aatcaccaat acctaaattg caaaaatttc agttcgtttt ttaatttctg ttttgggaag    2820
aggaatacta caaggcctcc aacaatcacc aatacctaaa ttgcaaaaat ttcagtttgt    2880
tttttagttt ctgttttggg aagaggaata ctacaaggta aggcctccaa caatcaccaa    2940
tacctaaatt gcaaaaattt cagttcgtat tttcgtttct attttgggaa gtggaatagt    3000
ataaggtagg acctccaaca atcaccaata cctaaattgc aaaagttccg attcattttt    3060
tagtttctgt tttggaaaga gaaatactac aaggtagggt ctccaacaat caccagtacc    3120
taaattgtaa aaatttcagt tcgtttttta gtttctattt tgggaagtgg aatagtataa    3180
ggtaggacct ccaacaatca ccaatacct a aattgcaaaa gttccgattc tttttttagt    3240
ttctgttttg gaaagagaaa tactacaagg taggaccttc aacaatcacc aatacctaaa    3300
ttgcaaaaac ttcagttcat ttttagttt ctgttttggg aagaagaata cttcaaggta    3360
acaatcacca atacctaaat taaaatttc agttagtttt ttagtttctg ttttgggaa    3420 gaggaatact ttcttttgct atataaagcc aaagtaggta cctataagca tcaatatttt    3480
gtattgctta gtgattcccc tagttcggta tttcattttt tttcactata ctatatcacc    3540
tcctctcata aatagccatt ataaatcttg cattttctct aatggaaacc cttctaaagc    3600
cttttccatc tccttttactt tccattccta ctcctaacat gtatagtttc aaacacaact    3660
ccacttttcc aaatccaacc aaacaaaag attcaagaaa gttccattat agaaacaaaa    3720
gcagtacaca tttttgtagc tttcttgatt tagcacccac atcaaagcca gagtctttag    3780
atgttaacat ctcatgggtt gatactgatc tggaccgggc tgaattcgac gtgatcatca    3840
ttggaactgg ccctgccggg cttcggctag ctgaacaagt ttctaaatat ggtattaagg    3900
tatgttgcgt tgacccttca ccactttcca tgtggccaaa taattatggt gtttgggttg    3960
atgagtttga aaagttggga ttagaagatt gtctagatca taagtggcct gtgagttgtg    4020
ttcatataag tgatcacaag actaagtatt tggacagacc atatggtaga gtaagtagaa    4080
agaagttgaa gttgaaattg ttgaatagtt gtgttgaaaa tagagtgaag ttttataaag    4140
ccaaggtttt gaaagtgaag catgaagaat ttgagtcttc gattgtttgt gatgatggta    4200
ggaagataag tggtagcttg attgttgatg caagtggcta tgctagtgat tttatagagt    4260
atgacaagcc aagaaaccat ggttatcaag ttgctcatgg gatttagca gaagttgata    4320
```

```
atcatccatt tgatttggat aaaatgatgc ttatggattg gagggattct catttaggta    4380
atgagccata tctgagggtg aagaatacta agaaccaac attcttgtat gcaatgccat    4440
ttgataggaa tttggtattc ttggaagaga cttctttagt gagtcggcct atgttatcgt    4500
atatggaagt gaaagaagg atggtagcaa gattaagaca tttggggatc aaagtgagaa    4560
gtgtccttga ggaagagaag tgtgtgatca ctatgggagg accacttccg cggattcctc    4620
aaaatgttat ggctattggt gggacttcag ggatagttca tccatcgtct gggtacatgg    4680
tggctcgtag catggcattg gcaccagtac tggctgaggc catcgtcgaa agccttggct    4740
caacaagaat gataagaggg tctcaacttt accatagagt ttggaatggt ttgtggcctt    4800
cggatagaag acgtgttaga gaatgttatt gtttcggaat ggagactttg ttgaagcttg    4860
atttggaagg tactaggaga ttgtttgatg cttctcttga tgttgatccc aagtactggc    4920
acgggttcct ttcttcaaga ttgtctgtca aagaacttgc tgtactcagt ttgtacctt    4980 ttggacatgc ctctaatttg gctaggttgg atattgttac aaagtgcact gtcccccttgg    5040 ttaaactgct gggcaatcta gcaatagaga gcctttgaat taatatgata gttttgaagc    5100
actgttttca ttttaatttc ttaggttatt ttcatctttt ctcaatgcaa aagtgaaaca    5160
aaagctatac acattgtcat cgttgttcaa actcagacaa gtttgcctag ctctatgtat    5220
ttatccttaa catatgtatt catcaaattc gaaatataca atgcattgga caaaagtata    5280
gagccacaat ctgataccaa gtctgtattt ggaagcacag gctaattgtt atggttacca    5340
aacactttga attggctgga taataacaaa caggaaattt atgttattaa tcattaacag    5400
caaattggga aagcaagaat tattaggaaa gttaatatag tgtcttggtt attctaatgg    5460
agtgggttat gcaaattaag ttcccttgtc aaagtttggt ttatgaactg ctccactctt    5520
gtccctctta aaagccttaa tcccaacatg taccaccaaa gaattgagct gctccatcag    5580
atcctttgag aatgttaata tgttatttaa atgaaggact gaatgattat gaggatgcaa    5640
tgcataggtt taattaccag ttatctgtaa attgtcttct ttgccattat tttaaaagtt    5700
taataacaag tgtaacatct acaaagagtt gataattaca aagcagctac tagttttagg    5760
```

<210> SEQ ID NO 55
<211> LENGTH: 498
<212> TYPE: PRT
<213> ORGANISM: Capsicum annuum

<400> SEQUENCE: 55

```
Met Glu Thr Leu Leu Lys Pro Phe Pro Ser Pro Leu Leu Ser Ile Pro
1               5                   10                  15

Thr Pro Asn Met Tyr Ser Phe Lys His Asn Ser Thr Phe Pro Asn Pro
            20                  25                  30

Thr Lys Gln Lys Asp Ser Arg Lys Phe His Tyr Arg Asn Lys Ser Ser
        35                  40                  45

Thr His Phe Cys Ser Phe Leu Asp Leu Ala Pro Thr Ser Lys Pro Glu
    50                  55                  60

Ser Leu Asp Val Asn Ile Ser Trp Val Asp Thr Asp Leu Asp Gly Ala
65                  70                  75                  80

Glu Phe Asp Val Ile Ile Gly Thr Gly Pro Ala Gly Leu Arg Leu
                85                  90                  95

Ala Glu Gln Val Ser Lys Tyr Gly Ile Lys Val Cys Cys Val Asp Pro
            100                 105                 110

Ser Pro Leu Ser Met Trp Pro Asn Asn Tyr Gly Val Trp Val Asp Glu
        115                 120                 125
```

Phe Glu Lys Leu Gly Leu Glu Asp Cys Leu Asp His Lys Trp Pro Val
    130                 135                 140

Ser Cys Val His Ile Ser Asp His Lys Thr Lys Tyr Leu Asp Arg Pro
145                 150                 155                 160

Tyr Gly Arg Val Ser Arg Lys Lys Leu Lys Leu Lys Leu Leu Asn Ser
                165                 170                 175

Cys Val Glu Asn Arg Val Lys Phe Tyr Lys Ala Lys Val Leu Lys Val
                180                 185                 190

Lys His Glu Glu Phe Glu Ser Ser Ile Val Cys Asp Asp Gly Arg Lys
                195                 200                 205

Ile Ser Gly Ser Leu Ile Val Asp Ala Ser Gly Tyr Ala Ser Asp Phe
210                 215                 220

Ile Glu Tyr Asp Lys Pro Arg Asn His Gly Tyr Gln Val Ala His Gly
225                 230                 235                 240

Ile Leu Ala Glu Val Asp Asn His Pro Phe Asp Leu Asp Lys Met Met
                245                 250                 255

Leu Met Asp Trp Arg Asp Ser His Leu Gly Asn Glu Pro Tyr Leu Arg
                260                 265                 270

Val Lys Asn Thr Lys Glu Pro Thr Phe Leu Tyr Ala Met Pro Phe Asp
                275                 280                 285

Arg Asn Leu Val Phe Leu Glu Glu Thr Ser Leu Val Ser Arg Pro Met
290                 295                 300

Leu Ser Tyr Met Glu Val Lys Arg Arg Met Val Ala Arg Leu Arg His
305                 310                 315                 320

Leu Gly Ile Lys Val Arg Ser Val Leu Glu Glu Lys Cys Val Ile
                325                 330                 335

Thr Met Gly Gly Pro Leu Pro Arg Ile Pro Gln Asn Val Met Ala Ile
                340                 345                 350

Gly Gly Thr Ser Gly Ile Val His Pro Ser Ser Gly Tyr Met Val Ala
                355                 360                 365

Arg Ser Met Ala Leu Ala Pro Val Leu Ala Glu Ala Ile Val Glu Ser
                370                 375                 380

Leu Gly Ser Thr Arg Met Ile Arg Gly Ser Gln Leu Tyr His Arg Val
385                 390                 395                 400

Trp Asn Gly Leu Trp Pro Ser Asp Arg Arg Val Arg Glu Cys Tyr
                405                 410                 415

Cys Phe Gly Met Glu Thr Leu Leu Lys Leu Asp Leu Glu Gly Thr Arg
                420                 425                 430

Arg Leu Phe Asp Ala Phe Phe Asp Val Asp Pro Lys Tyr Trp His Gly
                435                 440                 445

Phe Leu Ser Ser Arg Leu Ser Val Lys Glu Leu Ala Val Leu Ser Leu
450                 455                 460

Tyr Leu Phe Gly His Ala Ser Asn Leu Ala Arg Leu Asp Ile Val Thr
465                 470                 475                 480

Lys Cys Thr Val Pro Leu Val Lys Leu Leu Gly Asn Leu Ala Ile Glu
                485                 490                 495

Ser Leu

<210> SEQ ID NO 56
<211> LENGTH: 1983
<212> TYPE: DNA
<213> ORGANISM: Capsicum annuum

<400> SEQUENCE: 56

```
atgtatgcat cgtctgccag ggacggtatc ccggggaaat ggtgtaacgc tcgccgtaag      60
cagctacctt tattgatatc caaggacttt cctgcagagt tgtatcattc tttaccttgt     120
aagagtttgg aaaatgggca tatcaagaag gttaaaggag taaaagccac actagctgaa     180
gctccagcta ctcctacaga gaagagtaac tctgaggttc cacagaagaa gttgaaagta     240
cttgtggcag gtggtgggat tggaggatta gttttgctt tggcaggaaa gaagaggggg      300
tttgatgtgt tagtgtttga gagagatata agtgctataa gaggtgaggg gcaatataga     360
ggtccaattc agatacagag caatgcattg gctgctttgg aagcaattga tatggatgtt     420
gctgaagaga tcatgaatgc tggctgtatc actggtcaaa ggattaatgg cttggtcgat     480
ggtatttctg gcaactggta ttgcaagttt gatacgttca ctccagctgt ggaacgtgga     540
cttcctgtga caagagtcat cagccgcatg actttgcaac agattcttgc acgtctgcag     600
ggggaggatg taattatgaa tgaaagccat gtagtaaatt ttgcggatga tggggagacg     660
gttactgtga atcctgagtt atgccaacaa tacacaggtg atcttctggt tggtgctgat     720
ggcataaggt ctaaggtacg gactaatttg ttcggaccga gtgaactaac ttactctggt     780
tacacttgtt atactggaat tgcagatttc gtccctgctg atattgacac agctggctac     840
cgagtctttt tgggccacaa acagtacttt gtttcttcag atgtgggtgg aggcaagatg     900
cagtggtatg catttcacaa tgaaccagct ggtggtgtgg atgctccaaa cggtaaaaag     960
gaaagattgc ttaaaatatt tgggggatgg tgtgacaacg ttatagacct ttcagtcgcc    1020
acagatgaag atgcaattct tcgtcgtgac atctatgata gaccccccaac atttagttgg   1080
ggaaaaggtc gtgttacatt gcttgggggac tctgtccatg ctatgcagcc taatttgggt   1140
caaggaggat gcatggccat agaggatagc tatcaactag cactggaact tgagaaagca   1200
tggagccgaa gtgctgagtc cggaagccct atggatgtca tctcatcttt acggagctat   1260
gaaagtgcta gaaaactccg agttggagtt atccatggac tggctagaat ggctgcaatc   1320
atggcatcag cttacaaggc ctatcttggt gtcggactgg gtccattatc attcattacc   1380
aagtttagga taccacatcc tggaagagtt ggtggaagta tttttattga cttgggaatg   1440
ccgcttatgt taagctgggt tctaggaggc aacggggaaa agcttgaagg cagaatacaa   1500
cattgcagac tatctgagaa agcaaatgac caattgagaa attggtttga agatgatgat   1560
gctttagagc gtgctactga tgcagagtgg ctattgcttc ctgccgggaa tagcaatgct   1620
gctttagaaa ctctcgtttt aagcagagat gagaacatgc cttgcactat cgggtctgtc   1680
tcacatgcaa acattcctgg aaaatcagtt gttattcctt tgtctcaggt gtccgatatg   1740
cacgcccgga tatcctacaa tggtggcgca tttctcggca ctgctttccg aagtgaccat   1800
ggcacttggt ttatagataa cgaaggcaga agatatcggg tgtctccaaa cttcccaatg   1860
cggtttcatt catcagatgt aatcgtattt ggttctgata aggcagcatt tcgtataaag   1920
gctatgaaat ttgcccccaaa aactgctgca aaagaagatc gtcaagcagt gggggcagct   1980
tag                                                                 1983
```

<210> SEQ ID NO 57
<211> LENGTH: 613
<212> TYPE: DNA
<213> ORGANISM: Capsicum annuum
<220> FEATURE:
<221> NAME/KEY: misc_feature
<222> LOCATION: (59)..(59)
<223> OTHER INFORMATION: n is a, c, g, or t
<220> FEATURE:

```
<221> NAME/KEY: misc_feature
<222> LOCATION: (475)..(475)
<223> OTHER INFORMATION: n is a, c, g, or t

<400> SEQUENCE: 57
ctgtagctcc acattgcttc ctacatagga cttgctcaga atagaactcg aaaaagagna      60
ccaattgaat gtaaatactt caacaactta ggtagggaca tcttatattg ctaaatacag     120
tgcccactct gcacagacta ggcatacaaa gcattccggc ccatcttagt gaagaaacat     180
gatatttgtt cacgtccatt agtttgtttg tacccgtctt tagttgttat ctattcgtga     240
tatcaagaat ataaagactg ggtggcttat tcacgtaaat tgtagtcctt gcctcagtag     300
taaaattttg tttcytgtca atagaggtac agtctttaga ttcaacttcc tcccttgtcc     360
atgcagtttg tgcttcttct gatgttgcgt acaatgctgc caataatcgt cggtgttgct     420
ggagataact cggtaatatt ggtcatggtt agtgtcacag ttatatttcc tttgnaaatg     480
aaaattctgc ttttccctcg gttcatttat atgttcatct ttatagttat tagtgttgaa     540
agctattgga atcctactgg cagtctatgt tgtggtgaaa acttttattg ctgtacgaca     600
tcggaggcat cag                                                       613

<210> SEQ ID NO 58
<211> LENGTH: 2007
<212> TYPE: DNA
<213> ORGANISM: Capsicum annuum

<400> SEQUENCE: 58
ggggatcgac attgatccaa ctgccaaaat tgtccttagg acagtaagga gtatgagaca      60
atccattaga tctagctcct ccttccctac atgcagatga ccctaaccag tggatcgata     120
aatttccttt aaccattggc taaaagtgag ttgagaaaaa ataaagaga aacctaattt      180
acttccctca gtgaccccctt tgtcttccat gcttcaagta tgtgtaccct tgacatgttt     240
ctgctgctat ggttatcaga caatgcgacg atgcatttct gcatccgtgg tgtgttttct     300
tctgtgcctt ttgacatcgt gtttcatttt cctctttatg tttgctaaca gtttgatttt     360
aagaggcctt gctaaagaga tggatgtctt ctgtttctta cgagctatct ctgcttcttt     420
agcccttcaa gataccttaa cagtgcattt gttaatactc tcttgtagca ctagcagata     480
actactgcat ataccatttc tatttctctt cttcttgtta agtaattgc cgtagttgta      540
ctactgatcg ttctagtctc ttgaaaatac tgctatcctg cctttttcttg aatcattacc    600
ttttgaagaa ctcagcacat ttttttcagtt tggtgtctct gaggcatgat taaccacttt    660
caataaaaat ttacatgcat atgacagaat gtgtatgcac tgactttgtt ggaacctaag     720
taaacagcaa ccatcttcat gccttttcttg accaaagaag ttgctgacac ggctttgaca    780
tctgcatgtt tgttatccac agttcagaag ttacagccta catcctctag acctcactca     840
ataatttagc aactttttcct tgcattatgt gtttacttcc attttgtttga tcatttactt    900
ggttaacatg tagaattgga gttgtatctg ggaaagctat atttgcacaa ccacttgatg     960
aatattggaa gaagaaactt caggagaaac cagccgcaaa agaaaatgat gtaagcacct    1020
catagcgttt ggtgatctga gcttaatatc gtagtatttt tctgttggcc gttactctat    1080
aaaaatgcct tgtgtatcca caacctcatc caaataacta attacatgat gctctagaaa    1140
tttcatcctt cagttgtttg tatgagactg cccatcaaaa ctatccacgt ttttaatctt    1200
gtcgcgaaat attacatatc aattgggata aaattgtgcc catgttactt tacgtttctt    1260
tgaagtattt ggatgaagta ttcatgtggt cagaaccaaa attgatcatt tagaaaggat    1320
```

```
gctgattact gaatgtaatg tcatcaagca taatttgttc ctttaatttg gaattatctg    1380
tactcggcac tagtgtgtgt cccttteectt ggttctgttg tgcactggct tggcgctaat    1440
ttagaacatc tgcattaaac gcctggacta aatgctgata tttaatgctg aaatgtgtgt    1500
aataatcaca attgacgctg ggtaatatag attttcatca gattataatc ttacagatga    1560
tctccatgag gtagggtcag tgggttaagg gttctctttt atagtgtaaa agttaattta    1620
ttcgtttagt tggttgcaga gcattacata gcttttaata ttctctttac ttaacagaac    1680
tatgatcact tcaactgagt gaagaaaagg aaaagaacca ctgacaggag acagagaaat    1740
tacgggcata attacattca ctcgacaaac atgaattgaa atacaatcaa tcaacaagga    1800
caaaccaatg atatacagyt gtactatcca agattccctt ggcaaaagaa tgtaatactc    1860
taggaagttt aacaaataaa aagttgtctt cccaagattc taatcgaaac ttctaatttg    1920
gaaccaagat ccaaggacca ttaagtatgt gtaaacatag agagaggcat atactaacag    1980
tagtagaaga tttcccaccc acatacc                                        2007

<210> SEQ ID NO 59
<211> LENGTH: 336
<212> TYPE: DNA
<213> ORGANISM: Capsicum annuum

<400> SEQUENCE: 59
gtcaattctt tgtttcttgc agagctagta ctttttgtct tgttggacca atcccttac      60 aytggagggg gtccttgttt gctttctcct ctgaaaaatg tacgtattga ctgcaacatg    120
gtctacaagg aagaactttc ttttgcatat acaacaatag agacgttaat aaattctctt    180
tggaaaacta ctttattact gttctgatta ttcaatagct acttggatca ataatgatgt    240
aagagacaca atagcaatac taggtttagg gacttgtgtt atcttctctt tgttgcattc    300
agaatgaagg gacgattcta taactgctgt ctgtca                              336

<210> SEQ ID NO 60
<211> LENGTH: 963
<212> TYPE: DNA
<213> ORGANISM: Capsicum annuum

<400> SEQUENCE: 60
ggttttcttg tttgcatgcg ccattgctct tctagcttct tcatcaatgg tttctgctga     60
agttatcgag cattcttttc aagtatataa ctctcctctt tttatttcct atttatgcaa    120
attaggttct ccttttttgc accccatctc gagaaaataa atatgaaatt tacatatata    180
tatatataga ggtgtcaaaa aaaaagtttg tgttaataaa tgagtatgct attgactcac    240
ccaattgtta tttgagttga aatggattaa acgatgggtc ataacctaac tcttcttttt    300
ttgcaatttg tctaagtata gccctaagta atttttttttt ctttgtcctg gttatacata    360
acatatcaaa tagaagttta tttctggaaa aaaagacatt ttaacaaggt aaatgttttg    420
tgaagacttt ccttttgatc caagggtcta gcggaagcaa cctttcaacc tcacaagagt    480
cggggtgaag tttgtataca tcccactccg tcagacctca ttgtggtatt acaatggata    540
agctattgtt gttgttgtaa atgttttgtg agtgataaga ttatgtattt ggttggtgta    600
ggtgcaaaac cttactataa acaggttatg ccgtagacaa gtaataaatg cagtaaatgg    660
aagtcttcct ggtccaactc tacatgtacg tgagggcgac accmttgttg ttcatgtctt    720 caataaaatta ccatacgatc tcactatcca ttggtatgtc attcacgtta atttaattaa    780
```

```
aggatttaac ttatatacat tgctagcgca tagaaatttt atactatcaa tgtttaatta    840
atcacaagag gttgttattt cattttaat atcaaaatta ataccatact aaagcgtaac    900
```


```
aggatttaac ttatatacat tgctagcgca tagaaatttt atactatcaa tgtttaatta    840
atcacaagag gttgttattt cattttaat atcaaaatta ataccatact aaagcgtaac    900
gtgtggttac cataagatct ccaatcaaat ctttcttct ttttcctatc aaatttcact    960
ttc                                                                  963

<210> SEQ ID NO 61
<211> LENGTH: 2014
<212> TYPE: DNA
<213> ORGANISM: Capsicum annuum

<400> SEQUENCE: 61
ggatgtaata atcattttg ttttatctga ggaagtatga agaagagtaa tacttcaccc     60
aaaagcttca ttaataaaat tcagaaaggt aaacagtaac ttacagtatc aactggaatt    120
gaaaagccaa cacccgatga tgcaccggaa ggagaatata tagcagtatt tattccaata    180
aggtttccag aactatctag aagtggtcct ccactgttac cgggattgat tgctgcgtct    240
gtctgaataa catcttggat tggacggcca gtagctgcag aattgatttc tcttctaagg    300
ccactagaaa catataaatt aatcagttat attaaagaaa atgtatgata aatagcatat    360
actttataca wcaccaacac atcttgcttt tgcgtataat atatccattt actgcgagat    420
atggttattg catatgtaat acgtttgctt cttggatttt atggatgcaa ggctctagac    480
agtgacaacc aaccaatcta tcctataaca atctgctttc tgccatattt cagaaatgaa    540
aacaaaaggt ggaccttacg gaaagatgag gagtattgga cacacttgaa agatataatc    600
tccctttgtc gttcaaaaag caagaaaaag atagagatca agaaagccac caacattgaa    660
aaactcgtat ttcagttgaa atggatgaag aagattaatc aaaactctct acttcatctc    720
aattctaaac aaaggaaaga aggttacttc atttttattt atttaattttc ctctcattta    780 cttccttcac tttgttagtc attaattcca caagccttct accaagattt tgagtgtccc    840
atattcattt tattttatct cctatcttca cacaacactg ttagcaccat ttcactggaa    900
tatctgaaca ttaggaactt gtgcacaata atatgaaata agtaaatacc tgataacacc    960
agtggtgagt gtatgatcaa gtccaaactg caacatattt acataaaaga ccagtcatca   1020 ggtgttcca gatgaaaatt aaaagagaag taaatatta atgtttcata gtaaattata    1080
cgaatacaga ggaaaaagag gcgtgaaggg gggaaggcta cccaaatata agaaacatgc   1140
acccatttca acaagagatc tagttccaat gtgtaagtca agtacgttga ttttaatgta   1200
agtcagtgcg aaattttggc agaagttgga gcactagatt aaaggaggga attgttatgc   1260
tctaaacttg ggggaaaaca agcagttaaa aatattagca ggctggtaaa ggttcagaag   1320
tagcagctaa ctttcagatg ggctaatggg caaagatttg aaacagaaga cagaaataag   1380
ttgtactctc tatcagttgt tttttttct tgcacaaatt ttcgtaataa gaaaaatgca   1440
ctagaaatct gtatgcaaag ttatactttc taactgttgt aatgctcatg aacgcctgca   1500
agccaaattg catagactct gcatttcgat gccgcacgcg tgtcggatgc tccaaaaata   1560
cacttctttt tatatttgga gaatccggca cgcacccact gacattttg aagagtccaa   1620 gcaacatagc ctgcaagaca attgttttct cgaaagcaag gactgaatat gaatggacc   1680 aaactagttt agagaaggga caatagacca gactaaaagc gctatcatta aaagggtag   1740 ctcggtgcac taaagctatt gctatgcgcg gtgtccggag aagggcccca ccacaagggt   1800
gtatcgtacg cagcccttacc ttgcatttct gccagaggct gtttccaaga ctttaacccg   1860
tgacctcctg ataacatgac aacaacttta ccagttactc caaggctccc cttcaaaagt   1920
```

```
gctatcatta catgaataga attctctatc aggtttgtat ttcatcacat acaggatttc    1980
caatagcaaa tacttttga ccaacgagca agtc                                 2014
```

<210> SEQ ID NO 62
<211> LENGTH: 1216
<212> TYPE: DNA
<213> ORGANISM: Capsicum annuum

<400> SEQUENCE: 62

```
ccttagcttg cgtctctctt gatctcgatt cctctggtgc ttcttttgaa ttacattcca      60
attctttctc gttttttgtaa ttttcttgac ttttggcctc tgcacccagt tgcacatatg    120
gggtaatgct gtctttgggc gtaccattga cgccagtgct gcttgttgga acagtttcct    180
ccctctctaa tgtaagtaga ggatatgctg cttgatcttg tagctgctta gttgcattgc    240
tttcactgct caccatgtta tccattgcta tctccttttc cggaaccta acagatgtca     300
atgatgtcaa atgttctgtt atttcttctt gctcattcct tgttttttcc tcttgttcac    360
ctcctacttg ggtaattgga gcattttcag tctttaattc ttctttctgt gtttcttttg    420
tttcatcgca tgttatcatc tctccgaaac ctgctgctgt ttttctttct gatccaaaag    480
gttccaaact tcctctttca ggttcacttg ttgttgttcc ctgctcttgc tgtacctgtg    540
ttgtgytgtt gtttgaggaa tcttggccgg tgctctctct taagtcttct tcttgttcct    600
cctatgagtt catatcttac cgtcagaaat cttgattgaa ttgttgcgcg agtaaatagg    660
ggagacagag gggtgtatga aaagattgga ataatgtatt tgcttctat ttttttagct     720
tttttcctca ctgttatag tctagatcca gttttataat tcagaattat gatttcttgt    780
agcagattgc aaatcggcat ttatgttata ctctgcctgt gtatatgaaa tgtttcatgc    840
agttgaccat gcataatgtt ttcacggcaa catcttttca atccctctt tgcacgagaa    900
tacaaaaact gaaataata tatagtcatc tagagatttg tgaccttaac taacttggag    960
ttgtggctta gatgttgtca tcgttgttgt tctgaaatat tgtgcagcag gagaaccaaa  1020
tttctaggtt cataaacatg caataaactc atagattctc agtagatgct aatcagctaa  1080
cgttgtaagt tcttgttcat ttaccttgtt agtattgtcc tccaccctca tttcttctga  1140
agaaagttca attgcgttct ccactccacg cacgtcttta acctcttctg tggttaggtt  1200
ggcttttga aggttc                                                    1216
```

<210> SEQ ID NO 63
<211> LENGTH: 25
<212> TYPE: DNA
<213> ORGANISM: Artificial sequence
<220> FEATURE:
<223> OTHER INFORMATION: primer

<400> SEQUENCE: 63

```
cgtaaattgt agtccttgcc tcagt                                           25
```

<210> SEQ ID NO 64
<211> LENGTH: 25
<212> TYPE: DNA
<213> ORGANISM: Artificial sequence
<220> FEATURE:
<223> OTHER INFORMATION: primer

<400> SEQUENCE: 64

```
ggacaaggga ggaagttgaa tctaa                                           25
```

<210> SEQ ID NO 65
<211> LENGTH: 19
<212> TYPE: DNA
<213> ORGANISM: Artificial sequence
<220> FEATURE:
<223> OTHER INFORMATION: Primer

<400> SEQUENCE: 65
ctctattgac aagaaacaa                                              19

<210> SEQ ID NO 66
<211> LENGTH: 17
<212> TYPE: DNA
<213> ORGANISM: Artificial sequence
<220> FEATURE:
<223> OTHER INFORMATION: Primer

<400> SEQUENCE: 66
ctattgacag gaaacaa                                                17

<210> SEQ ID NO 67
<211> LENGTH: 23
<212> TYPE: DNA
<213> ORGANISM: Artificial sequence
<220> FEATURE:
<223> OTHER INFORMATION: Primer

<400> SEQUENCE: 67
ctggtccaac tctacatgta cgt                                         23

<210> SEQ ID NO 68
<211> LENGTH: 29
<212> TYPE: DNA
<213> ORGANISM: Artificial sequence
<220> FEATURE:
<223> OTHER INFORMATION: Primer

<400> SEQUENCE: 68
ccaatggata gtgagatcgt atggtaatt                                   29

<210> SEQ ID NO 69
<211> LENGTH: 16
<212> TYPE: DNA
<213> ORGANISM: Artificial sequence
<220> FEATURE:
<223> OTHER INFORMATION: Primer

<400> SEQUENCE: 69
agggcgacac cattgt                                                 16

<210> SEQ ID NO 70
<211> LENGTH: 16
<212> TYPE: DNA
<213> ORGANISM: Artificial sequence
<220> FEATURE:
<223> OTHER INFORMATION: Primer

<400> SEQUENCE: 70
agggcgacac ccttgt                                                 16

<210> SEQ ID NO 71
<211> LENGTH: 28
<212> TYPE: DNA
<213> ORGANISM: Artificial sequence
<220> FEATURE:
<223> OTHER INFORMATION: Primer

<400> SEQUENCE: 71
caatcaatca acaaggacaa accaatga                                  28

<210> SEQ ID NO 72
<211> LENGTH: 29
<212> TYPE: DNA
<213> ORGANISM: Artificial sequence
<220> FEATURE:
<223> OTHER INFORMATION: Primer

<400> SEQUENCE: 72
ctagagtatt acattctttt gccaaggga                                 29

<210> SEQ ID NO 73
<211> LENGTH: 22
<212> TYPE: DNA
<213> ORGANISM: Artificial sequence
<220> FEATURE:
<223> OTHER INFORMATION: Primer

<400> SEQUENCE: 73
atcttggata gtacagctgt at                                        22

<210> SEQ ID NO 74
<211> LENGTH: 22
<212> TYPE: DNA
<213> ORGANISM: Artificial sequence
<220> FEATURE:
<223> OTHER INFORMATION: Primer

<400> SEQUENCE: 74
atcttggata gtacaactgt at                                        22

<210> SEQ ID NO 75
<211> LENGTH: 27
<212> TYPE: DNA
<213> ORGANISM: Artificial sequence
<220> FEATURE:
<223> OTHER INFORMATION: Primer

<400> SEQUENCE: 75
gtactttttg tcttgttgga ccaatcc                                   27

<210> SEQ ID NO 76
<211> LENGTH: 24
<212> TYPE: DNA
<213> ORGANISM: Artificial sequence
<220> FEATURE:
<223> OTHER INFORMATION: Primer

<400> SEQUENCE: 76
accatgttgc agtcaatacg taca                                      24

<210> SEQ ID NO 77
<211> LENGTH: 16
<212> TYPE: DNA
<213> ORGANISM: Artificial sequence
<220> FEATURE:
<223> OTHER INFORMATION: Primer

<400> SEQUENCE: 77 cccctccaa tgtaaa                                                16

<210> SEQ ID NO 78

```
<211> LENGTH: 16
<212> TYPE: DNA
<213> ORGANISM: Artificial sequence
<220> FEATURE:
<223> OTHER INFORMATION: Primer

<400> SEQUENCE: 78 cccccctccag tgtaaa                                                        16

<210> SEQ ID NO 79
<211> LENGTH: 35
<212> TYPE: DNA
<213> ORGANISM: Artificial sequence
<220> FEATURE:
<223> OTHER INFORMATION: Primer

<400> SEQUENCE: 79
tcagttatat taaagaaaat gtatgataaa tagca                                    35

<210> SEQ ID NO 80
<211> LENGTH: 31
<212> TYPE: DNA
<213> ORGANISM: Artificial sequence
<220> FEATURE:
<223> OTHER INFORMATION: Primer

<400> SEQUENCE: 80
gcagtaaatg gatatattat acgcaaaagc a                                        31

<210> SEQ ID NO 81
<211> LENGTH: 19
<212> TYPE: DNA
<213> ORGANISM: Artificial sequence
<220> FEATURE:
<223> OTHER INFORMATION: Primer

<400> SEQUENCE: 81
atgtgttggt gttgtataa                                                      19

<210> SEQ ID NO 82
<211> LENGTH: 19
<212> TYPE: DNA
<213> ORGANISM: Artificial sequence
<220> FEATURE:
<223> OTHER INFORMATION: Primer

<400> SEQUENCE: 82
atgtgttggt gatgtataa                                                      19

<210> SEQ ID NO 83
<211> LENGTH: 22
<212> TYPE: DNA
<213> ORGANISM: Artificial sequence
<220> FEATURE:
<223> OTHER INFORMATION: Primer

<400> SEQUENCE: 83
gttgttccct gctcttgctg ta                                                  22

<210> SEQ ID NO 84
<211> LENGTH: 20
<212> TYPE: DNA
<213> ORGANISM: Artificial sequence
<220> FEATURE:
<223> OTHER INFORMATION: Primer

<400> SEQUENCE: 84
```

```
caccggccaa gattcctcaa                                                      20

<210> SEQ ID NO 85
<211> LENGTH: 18
<212> TYPE: DNA
<213> ORGANISM: Artificial sequence
<220> FEATURE:
<223> OTHER INFORMATION: Primer

<400> SEQUENCE: 85
cctgtgttgt gttgttgt                                                        18

<210> SEQ ID NO 86
<211> LENGTH: 17
<212> TYPE: DNA
<213> ORGANISM: Artificial sequence
<220> FEATURE:
<223> OTHER INFORMATION: Primer

<400> SEQUENCE: 86
ctgtgttgtg ctgttgt                                                         17

<210> SEQ ID NO 87
<211> LENGTH: 526
<212> TYPE: DNA
<213> ORGANISM: Capsicum annuum

<400> SEQUENCE: 87
cccaataayc caatactaat aacttaataa tattttatc ggttcgattt atcgatcggc            60
tcaactacca aaggaacaa aaaataaat agagtactac aacaaccata gatgagtgaa            120
caagcgtcaa acatcagcct cagtttagta acccaaacaa gctacaatga caagccacct         180
ggccataaaa tcttcaccat tgctgcttca tggaccattg attggttctc aatcttcttt         240
gccccaccac caccaccacc ctcactatca cccacaattt ccacttcctt tttttccctcc        300
tcaaaagcct aactaacaca cattggccta actaaaattc cataaatca ccttcacttc          360
tttttttcat tagattatac attagttgtt tggtctcaat cttcctttca cttcctttgg         420
cctaattaac agtttatata aatcaacttc acttcttttt ttcactaaaa catacagtga         480
aagagaaaca caagagtctt ttcttgaact ggagttctag tgaaag                        526

<210> SEQ ID NO 88
<211> LENGTH: 638
<212> TYPE: DNA
<213> ORGANISM: Capsicum annuum

<400> SEQUENCE: 88
taaaaaatag tagttaattt tgaatgaaga cttacaaata cgaaaatcta taaagaaat           60
tcatgaagga aactggccta taattgtata tacatagaga attagtatat atttaggaaa         120
tggtagaata agaaacaatg accatcactt tctctataca tttaggaaat ggtagaataa        180
gaaacaatga ccatcacttt ttccacgttc tttagaagaa agccaaataa tctctgtatt         240
tgttgaatct gttttgttta tcaatcttct acaatgtctg atgtttctat aaaatgctgt        300
acaaatttcc cgtttatgct gtccccacga ctttgcgctc ttccttcgct tcagcagttt         360
ttgaaggaaa tttcattgtc tttacacgaa atgctgccyg cataacataa acaaatggat        420
ttgaatgagt aataagctac tgccaatgcc aacgtatctt ttaaagcata tcaagcaaga        480
atttcacgaa tcacacctta tcagaaccaa atacgattac atctgatgaa tgaaaacgca        540
```

```
tagggaagtt tggagacacc cgatatcttc tgccttcatt actacataat gcagaacaat    600
gtaattcttt tgtcttcata gactaataaa tgtgatgc                            638

<210> SEQ ID NO 89
<211> LENGTH: 509
<212> TYPE: DNA
<213> ORGANISM: Capsicum annuum

<400> SEQUENCE: 89
ggcagcattt cgtgtaaaga caatgaaatt tccttcaaaa actgctgaag cgaaggaaga     60
gcgcaaagtc gtggggacag cataaacggg aaatttgtac agcatttat agaaacatca    120 gacattgtag aagattgata aacaaaacag attcaacaaa tacagagatt atttggcttt    180
cttctaaaga acgtggaaaa agtgatggtc attgtttctt attctaccat ttcctaaatg    240
tatagagaaa gtgatggtca ttgtttctta ttctaccatt tcctaaatat atactaattc    300
tctatgtata tacaattata ggccagtttc cttcatgaat ttcttttata gattttcgta    360
tttgtaagtc ttcattcaaa attaactact atttttact tttatttcta acktgcatta    420 tttttactt ttatttctaa cttgcatttt atgttcattg ttgatttat acataataaa    480 atgaaacaaa tagaaaaaaa taataaatt                                     509

<210> SEQ ID NO 90
<211> LENGTH: 5
<212> TYPE: DNA
<213> ORGANISM: Capsicum annuum

<400> SEQUENCE: 90 caggc                                                                 5

<210> SEQ ID NO 91
<211> LENGTH: 5
<212> TYPE: DNA
<213> ORGANISM: Capsicum annuum

<400> SEQUENCE: 91 cgggc                                                                 5

<210> SEQ ID NO 92
<211> LENGTH: 29
<212> TYPE: DNA
<213> ORGANISM: Artificial sequence
<220> FEATURE:
<223> OTHER INFORMATION: Primer

<400> SEQUENCE: 92
cagcagtttt tgaaggaaat ttcattgtc                                      29

<210> SEQ ID NO 93
<211> LENGTH: 25
<212> TYPE: DNA
<213> ORGANISM: Artificial sequence
<220> FEATURE:
<223> OTHER INFORMATION: Primer

<400> SEQUENCE: 93
ggcattggca gtagcttatt actca                                          25

<210> SEQ ID NO 94
<211> LENGTH: 17
<212> TYPE: DNA
<213> ORGANISM: Artificial sequence
```

<220> FEATURE:
<223> OTHER INFORMATION: Probe

<400> SEQUENCE: 94
atgttatgcg ggcagca                                                17

<210> SEQ ID NO 95
<211> LENGTH: 17
<212> TYPE: DNA
<213> ORGANISM: Artificial sequence
<220> FEATURE:
<223> OTHER INFORMATION: Probe

<400> SEQUENCE: 95
atgttatgca ggcagca                                                17

<210> SEQ ID NO 96
<211> LENGTH: 5752
<212> TYPE: DNA
<213> ORGANISM: Capsicum annuum

<400> SEQUENCE: 96
cccaataacc caatactaat aacttaataa tattttatc ggttcgattt atcgatcggc      60
tcaactacca aaggaacaa aaaataaat agagtactac aacaaccata gatgagtgaa     120
caagcgtcaa acatcagcct cagtttagta acccaaacaa gctacaatga caagccacct     180
ggccataaaa tcttcaccat gctgcttca tggaccattg attggttctc aatcttcttt     240
gccccaccac caccaccacc ctcactatca cccacaattt ccacttcctt ttttccctcc     300
tcaaaagcct aactaacaca cattggccta actaaaattc tcataaatca ccttcacttc     360
ttttttcat tagattatac attagttgtt tggtctcaat cttcctttca cttcctttgg     420
cctaattaac agtttatata aatcaacttc acttcttttt ttcactaaaa catacagtga     480
aagagaaaca caagagtctt ttcttgaact ggagttctag tgaaagatgt attcaactgt     540
gttttacact tcagttcatc cctccacttc agttttttca agaaaacagc tacctttatt     600
gatatccaag gactttcctg cagagttgta tcattcttta ccttgtaaga gtttggaaaa     660
tgggcatatc aagaaggtta aaggagtaaa agccacacta gctgaagctc cagctactcc     720
tacagagaag agtaactctg aggttccaca gaagaagttg aaagtacttg tggcaggtgg     780
tgggattgga ggattagttt ttgctttggc agcaaagaaa aaggggtttg atgtattggt     840
gtttgagaga gatttaagtg ctataagagg tgaggggcaa tatagaggtc caattcagat     900
acagagcaat gcattggctg cttttggaagc aattgatatg gatgttgctg aagagatcat     960
gaatgctggc tgtatcactg gtcaaaggat taatggcttg gtcgatggta tttctggcaa    1020
ctggtaaatt cacatcactc tgatttgatt gtgctgatta agagcttgtg tgccttttt    1080
gctactgtat ttactttcca aacttgttcg gttatgcttt acttaagccg agggtcttca    1140
ggaatagtct ctctaccttc acgagatatg attaaggtct cgcacgcaa tacccttctc    1200
agaagggtaa tcacactggc tatgttgttg ttgtaattaa atgcttgtct gtcttttttt    1260
agttgagctt taactgagga tacccccagga aaataatgaa ttctttgaaa tatttagccc    1320
tttaaaaaag tatagggaaa ataattcatt tagtcacaag tttattgaat catggttgcc    1380
aagcttattc gggaaaagga tcctatcttt accttcaaat ggcttcaatc agattgataa    1440
gttagtctta ttgttgtatg agcagcttat tgtgagaaca gtcccttat ttcttgaact    1500
gcgaacagtg acaatagttg ggtatcaggt attgcaagtt tgatacgttc actccagctg    1560

```
tggaacgtgg acttcctgtg acaagagtca tcagccgcat gactttgcaa cagattcttg    1620
cacgtgctgt aggggaggat gtaattatga atgaaagtaa tgtagtaaat tttgaggatg    1680
atggggagaa ggtaatgcta ggtttgatct ctttgttttc tgctattctc aaaatatcaa    1740
gaaagattat aacttttctt aatttcattt gcatcattgt taattgttgt ttcttattca    1800
tcaattttcg ttaaagcttc tcatgtgctg tgtgaaatca ggttactgtg gttcttgaga    1860
atggacaacg gttacaggt gatcttctgg ttggtgctga tggcataagg tctaaggtat     1920
tcaaaatcag tctcattata tttctttcta ttattactac ttcggttaac aaggatagag    1980
taacttgttt atattttact ttgagattgt ggttccacgt taaaaaattg tctgttgact    2040
gataggcctg agtccgtatt atgcagtgaa ccttttattg attattctag ttgattcaga    2100
agatcacaaa catttccgtt gtgttgtagg tacggactaa tttgttcgga cacagtgaag    2160
ctacttactc tggttacact tgttatactg gaattgcaga tttcgttcct gctgatattg    2220
acacagttgg gtatgatatt ctttcttacc ggattgtgtt tccactcatg cccttatccc    2280
tgctggtgcc gttacactca cacgaggttt tcatagtaga gattaaattg agatttcttt    2340
tctgaaggta ccgagtcttt ttgggccaca aacagtactt tgtttcttca gatgtgggtg    2400
gaggcaagat gcagtggtat gcatttcaca atgaaccagc tggtggtgtg gatgctccaa    2460
acggtaaaat ttttaggccg cttaaaacta tttactatag ttcaggatat agacatactt    2520
actgaaagac gtttttgaat gcttaacttg taacgtttat ttaacccaag gggtttctta    2580 agaattttc ctcattgagg cctggttata gtgttgcaat aaggtaaaga caactcaag     2640 attagaataa gatagactca aatgtattat gagtcggaaa gttttgaatt gaagttgctg    2700
actctatgaa ttaggagttg tttaatattt tgtctgttca tgctgcaggt aaaaaggaaa    2760
gattgcttaa aatatttggg ggatggtgtg acaacgttat agacctatta gttgccacag    2820
atgaagatgc aattcttcgt cgtgacatct atgatagacc gccaacattt aattggggaa    2880
gaggtcgtgt tacattgctt ggggactcag tccatgctat gcagcctaat ttgggtcaag    2940
gaggatgcat ggccatagag gtacaccact gtgtttatca tctttgtcaa atacacagta    3000
ttgtaaggtt gtgtatgaca ctgaacttt ccatgtacaa ctacaggata gctatcaact      3060
agcactggaa cttgagaaag catggagccg aagtgctgag tccggaagcc ctatggatgt    3120
catctcatct ttaaggaggt aatccattat ttattggctc aagtgctgta gtctggttgg    3180
ttgagtacag gctgccagtt catgataatt gaaaaaacat ttgcaattgg ttgaggtctt    3240
taacttcacc ccaccaccag cccagtagga ctgctttaaa tgcctcaact gaaaatggat    3300
tgatttgaac agctgccgtg tctgccagtt cgctgatcct ttaatgaatt tccttttttct   3360 gcagctatga aagtgctaga aaacttcgag ttggagttat ccatggactg gctagaatgg    3420
ctgcaatcat ggcatcaact tacaaggcct atcttggtgt cggacttggt ccattatcag    3480
tatgaaaaac tatctatcac ttgaaattgg aatggcatag ccaatttgcg tgattgcgca    3540
gagctcttct tataatagat gttttttttct attatttgtg cagtttttga ccaagtatag   3600
gataccacat cctggaagag ttggtggaag agtatttgtg gacttgggaa tgcctctaat    3660
gttaagttgg gttctaggag gcaacgggta ggaatatgcg agctgtattc cagcattttc    3720
ttgcttcagt attttgaaca tgattttggt ttctatgtga atccgtgatg agtttgctgg    3780
agatcttgga agttgatatc ctgtggtttg actcgtcttt tttctttct gcagcgaca     3840 agcttgaggg tagaatacaa cattgcaggc tatctgagaa agtatgtagc gtaaggaact    3900
atgcactcaa cacacgaaca cagaaaagat ttctggcttc cattgctact taattaaggt    3960
```

-continued

```
ccaactatgg attttacggg tgtgttaata tactgtactg tggtgatgaa ggcaaatgat    4020
caattgagaa gatggtttga agatgatgat gctttagagc gtgctactga tgcagagtga    4080
gttaatggaa cgtaatattt aaaaatttca tttttacatg tctcatttc ctagtttgct    4140
ttctaatttg gtgcttacgt tttatctttc aggtggttac tgttacctgc agcgaatggc    4200
aattctgctt tagaaactat tgttttaagc agagatgagg atgtcccttg cactatcggg    4260
tatgctttta ggttacggct tattggaaag attgttcata gctttgctgt tagatcctgg    4320
cagtttgcac aaagtaatct tgttaacgt ttggttcata tgagtaagag gtacaacatt    4380
taaatgactt aattcccctt tgagaagatg gttgaagtca ttttattggc taaatgaaca    4440
tttaaagcaa gagtataaag gctacacagc atgacatctt tcttagatta tctgaattca    4500
tacttaaagc tcttaatgta tgcataacta tacaaaaaaa ttcatgcatc gtgatgcatc    4560
cattgcaaat atatccccat caatctccta gctctaatca acaaatccga tccatgcgca    4620
tcctatcaaa agtgcgtaga cattaatgga atgccacttt gcccaacttg gctgtaaggg    4680
aagaaacttg aatgaggtat tgtttcatta gaagagctac taacgtcttt aggtttcagg    4740
tctgtctcgc atacaaacat tcccggaaaa tcagtagttt tacctttgcc acaggtgatt    4800
gctatagctc agtatcctgg acattcttgt ggttaatgca tggcttagat tgtctatttt    4860
ctttgttaat cacaggtgtc tgaaatgcat gcccaaatat cctgcaaaaa caacgcatt    4920
tttgtaactg attttcagag tgaacatggt acttgggtta tagagtaagc tccatgagtt    4980
ctttatacaa ctgtactata agtgcatcac atttattagt ctatgaagac aaaagaatta    5040
cattgttctg cattatgtag taatgaaggc agaagatatc gggtgtctcc aaacttccct    5100
atgcgttttc attcatcaga tgtaatcgta tttggttctg ataaggtgtg attcgtgaaa    5160
ttcttgcttg atatgcttta aaagatacgt tggcattggc agtagcttat tactcattca    5220
aatccatttg tttatgttat gcgggcagca tttcgtgtaa agacaatgaa atttccttca    5280
aaaactgctg aagcgaagga agagcgcaaa gtcgtgggga cagcataaac gggaaatttg    5340
tacagcattt tatagaaaca tcagacattg tagaagattg ataaacaaaa cagattcaac    5400
aaatacagag attatttggc tttcttctaa agaacgtgga aaaagtgatg gtcattgttt    5460
cttattctac catttcctaa atgtatagag aaagtgatgg tcattgtttc ttattctacc    5520
atttcctaaa tatatactaa ttctctatgt atatacaatt ataggccagt ttccttcatg    5580
aatttctttt atagatttc gtatttgtaa gtcttcattc aaaattaact actatttttt    5640
acttttattt ctaacttgca ttattttta ctttatttc taacttgcat tttatgttca    5700
ttgttgattt tatacataat aaaatgaaac aaatagaaaa aaataataaa tt            5752
```

<210> SEQ ID NO 97
<211> LENGTH: 5752
<212> TYPE: DNA
<213> ORGANISM: Capsicum annuum

<400> SEQUENCE: 97

```
cccaataatc caatactaat aacttaataa tatttttatc ggttcgattt atcgatcggc      60
tcaactacca aaaggaacaa aaaaataaat agagtactac aacaaccata gatgagtgaa     120
caagcgtcaa acatcagcct cagtttagta acccaaacaa gctacaatga caagccacct     180
ggccataaaa tcttcaccat tgctgcttca tggaccattg attggttctc aatcttcttt     240
gccccaccac caccaccacc ctcactatca cccacaattt ccacttcctt ttttccctcc     300
```

```
tcaaaagcct aactaacaca cattggccta actaaaattc tcataaatca ccttcacttc    360 ttttttttcat tagattatac attagttgtt tggtctcaat cttcctttca cttcctttgg    420
cctaattaac agtttatata aatcaacttc acttcttttt ttcactaaaa catacagtga    480
aagagaaaca caagagtctt ttcttgaact ggagttctag tgaaagatgt attcaactgt    540
gttttacact tcagttcatc cctccacttc agttttttca agaaaacagc tacctttatt    600
gatatccaag gactttcctg cagagttgta tcattcttta ccttgtaaga gtttggaaaa    660
tgggcatatc aagaaggtta aaggagtaaa agccacacta gctgaagctc cagctactcc    720
tacagagaag agtaactctg aggttccaca gaagaagttg aaagtacttg tggcaggtgg    780
tgggattgga ggattagttt ttgctttggc agcaaagaaa aaggggtttg atgtattggt    840
gtttgagaga gatttaagtg ctataagagg tgaggggcaa tatagaggtc caattcagat    900
acagagcaat gcattggctg cttttggaagc aattgatatg gatgttgctg aagagatcat    960
gaatgctggc tgtatcactg gtcaaaggat taatggcttg gtcgatggta tttctggcaa   1020
ctggtaaatt cacatcactc tgatttgatt gtgctgatta agagcttgtg tgcctttttt   1080
gctactgtat ttactttcca aacttgttcg gttatgcttt acttaagccg agggtcttca   1140
ggaatagtct ctctaccttc acgagatatg attaaggtct gcgcacgcaa tacccttctc   1200
agaagggtaa tcacactggc tatgttgttg ttgtaattaa atgcttgtct gtctttttt    1260 agttgagctt taactgagga taccccagga aaataatgaa ttctttgaaa tatttagccc   1320
tttaaaaaag tatagggaaa ataattcatt tagtcacaag tttattgaat catggttgcc   1380
aagcttattc gggaaaagga tcctatcttt accttcaaat ggcttcaatc agattgataa   1440
gttagtctta ttgttgtatg agcagcttat tgtgagaaca gtccctttat ttcttgaact   1500
gcgaacagtg acaatagttg ggtatcaggt attgcaagtt tgatacgttc actccagctg   1560
tggaacgtgg acttcctgtg acaagagtca tcagccgcat gactttgcaa cagattcttg   1620
cacgtgctgt aggggaggat gtaattatga atgaaagtaa tgtagtaaat tttgaggatg   1680
atggggagaa ggtaatgcta ggtttgatct ctttgttttc tgctattctc aaaatatcaa   1740
gaaagattat aacttttctt aatttcattt gcatcattgt taattgttgt ttcttattca   1800
tcaattttcg ttaaagcttc tcatgtgctg tgtgaaatca ggttactgtg gttcttgaga   1860
atggacaacg gtttacaggt gatcttctgg ttggtgctga tggcataagg tctaaggtat   1920
tcaaaatcag tctcattata tttctttcta ttattactac ttcggttaac aaggatagag   1980
taacttgttt atattttact ttgagattgt ggttccacgt taaaaaattg tctgttgact   2040
gataggcctg agtccgtatt atgcagtgaa ccttttattg attattctag ttgattcaga   2100
agatcacaaa catttccgtt gtgttgtagg tacggactaa tttgttcgga cacagtgaag   2160
ctacttactc tggttacact tgttatactg gaattgcaga tttcgttcct gctgatattg   2220
acacagttgg gtatgatatt cttcttacc ggattgtgtt ccactcatg cccttatccc     2280 tgctggtgcc gttacactca cacgaggttt tcatagtaga gattaaattg agatttcttt   2340
tctgaaggta ccgagtcttt ttgggccaca acagtactt tgtttcttca gatgtgggtg   2400
gaggcaagat gcagtggtat gcatttcaca atgaaccagc tggtggtgtg gatgctccaa   2460
acggtaaaat tttaggccg cttaaaacta tttactatag ttcaggatat agacatactt    2520
actagaagac gttttgaat gcttaacttg taacgtttat ttaacccaag gggtttctta    2580
agaatttttc ctcattgagg cctggttata gtgttgcaat aaggtaaaga acaactcaag   2640
attagaataa gatagactca aatgtattat gagtcggaaa gttttgaatt gaagttgctg   2700
```

```
actctatgaa ttaggagttg tttaatattt tgtctgttca tgctgcaggt aaaaaggaaa    2760
gattgcttaa aatatttggg ggatggtgtg acaacgttat agacctatta gttgccacag    2820
atgaagatgc aattcttcgt cgtgacatct atgatagacc gccaacattt aattggggaa    2880
gaggtcgtgt tacattgctt ggggactcag tccatgctat gcagcctaat ttgggtcaag    2940
gaggatgcat ggccatagag gtacaccact gtgtttatca tctttgtcaa atacacagta    3000
ttgtaaggtt gtgtatgaca ctgaactttt ccatgtacaa ctacaggata gctatcaact    3060
agcactggaa cttgagaaag catggagccg aagtgctgag tccggaagcc ctatggatgt    3120
catctcatct ttaaggaggt aatccattat ttattggctc aagtgctgta gtctggttgg    3180
ttgagtacag gctgccagtt catgataatt gaaaaaacat ttgcaattgg ttgaggtctt    3240
taacttcacc ccaccaccag cccagtagga ctgctttaaa tgcctcaact gaaaatggat    3300
tgatttgaac agctgccgtg tctgccagtt cgctgatcct ttaatgaatt cctttttct    3360 gcagctatga aagtgctaga aaacttcgag ttggagttat ccatggactg gctagaatgg    3420
ctgcaatcat ggcatcaact tacaaggcct atcttggtgt cggacttggt ccattatcag    3480
tatgaaaaac tatctatcac ttgaaattgg aatggcatag ccaatttgcg tgattgcgca    3540
gagctcttct tataatagat gttttttct attatttgtg cagttttga ccaagtatag    3600 gataccacat cctggaagag ttggtggaag agtatttgtg gacttgggaa tgcctctaat    3660
gttaagttgg gttctaggag gcaacgggta ggaatatgcg agctgtattc cagcattttc    3720
ttgcttcagt atttgaaca tgattttggt ttctatgtga atccgtgatg agtttgctgg    3780
agatcttgga agttgatatc ctgtggtttg actcgtcttt tttctttct tgcagcgaca    3840 agcttgaggg tagaatacaa cattgcaggc tatctgagaa agtatgtagc gtaaggaact    3900
atgcactcaa cacacgaaca cagaaaagat ttctggcttc cattgctact taattaaggt    3960
ccaactatgg attttacggg tgtgttaata tactgtactg tggtgatgaa ggcaaatgat    4020
caattgagaa gatggtttga agatgatgat gctttagagc gtgctactga tgcagagtga    4080
gttaatggaa cgtaatattt aaaaatttca tttttacatg tctcattttc ctagtttgct    4140
ttctaatttg gtgcttacgt tttatctttc aggtggttac tgttacctgc agcgaatggc    4200
aattctgctt tagaaactat tgttttaagc agagatgagg atgtcccttg cactatcggg    4260
tatgctttta ggttacggct tattggaaag attgttcata gctttgctgt tagatcctgg    4320
cagtttgcac aaagtaatct ttgttaacgt ttggttcata tgagtaagag gtacaacatt    4380
taaatgactt aattccccctt tgagaagatg gttgaagtca ttttattggc taaatgaaca    4440
tttaaagcaa gagtataaag gctacacagc atgacatctt tcttagatta tctgaattca    4500
tacttaaagc tcttaatgta tgcataacta tacaaaaaaa ttcatgcatc gtgatgcatc    4560
cattgcaaat atatccccat caatctccta gctctaatca acaaatccga tccatgcgca    4620
tcctatcaaa agtgcgtaga cattaatgga atgccacttt gcccaacttg gctgtaaggg    4680
aagaaacttg aatgaggtat tgtttcatta gaaagagctac taacgtcttt aggtttcagg    4740
tctgtctcgc atacaaacat tcccggaaaa tcagtagttt taccttgcc acaggtgatt    4800 gctatagctc agtatcctgg acattcttgt ggttaatgca tggcttagat tgtctatttt    4860
ctttgttaat cacaggtgtc tgaaatgcat gcccaaatat cctgcaaaaa caacgcattt    4920
tttgtaactg attttcagag tgaacatggt acttgggtta tagagtaagc tccatgagtt    4980
ctttatacaa ctgtactata agtgcatcac atttattagt ctatgaagac aaaagaatta    5040
```

| | |
|---|---|
| cattgttctg cattatgtag taatgaaggc agaagatatc gggtgtctcc aaacttccct | 5100 |
| atgcgttttc attcatcaga tgtaatcgta tttggttctg ataaggtgtg attcgtgaaa | 5160 |
| ttcttgcttg atatgcttta aaagatacgt tggcattggc agtagcttat tactcattca | 5220 |
| aatccatttg tttatgttat gcgggcagca tttcgtgtaa agacaatgaa atttccttca | 5280 |
| aaaactgctg aagcgaagga agagcgcaaa gtcgtgggga cagcataaac gggaaatttg | 5340 |
| tacagcattt tatagaaaca tcagacattg tagaagattg ataaacaaaa cagattcaac | 5400 |
| aaatacagag attatttggc tttcttctaa agaacgtgga aaaagtgatg gtcattgttt | 5460 |
| cttattctac catttcctaa atgtatagag aaagtgatgg tcattgtttc ttattctacc | 5520 |
| atttcctaaa tatatactaa ttctctatgt atatacaatt ataggccagt ttccttcatg | 5580 |
| aatttctttt atagattttc gtatttgtaa gtcttcattc aaaattaact actatttttt | 5640 |
| acttttattt ctaacgtgca ttatttttta cttttatttc taacttgcat tttatgttca | 5700 |
| ttgttgattt tatacataat aaaatgaaac aaatagaaaa aaataataaa tt | 5752 |

<210> SEQ ID NO 98
<211> LENGTH: 1971
<212> TYPE: DNA
<213> ORGANISM: Capsicum annuum

<400> SEQUENCE: 98

| | |
|---|---|
| atgtattcaa ctgtgtttta cacttcagtt catccctcca cttcagtttt ttcaagaaaa | 60 |
| cagctacctt tattgatatc caaggacttt cctgcagagt tgtatcattc tttaccttgt | 120 |
| aagagtttgg aaaatgggca tatcaagaag gttaaaggag taaaagccac actagctgaa | 180 |
| gctccagcta ctcctacaga gaagagtaac tctgaggttc cacagaagaa gttgaaagta | 240 |
| cttgtggcag tggtgggat tggaggatta gttttttgctt tggcagcaaa gaaaaagggg | 300 |
| tttgatgtat tggtgtttga gagagattta agtgctataa gaggtgaggg gcaatataga | 360 |
| ggtccaattc agatacagag caatgcattg gctgctttgg aagcaattga tatggatgtt | 420 |
| gctgaagaga tcatgaatgc tggctgtatc actggtcaaa ggattaatgg cttggtcgat | 480 |
| ggtatttctg gcaactggta ttgcaagttt gatacgttca ctccagctgt ggaacgtgga | 540 |
| cttcctgtga caagagtcat cagccgcatg actttgcaac agattcttgc acgtgctgta | 600 |
| ggggaggatg taattatgaa tgaaagtaat gtagtaaatt ttgaggatga tggggagaag | 660 |
| gtaatgctag gtttgatctc tttgtttttct gctacaggtg atcttctggt tggtgctgat | 720 |
| ggcataaggt ctaaggtacg gactaatttg ttcggacaca gtgaagctac ttactctggt | 780 |
| tacacttgtt atactggaat tgcagatttc gttcctgctg atattgacac agttgggtac | 840 |
| cgagtctttt tgggccacaa acagtacttt gtttcttcag atgtgggtgg aagcaagatg | 900 |
| cagtggtatg catttcacaa tgaaccagct ggtggtgtgg atgctccaaa cggtaaaaag | 960 |
| gaaagattgc ttaaaatatt tgggggatgg tgtgacaacg ttatagacct attagttgcc | 1020 |
| acagatgaag atgcaattct tcgtcgtgac atctatgata gaccgccaac atttaattgg | 1080 |
| ggaagaggtc gtgttacatt gcttgggac tcagtccatg ctatgcagcc taatttgggt | 1140 |
| caaggaggat gcatggccat agaggatagc tatcaactag cactggaact tgagaaagca | 1200 |
| tggagccgaa gtgctgagtc cggaagccct atggatgtca tctcatcttt aaggagctat | 1260 |
| gaaagtgcta gaaaacttcg agttggagtt atccatggac tggctagaat ggctgcaatc | 1320 |
| atggcatcaa cttacaaggc ctatcttggt gtcggacttg gtccattatc agtatggacc | 1380 |
| aagtatagga taccacatcc tggaagagtt ggtggaagag tatttgtgga cttgggaatg | 1440 |

```
cctctaatgt taagttgggt tctaggaggc aacgggagaa tacaacattg caggctatct    1500
gagaaagcaa atgatcaatt gagaagatgg tttgaagatg atgatgcttt agagcgtgct    1560
actgatgcag agtggttact gttacctgca gcgaatggca attctgcttt agaaactatt    1620
gttttaagca gagatgagga tgtcccttgc actatcgggt ctgtctcgca tacaaacatt    1680
cccggaaaat cagtagtttt acctttgcca caggtgtctg aaatgcatgc ccaaatatcc    1740
tgcaaaaaca acgcattttt tgtaactgat tttcagagtg aacatggtac ttgggttata    1800
gataatgaag gcagaagata tcgggtgtct ccaaacttcc ctatgcgttt tcattcatca    1860
gatgtaatcg tatttggttc tgataaggca gcatttcgtg taaagacaat gaaatttcct    1920
tcaaaaactg ctgaagcgaa ggaagagcgc aaagtcgtgg ggacagcata a             1971
```

```
<210> SEQ ID NO 99
<211> LENGTH: 5752
<212> TYPE: DNA
<213> ORGANISM: Capsicum annuum

<400> SEQUENCE: 99
```

```
cccaataacc caatactaat aacttaataa tattttatc ggttcgattt atcgatcggc       60
tcaactacca aaggaacaa aaaaataaat agagtactac aacaaccata gatgagtgaa      120
caagcgtcaa acatcagcct cagtttagta acccaaacaa gctacaatga caagccacct     180
ggccataaaa tcttcaccat tgctgcttca tggaccattg attggttctc aatcttcttt     240
gccccaccac caccaccacc ctcactatca cccacaattt ccacttcctt ttttccctcc     300
tcaaaagcct aactaacaca cattggccta actaaaattc tcataaatca ccttcacttc     360
tttttttcat tagattatac attagttgtt tggtctcaat cttcctttca cttcctttgg     420
cctaattaac agtttatata aatcaacttc acttcttttt ttcactaaaa catacagtga     480
aagagaaaca caagagtctt ttcttgaact ggagttctag tgaaagatgt attcaactgt     540
gttttacact tcagttcatc cctccacttc agttttttca agaaaacagc tacctttatt     600
gatatccaag gacttcctg cagagttgta tcattcttta ccttgtaaga gtttggaaaa     660
tgggcatatc aagaaggtta aaggagtaaa agccacacta gctgaagctc cagctactcc     720
tacagagaag agtaactctg aggttccaca gaagaagttg aaagtacttg tggcaggtgg     780
tgggattgga ggattagttt ttgctttggc agcaaagaaa aagggggttg atgtattggt     840
gtttgagaga gatttaagtg ctataagagg tgaggggcaa tatagaggtc caattcagat     900
acagagcaat gcattggctg cttttggaagc aattgatatg gatgttgctg aagagatcat     960
gaatgctggc tgtatcactg gtcaaaggat taatggcttg gtcgatggta tttctggcaa    1020
ctggtaaatt cacatcactc tgatttgatt gtgctgatta agagcttgtg tgccttttt     1080 gctactgtat ttactttcca aacttgttcg gttatgcttt acttaagccg agggtcttca    1140
ggaatagtct ctctaccttc acgagatatg attaaggtct cgcacgcaa tacccttctc     1200 agaagggtaa tcacactggc tatgttgttg ttgtaattaa atgcttgtct gtctttttt     1260 agttgagctt taactgagga tacccccagga aataatgaa ttctttgaaa tatttagccc    1320
tttaaaaaag tatagggaaa ataattcatt tagtcacaag tttattgaat catggttgcc    1380
aagcttattc gggaaaagga tcctatcttt accttcaaat ggcttcaatc agattgataa    1440
gttagtctta ttgttgtatg agcagcttat tgtgagaaca gtccctttat ttcttgaact    1500
gcgaacagtg acaatagttg ggtatcaggt attgcaagtt tgatacgttc actccagctg    1560
```

```
tggaacgtgg acttcctgtg acaagagtca tcagccgcat gactttgcaa cagattcttg    1620
cacgtgctgt aggggaggat gtaattatga atgaaagtaa tgtagtaaat tttgaggatg    1680
atggggagaa ggtaatgcta ggtttgatct ctttgttttc tgctattctc aaaatatcaa    1740
gaaagattat aacttttctt aatttcattt gcatcattgt taattgttgt ttcttattca    1800
tcaattttcg ttaaagcttc tcatgtgctg tgtgaaatca ggttactgtg gttcttgaga    1860
atggacaacg gtttacaggt gatcttctgg ttggtgctga tggcataagg tctaaggtat    1920
tcaaaatcag tctcattata tttctttcta ttattactac ttcggttaac aaggatagag    1980
taacttgttt atattttact ttgagattgt ggttccacgt taaaaaattg tctgttgact    2040
gataggcctg agtccgtatt atgcagtgaa ccttttattg attattctag ttgattcaga    2100
agatcacaaa catttccgtt gtgttgtagg tacggactaa tttgttcgga cacagtgaag    2160
ctacttactc tggttacact tgttatactg gaattgcaga tttcgttcct gctgatattg    2220
acacagttgg gtatgatatt ctttcttacc ggattgtgtt tccactcatg cccttatccc    2280
tgctggtgcc gttacactca cacgaggttt tcatagtaga gattaaattg agatttcttt    2340
tctgaaggta ccgagtcttt ttgggccaca aacagtactt tgtttcttca gatgtgggtg    2400
gaggcaagat gcagtggtat gcatttcaca atgaaccagc tggtggtgtg gatgctccaa    2460
acggtaaaat ttttaggccg cttaaaacta tttactatag ttcaggatat agacatactt    2520
actagaagac gttttgaat gcttaacttg taacgtttat ttaacccaag gggtttctta    2580 agaattttc ctcattgagg cctggttata gtgttgcaat aaggtaaaga caactcaag     2640 attagaataa gatagactca aatgtattat gagtcggaaa gttttgaatt gaagttgctg    2700
actctatgaa ttaggagttg tttaatattt tgtctgttca tgctgcaggt aaaaaggaaa    2760
gattgcttaa aatatttggg ggatggtgtg acaacgttat agacctatta gttgccacag    2820
atgaagatgc aattcttcgt cgtgacatct atgatagacc gccaacattt aattggggaa    2880
gaggtcgtgt tacattgctt ggggactcag tccatgctat gcagcctaat ttgggtcaag    2940
gaggatgcat ggccatagag gtacaccact gtgtttatca tctttgtcaa atacacagta    3000
ttgtaaggtt gtgtatgaca ctgaacttt ccatgtacaa ctacaggata gctatcaact    3060
agcactggaa cttgagaaag catggagccg aagtgctgag tccggaagcc ctatggatgt    3120
catctcatct ttaaggaggt aatccattat ttattggctc aagtgctgta gtctggttgg    3180
ttgagtacag gctgccagtt catgataatt gaaaaaacat ttgcaattgg ttgaggtctt    3240
taacttcacc ccaccaccag cccagtagga ctgctttaaa tgcctcaact gaaaatggat    3300
tgatttgaac agctgccgtg tctgccagtt cgctgatcct ttaatgaatt tccttttttct   3360 gcagctatga aagtgctaga aaacttcgag ttggagttat ccatggactg gctagaatgg    3420
ctgcaatcat ggcatcaact tacaaggcct atcttggtgt cggacttggt ccattatcag    3480 tatgaaaac tatctatcac ttgaaattgg aatggcatag ccaatttgcg tgattgcgca    3540
gagctcttct tataatagat gttttttttct attatttgtg cagttttga ccaagtatag    3600 gataccacat cctggaagag ttggtggaag agtatttgtg gacttgggaa tgcctctaat    3660
gttaagttgg gttctaggag gcaacgggta ggaatatgcg agctgtattc cagcattttc    3720
ttgcttcagt atttttgaaca tgattttggt ttctatgtga atccgtgatg agtttgctgg    3780
agatcttgga agttgatatc ctgtggtttg actcgtcttt tttcttttct tgcagcgaca    3840
agcttgaggg tagaatacaa cattgcaggc tatctgagaa agtatgtagc gtaaggaact    3900
atgcactcaa cacacgaaca cagaaaagat ttctggcttc cattgctact taattaaggt    3960
```

-continued

```
ccaactatgg attttacggg tgtgttaata tactgtactg tggtgatgaa ggcaaatgat     4020
caattgagaa gatggtttga agatgatgat gctttagagc gtgctactga tgcagagtga     4080
gttaatggaa cgtaatattt aaaaatttca tttttacatg tctcattttc ctagtttgct     4140
ttctaatttg gtgcttacgt tttatctttc aggtggttac tgttacctgc agcgaatggc     4200
aattctgctt tagaaactat tgttttaagc agagatgagg atgtcccttg cactatcggg     4260
tatgctttta ggttacggct tattggaaag attgttcata gctttgctgt tagatcctgg     4320
cagtttgcac aaagtaatct ttgttaacgt ttggttcata tgagtaagag gtacaacatt     4380
taaatgactt aattcccctt tgagaagatg gttgaagtca ttttattggc taaatgaaca     4440
tttaaagcaa gagtataaag gctacacagc atgacatctt tcttagatta tctgaattca     4500
tacttaaagc tcttaatgta tgcataacta tacaaaaaaa ttcatgcatc gtgatgcatc     4560
cattgcaaat atatccccat caatctccta gctctaatca acaaatccga tccatgcgca     4620
tcctatcaaa agtgcgtaga cattaatgga atgccacttt gcccaacttg gctgtaaggg     4680
aagaaacttg aatgaggtat tgtttcatta gaagagctac taacgtcttt aggtttcagg     4740
tctgtctcgc atacaaacat tcccggaaaa tcagtagttt tacctttgcc acaggtgatt     4800
gctatagctc agtatcctgg acattcttgt ggttaatgca tggcttagat tgtctatttt     4860
ctttgttaat cacaggtgtc tgaaatgcat gcccaaatat cctgcaaaaa caacgcattt     4920
tttgtaactg attttcagag tgaacatggt acttgggtta tagagtaagc tccatgagtt     4980
ctttatacaa ctgtactata agtgcatcac atttattagt ctatgaagac aaaagaatta     5040
cattgttctg cattatgtag taatgaaggc agaagatatc gggtgtctcc aaacttccct     5100
atgcgttttc attcatcaga tgtaatcgta tttggttctg ataaggtgtg attcgtgaaa     5160
ttcttgcttg atatgcttta aaagatacgt tggcattggc agtagcttat tactcattca     5220
aatccatttg tttatgttat gcaggcagca tttcgtgtaa agacaatgaa atttccttca     5280
aaaactgctg aagcgaagga agagcgcaaa gtcgtgggga cagcataaac gggaaatttg     5340
tacagcattt tatagaaaca tcagacattg tagaagattg ataaacaaaa cagattcaac     5400
aaatacagag attatttggc tttcttctaa agaacgtgga aaaagtgatg gtcattgttt     5460
cttattctac catttcctaa atgtatagag aaagtgatgg tcattgtttc ttattctacc     5520
atttcctaaa tatatactaa ttctctatgt atatacaatt ataggccagt ttccttcatg     5580
aatttctttt atagattttc gtatttgtaa gtcttcattc aaaattaact actattttt      5640 acttttattt ctaacttgca ttattttta cttttatttc taacttgcat tttatgttca     5700
ttgttgattt tatacataat aaaatgaaac aaatagaaaa aaataataaa tt             5752
```